(12) United States Patent
Hatakeyama et al.

(10) Patent No.: US 10,012,902 B2
(45) Date of Patent: Jul. 3, 2018

(54) POSITIVE RESIST COMPOSITION AND PATTERN FORMING PROCESS

(71) Applicant: Shin-Etsu Chemical Co., Ltd., Tokyo (JP)

(72) Inventors: Jun Hatakeyama, Joetsu (JP); Teppei Adachi, Joetsu (JP); Masaki Ohashi, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/434,228

(22) Filed: Feb. 16, 2017

(65) Prior Publication Data

US 2017/0242339 A1    Aug. 24, 2017

(30) Foreign Application Priority Data

Feb. 19, 2016   (JP) .................. 2016-029682

(51) Int. Cl.
| | |
|---|---|
| G03F 7/004 | (2006.01) |
| G03F 7/039 | (2006.01) |
| G03F 7/40 | (2006.01) |
| G03F 7/20 | (2006.01) |
| G03F 7/32 | (2006.01) |
| C07C 381/12 | (2006.01) |
| H01L 21/027 | (2006.01) |
| G03F 7/11 | (2006.01) |
| C08F 220/30 | (2006.01) |
| C08F 220/34 | (2006.01) |
| C08F 220/38 | (2006.01) |
| G03F 7/16 | (2006.01) |
| G03F 7/38 | (2006.01) |
| C08F 220/28 | (2006.01) |

(52) U.S. Cl.
CPC ............ *G03F 7/039* (2013.01); *C07C 381/12* (2013.01); *C08F 220/30* (2013.01); *C08F 220/34* (2013.01); *C08F 220/38* (2013.01); *G03F 7/004* (2013.01); *G03F 7/0397* (2013.01); *G03F 7/11* (2013.01); *G03F 7/162* (2013.01); *G03F 7/168* (2013.01); *G03F 7/2002* (2013.01); *G03F 7/2004* (2013.01); *G03F 7/2037* (2013.01); *G03F 7/32* (2013.01); *G03F 7/327* (2013.01); *G03F 7/38* (2013.01); *G03F 7/40* (2013.01); *H01L 21/0274* (2013.01); *C08F 2220/281* (2013.01); *C08F 2220/282* (2013.01); *C08F 2220/301* (2013.01); *C08F 2220/302* (2013.01); *C08F 2220/303* (2013.01); *C08F 2220/382* (2013.01); *C08F 2220/385* (2013.01); *C08F 2800/10* (2013.01)

(58) Field of Classification Search
CPC .......... G03F 7/004; G03F 7/0397; G03F 7/11; G03F 7/32; G03F 7/2002; G03F 7/40; H01L 21/0274; C08F 220/34; C08F 220/38; C08F 220/26; C08F 220/30; C07C 381/12
USPC ....... 430/942, 434, 435, 322, 325, 329, 331; 526/243, 326, 259, 310
See application file for complete search history.

(56) References Cited

U.S. PATENT DOCUMENTS

| | | | |
|---|---|---|---|
| 7,482,108 B2 | 1/2009 | Matsumaru et al. | |
| 8,101,333 B2* | 1/2012 | Noya | G03F 7/40 430/270.1 |
| 8,361,193 B2* | 1/2013 | Perkins | B60H 3/0071 55/385.3 |
| 2009/0280434 A1* | 11/2009 | Harada | G03F 7/0046 430/270.1 |
| 2013/0045444 A1* | 2/2013 | Taniguchi | G03F 7/0397 430/281.1 |
| 2013/0089819 A1* | 4/2013 | Kawaue | C07C 309/04 430/285.1 |
| 2013/0177852 A1* | 7/2013 | Yoon | G03F 7/031 430/285.1 |
| 2013/0323646 A1* | 12/2013 | Hatakeyama | G03F 7/0395 430/285.1 |
| 2014/0065540 A1* | 3/2014 | Wang | G03F 7/0045 430/281.1 |
| 2014/0093824 A1* | 4/2014 | Kawana | G03F 7/0388 430/296 |
| 2014/0168188 A1* | 6/2014 | Jun | G09G 3/3291 345/212 |
| 2014/0199631 A1* | 7/2014 | Sagehashi | C07C 69/54 430/281.1 |

(Continued)

FOREIGN PATENT DOCUMENTS

| | | |
|---|---|---|
| JP | 2006-45311 A | 2/2006 |
| JP | 2006-178317 A | 7/2006 |

(Continued)

OTHER PUBLICATIONS

Kishikawa et al., "Assessment of trade-off between resist resolution and sensitivity for optimization of hyper-NA immersion lithography", Proc. of SPIE, 2007, vol. 6520, pp. 65203L-1-9. (9 pages).

*Primary Examiner* — Amanda C Walke
(74) *Attorney, Agent, or Firm* — Westerman, Hattori, Daniels & Adrian, LLP

(57) ABSTRACT

A non-chemically-amplified positive resist composition comprising a polymer comprising both recurring units derived from a sulfonium salt capable of generating a fluorinated acid and recurring units containing an amino group as a base resin exhibits a high resolution and a low edge roughness and forms a pattern of good profile after exposure and organic solvent development.

6 Claims, No Drawings

(56) References Cited

U.S. PATENT DOCUMENTS

2015/0010866 A1* 1/2015 Osaki ................. G03F 7/325
　　　　　　　　　　　　　　　　　　　430/281.1
2015/0338744 A1* 11/2015 Hatakeyama .......... G03F 7/40
　　　　　　　　　　　　　　　　　　　430/331

FOREIGN PATENT DOCUMENTS

| JP | 2011-39266 A | 2/2011 |
| WO | 2013/141222 A1 | 9/2013 |

* cited by examiner

10,012,902 B2

POSITIVE RESIST COMPOSITION AND PATTERN FORMING PROCESS

CROSS-REFERENCE TO RELATED APPLICATION

This non-provisional application claims priority under 35 U.S.C. § 119(a) on Patent Application No. 2016-029682 filed in Japan on Feb. 19, 2016, the entire contents of which are hereby incorporated by reference.

TECHNICAL FIELD

This invention relates to a positive resist composition and a patterning process using the composition, and more particularly, to a non-chemically-amplified positive resist composition comprising a suitable polymer as a base resin.

BACKGROUND ART

To meet the demand for higher integration density and operating speed of LSIs, the effort to reduce the pattern rule is in rapid progress. The wide-spreading flash memory market and the demand for increased storage capacities drive forward the miniaturization technology. As the advanced miniaturization technology, manufacturing of microelectronic devices at the 65-nm node by the ArF lithography has been implemented in a mass scale. Manufacturing of 45-nm node devices by the next generation ArF immersion lithography is approaching to the verge of high-volume application. The candidates for the next generation 32-nm node include ultra-high NA lens immersion lithography using a liquid having a higher refractive index than water in combination with a high refractive index lens and a high refractive index resist film, extreme ultraviolet (EUV) lithography of 13.5 nm wavelength, and double patterning version of the ArF lithography, on which active research efforts have been made.

With respect to high-energy radiation of very short wavelength such as EB or X-ray, hydrocarbons used in resist materials have little absorption. Then resist materials based on polyhydroxystyrene composed mainly of hydrocarbon are under consideration.

The exposure system for mask manufacturing made a transition from the laser beam exposure system to the EB exposure system to increase the accuracy of line width. Since a further size reduction became possible by increasing the accelerating voltage of the electron gun in the EB exposure system, the accelerating voltage increased from 10 kV to 30 kV and reached 50 kV in the current mainstream system, with a voltage of 100 kV being under investigation.

As the feature size reduces, image blurs due to acid diffusion become a problem. To insure resolution for fine patterns with a size of 45 nm et seq., not only an improvement in dissolution contrast is important as previously reported, but control of acid diffusion is also important as reported in Non-Patent Document 1. Since chemically amplified resist compositions are designed such that sensitivity and contrast are enhanced by acid diffusion, an attempt to minimize acid diffusion by reducing the temperature and/or time of post-exposure bake (PEB) fails, resulting in drastic reductions of sensitivity and contrast.

The addition of an acid generator capable of generating a bulky acid is an effective means for suppressing acid diffusion. It was then proposed to incorporate in a polymer recurring units derived from an onium salt having a polymerizable unsaturated bond as acid generator. Patent Document 1 discloses a sulfonium salt having a polymerizable unsaturated bond, capable of generating a specific sulfonic acid and a similar iodonium salt. Patent Document 2 discloses a sulfonium salt having a sulfonic acid anion directly attached to the backbone.

Attention is paid again to non-chemically-amplified resist compositions because they are not affected by acid diffusion. In the early era, it was proposed to form a positive pattern by coating a resist film containing a polymer of backbone cleavage type as typified by polymethyl methacrylate (PMMA) and developing it in an organic solvent. The resist film is increased in sensitivity by copolymerizing α-chloroacrylate with α-methylstyrene to boost the efficiency of backbone cleavage.

Patent Document 3 discloses a non-chemically-amplified resist composition comprising a polymer containing anion-bound PAG units and amino-containing recurring units, but not acid labile group-containing recurring units as a base resin. From this resist composition, a negative pattern is formed via organic solvent development.

Patent Document 4 discloses a polymer containing anion-bound PAG units and amino-containing recurring units. Since this polymer contains acid labile group-containing recurring units as well, Patent Document 4 basically relates to a chemically amplified positive resist composition wherein the acid generated from the anion-bound PAG unit is quenched with the amino group. Since both the acid generated from the anion-bound PAG unit and the amino group for quenching the acid are bonded to the polymer backbone, diffusion is minimal. However, a lowering of resolution by acid diffusion is inevitable because the resist is basically of chemically amplified type.

Citation List

| | |
|---|---|
| Patent Document 1: | JP-A 2006-045311 (U.S. Pat. No. 7,482,108) |
| Patent Document 2: | JP-A 2006-178317 |
| Patent Document 3: | WO 2013/141222 |
| Patent Document 4: | JP-A 2011-039266 |
| Non-Patent Document 1: | SPIE Vol. 6520 65203L-1 (2007) |

SUMMARY OF INVENTION

An object of the present invention is to provide a positive resist composition which exhibits a high resolution surpassing prior art chemically amplified positive resist compositions, and forms a pattern of satisfactory profile with low edge roughness (LER, LWR), especially a non-chemically-amplified positive resist composition comprising a suitable polymer as a base resin; and a patterning process using the resist composition.

The inventors have found that a positive resist composition having a high resolution and a low edge roughness in current demand is reached by using a polymer comprising both recurring units derived from a sulfonium salt capable of generating a fluorinated acid and recurring units containing an amino group as a base resin.

In general, polymers comprising recurring units derived from a sulfonium salt have a low solubility in organic solvents. Specifically, a polymer comprising more than 5 mol % of recurring units derived from a sulfonium salt is less soluble in PGMEA (propylene glycol monomethyl ether acetate) which is commonly used as the resist solvent. Thus an auxiliary solvent offering high solubility such as cyclohexanone, cyclopentanone, γ-butyrolactone or PGME (propylene glycol monomethyl ether) must be added to PGMEA in order to dissolve the polymer in the solvent. A resist film formed from the polymer comprising recurring units derived from a sulfonium salt is not dissolved away in developers of ester and ketone organic solvents, typically butyl acetate.

Salts of fluorosulfonic acids or fluorosulfonimides with amines are known as ionic liquids. Ionic liquids are liquid over a wide range of temperature as suggested by their name and exhibit high solvent solubility.

The positive resist composition of the invention uses a polymer comprising both recurring units derived from a sulfonium salt capable of generating a fluorinated acid and recurring units containing an amino group as a base resin. In general, a sulfonium salt-containing polymer has a low organic solvent solubility and is not dissolved in an organic solvent developer. In the inventive resist composition comprising the polymer, the sulfonium salt in the exposed region of the resist film is decomposed to generate a fluorinated acid, which forms a salt with amine. The resulting acid-amine salt has the structure of ionic liquid. This brings about a drastic increase of solubility in developer, resulting in formation of a positive pattern with a high contrast.

Patent Document 3 describes a resist material comprising a copolymer of a sulfonium salt having a sulfonic acid anion bound to a polymer backbone and an amine. A negative pattern is formed from a film of this resist material through steps of exposure and organic solvent development. Upon light exposure, the sulfonium salt is decomposed to generate sulfonic acid, which forms a salt with the amine. In this sense, Patent Document 3 is similar to the present invention. In Patent Document 3, however, the salt formation takes place within the molecule or between molecules of the polymer. The intermolecular salt formation is pseudo-cross-linking which allows the resist pattern to swell in the developer. If the resist pattern swells in the developer, then adjacent line features merge together, resulting in line pattern collapse.

In the practice of the invention, the acid generated upon light exposure is free, and thus its salt formation with amine does not bring pseudo-intermolecular crosslinking, so that any swell in developer or line pattern collapse may be avoided.

In one aspect, the invention provides a positive resist composition adapted to form a positive pattern via organic solvent development, comprising a base resin containing a polymer comprising recurring units having the formula (1) and recurring units having the formula (2), but not recurring units adapted to increase a polarity by deprotection reaction with the aid of acid.

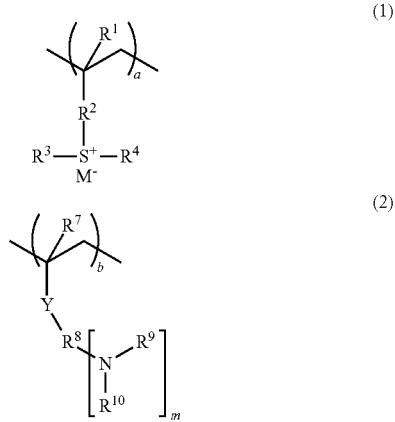

Herein $R^1$ and $R^7$ are each independently hydrogen or methyl, $R^2$ is a single bond, phenylene, —O—$R^5$— or —C(=O)—X—$R^5$—, X is —O— or —NH—, $R^5$ is a $C_1$-$C_6$ straight, branched or cyclic alkylene group, $C_2$-$C_6$ straight, branched or cyclic alkenylene group, phenylene group, or a combination thereof, which may contain a carbonyl, ester, ether or hydroxyl moiety, $R^3$ and $R^4$ are each independently a $C_1$-$C_{12}$ straight, branched or cyclic alkyl group, $C_6$-$C_{12}$ aryl group, $C_7$-$C_{20}$ aralkyl group or mercaptophenyl group, which may contain a carbonyl, ester or ether moiety, Y is a single bond, phenylene group or —C(=O)—O—, $R^8$ is a single bond, a $C_1$-$C_{10}$ straight, branched or cyclic alkylene group which may contain an ether moiety, ester moiety, —N= or —S—, or phenylene or naphthylene group, $R^9$ and $R^{10}$ are each independently hydrogen, $C_1$-$C_{10}$ straight or branched alkyl group, $C_2$-$C_{10}$ alkenyl group or $C_6$-$C_{10}$ aryl group, $R^9$ and $R^{10}$ may bond together to form a ring with the nitrogen atom to which they are attached, the ring may contain an ether moiety, sulfide moiety, disulfone moiety, nitrogen atom, double bond or aromatic moiety, either one of $R^9$ and $R^{10}$ may bond with $R^8$ to form a ring, $M^-$ is a non-nucleophilic counter ion containing at least one fluorine atom, a and b are numbers meeting $0.1 \le a \le 0.9$, $0.1 \le b \le 0.9$, and $0.1 \le a/b \le 1.5$.

In a preferred embodiment, the polymer further comprises recurring units containing a phenolic hydroxyl group. More preferably, the recurring units containing a phenolic hydroxyl group have the formula (3).

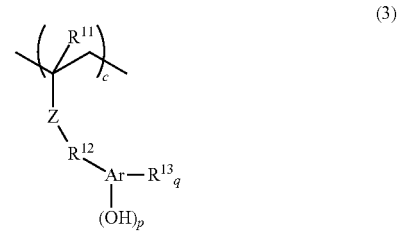

Herein Ar is a $C_6$-$C_{14}$ aromatic group which may contain a nitrogen atom, $R^{11}$ is hydrogen or methyl, $R^{12}$ is a single bond or a $C_1$-$C_{10}$ straight or branched alkylene group which may contain a hydroxyl, carboxyl, ester, ether moiety or lactone ring, $R^{13}$ is hydrogen, fluorine, trifluoromethyl, cyano, $C_1$-$C_{10}$ straight, branched or cyclic alkyl group, $C_1$-$C_{10}$ straight, branched or cyclic alkoxy group, $C_6$-$C_{14}$ aryl group, $C_2$-$C_{10}$ straight, branched or cyclic alkenyl group, $C_2$-$C_{10}$ straight, branched or cyclic alkynyl group, $C_2$-$C_{10}$ straight, branched or cyclic alkoxycarbonyl group, $C_2$-$C_{10}$ straight, branched or cyclic acyl group, or $C_2$-$C_{10}$ straight, branched or cyclic acyloxy group, p is an integer of 1 to 5, q is an integer of 0 to 4, Z is a single bond, —C(=O)—O— or —C(=O)—NH—.

The positive resist composition may further comprise an organic solvent and/or a surfactant.

In another aspect, the invention provides a pattern forming process comprising the steps of applying the positive resist composition defined herein onto a substrate, baking the composition to form a resist film, exposing the resist film to high-energy radiation, and developing the resist film in an organic solvent developer.

The high-energy radiation is typically EB or EUV of wavelength 3 to 15 nm.

The developer preferably contains at least one organic solvent selected from among 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

Advantageous Effects of Invention

The positive resist composition of the invention exhibits a high resolution and forms a pattern of satisfactory profile with minimal edge roughness after exposure since it is devoid of acid diffusion. Because of these advantages, the positive resist composition, especially non-chemically-amplified positive resist composition is best suited as a fine pattern-forming material for the manufacture of VLSIs and photomasks by EB lithography and a pattern-forming material for EUV lithography.

DESCRIPTION OF EMBODIMENTS

The singular forms "a," "an" and "the" include plural referents unless the context clearly dictates otherwise. The notation (Cn-Cm) means a group containing from n to m carbon atoms per group.

The abbreviations have the following meaning.
EB: electron beam
EUV: extreme ultraviolet
PAG: photoacid generator
PEB: post-exposure bake
LWR: line width roughness
Mw: weight average molecular weight
Mw/Mn: molecular weight distribution or dispersity
GPC: gel permeation chromatography Resist Composition A first embodiment of the invention is a resist composition comprising a base resin which includes a polymer comprising recurring units having the formula (1) and recurring units having the formula (2), but not recurring units adapted to increase a polarity by deprotection reaction with the aid of acid. It is noted that recurring units having formulae (1) and (2) are also referred to as recurring units (a) and (b), respectively.

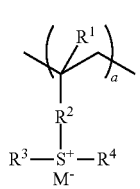
(1)

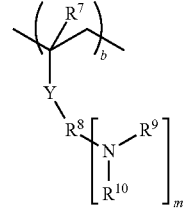
(2)

Herein $R^1$ and $R^7$ are each independently hydrogen or methyl. $R^2$ is a single bond, phenylene, —O—$R^5$— or —C(=O)—X—$R^5$—, wherein X is —O— or —NH—, and $R^5$ is a $C_1$-$C_6$ straight, branched or cyclic alkylene group, $C_2$-$C_6$ straight, branched or cyclic alkenylene group, phenylene group, or a combination thereof, which may contain a carbonyl, ester, ether or hydroxyl moiety. $R^3$ and $R^4$ are each independently a $C_1$-$C_{12}$ straight, branched or cyclic alkyl group, $C_6$-$C_{12}$ aryl group, $C_7$-$C_{20}$ aralkyl group or mercaptophenyl group, which may contain a carbonyl, ester or ether moiety. Y is a single bond, phenylene group or —C(=O)—O—. $R^8$ is a single bond, a $C_1$-$C_{10}$ straight, branched or cyclic alkylene group which may contain an ether moiety, ester moiety, —N= or —S—, or phenylene or naphthylene group. $R^9$ and $R^{10}$ are each independently hydrogen, $C_1$-$C_{10}$ straight or branched alkyl group, $C_2$-$C_{10}$ alkenyl group or $C_6$-$C_{10}$ aryl group, $R^9$ and $R^{10}$ may bond together to form a ring with the nitrogen atom to which they are attached, the ring may contain an ether moiety, sulfide moiety, disulfone moiety, nitrogen atom, double bond or aromatic moiety, either one of $R^9$ and $R^{10}$ may bond with $R^8$ to form a ring. $M^-$ is a non-nucleophilic counter ion containing at least one fluorine atom, a and b are numbers meeting the range: $0.1 \leq a \leq 0.9$, $0.1 \leq b \leq 0.9$, and $0.1 \leq a/b \leq 1.5$.

Examples of the monomer from which recurring unit (a) is derived are given below, but not limited thereto. Herein $R^1$ and $M^-$ are as defined above.

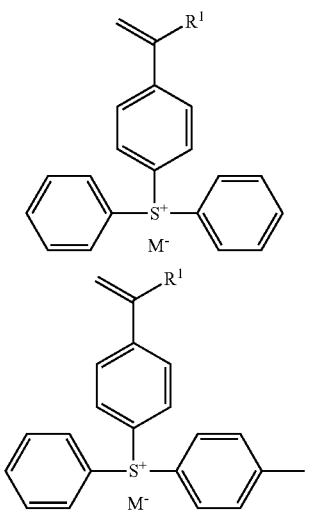

-continued
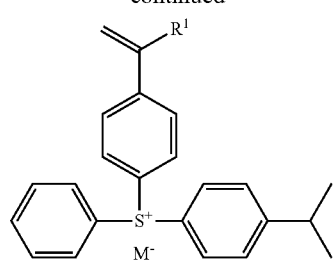
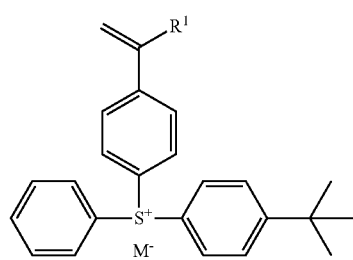
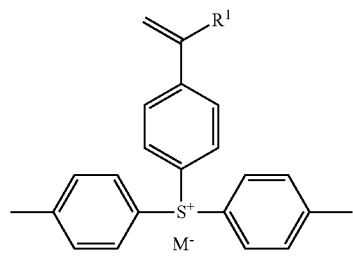
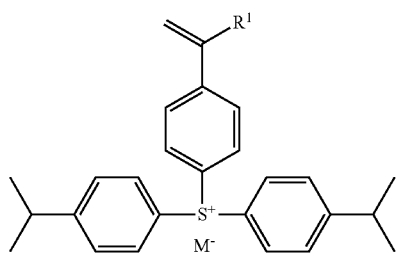
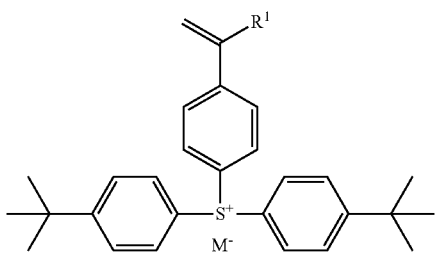
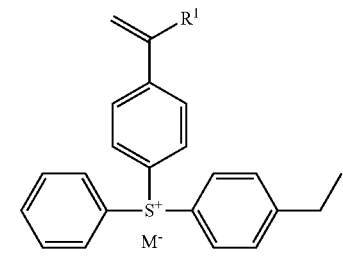
-continued
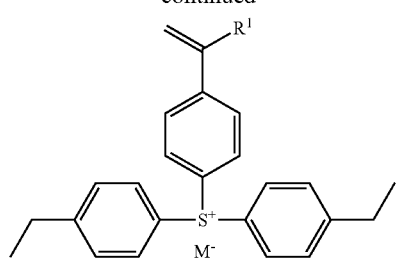
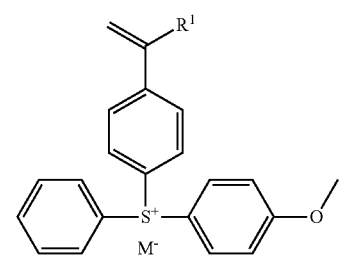
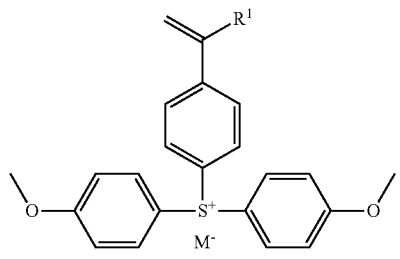
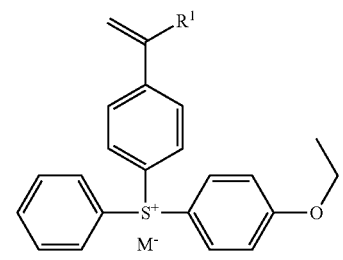
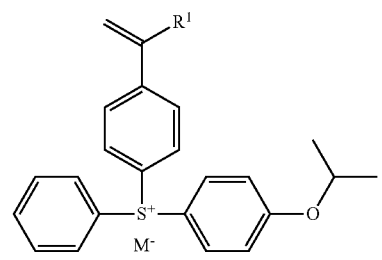
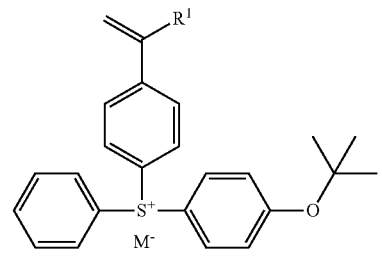

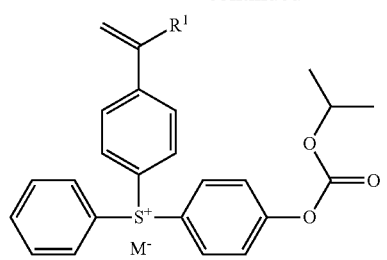
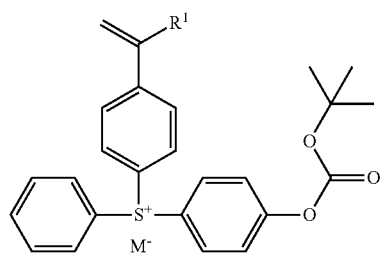
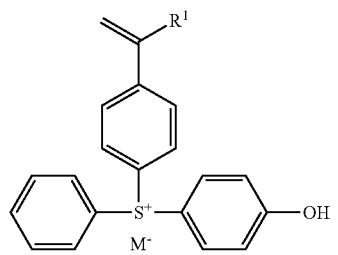
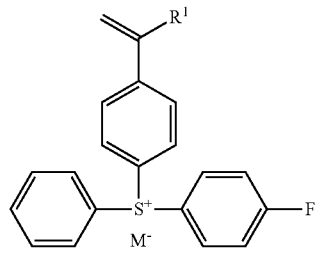
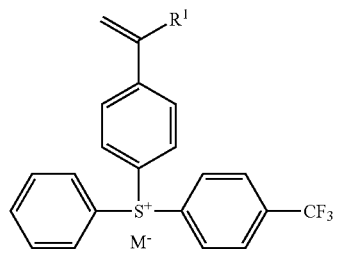
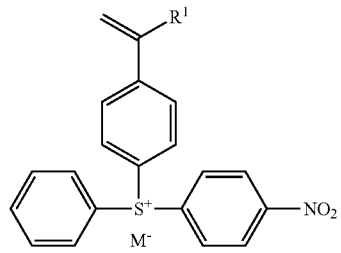
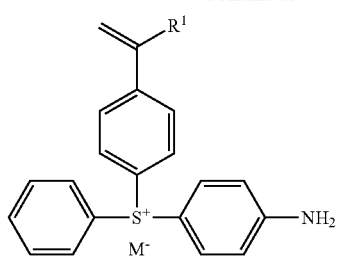
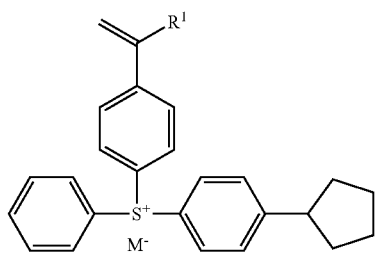
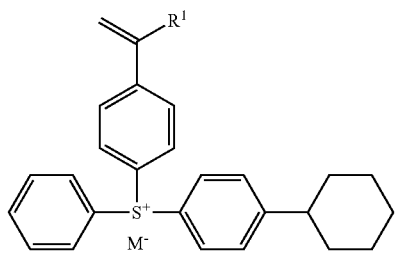
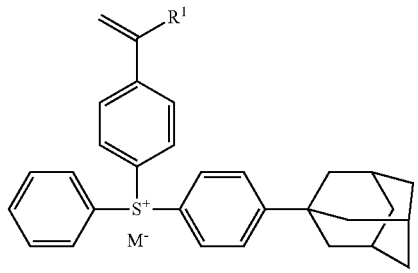
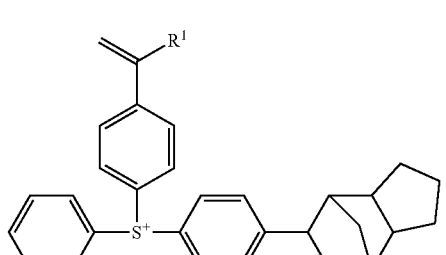
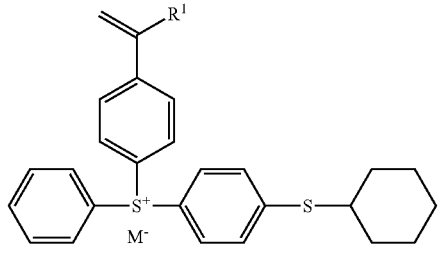

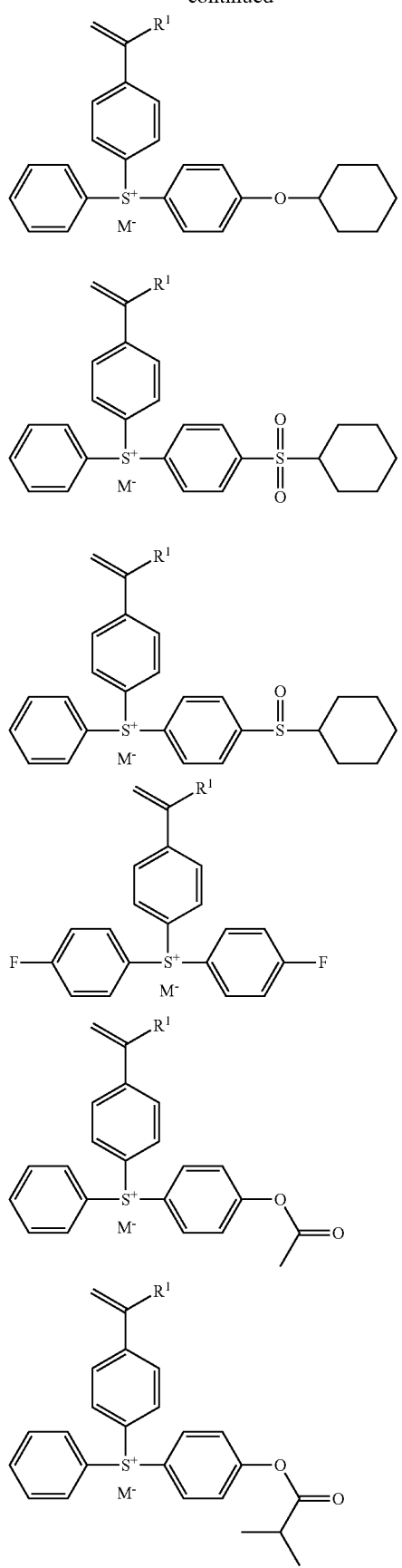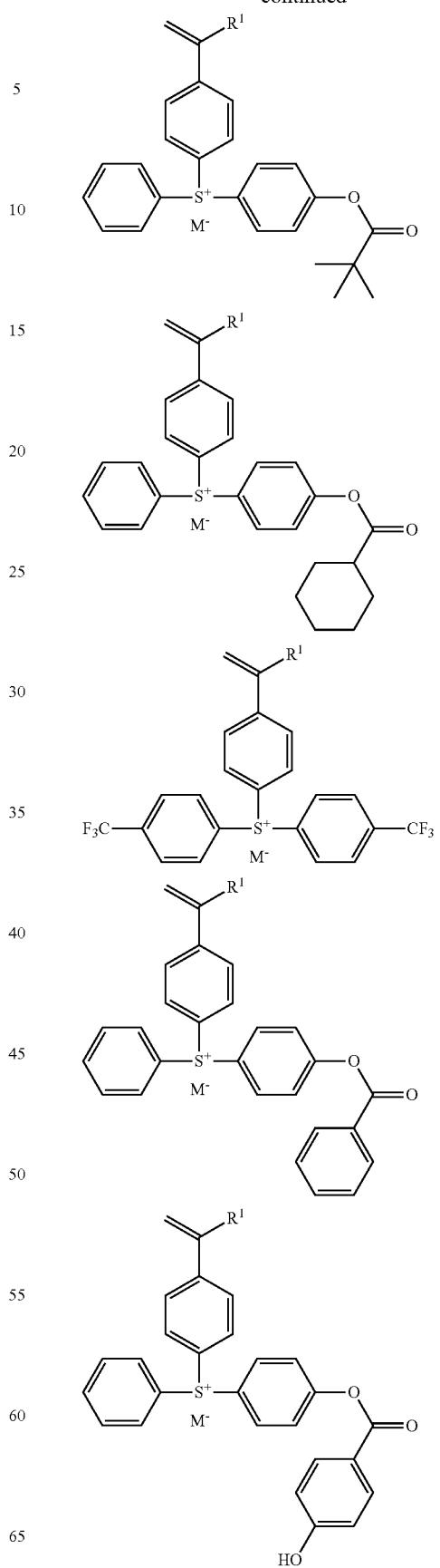

-continued
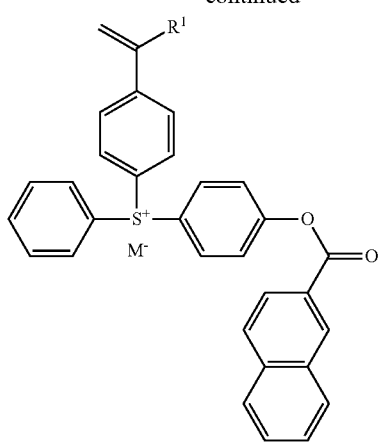
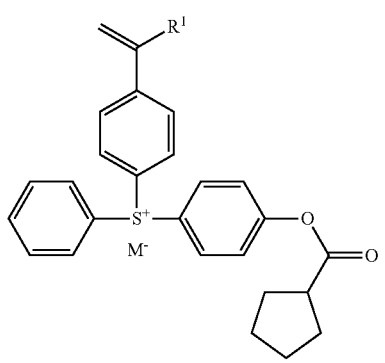
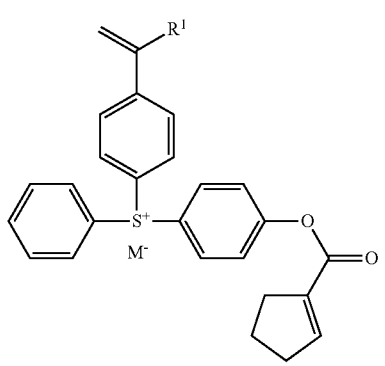
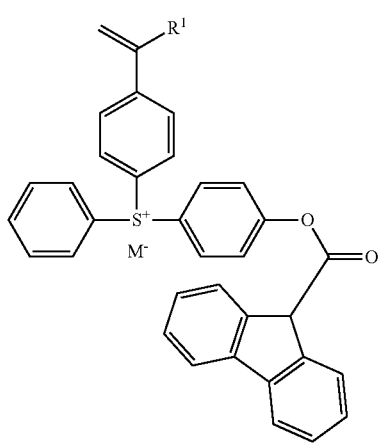
-continued
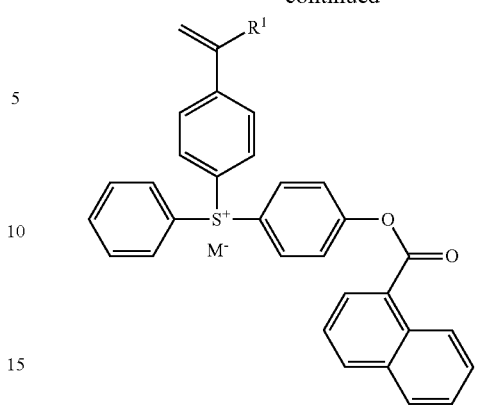
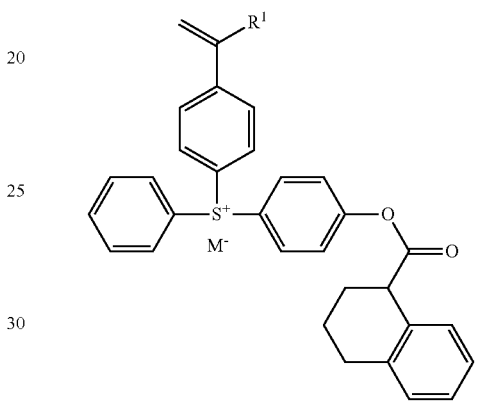
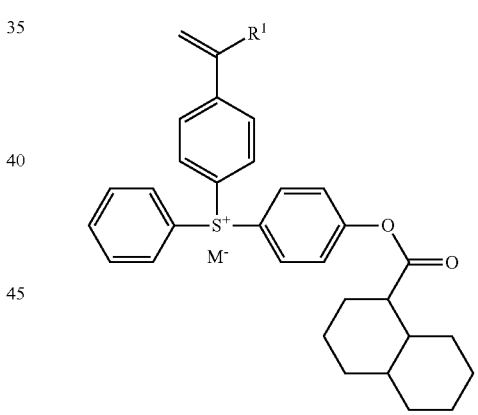
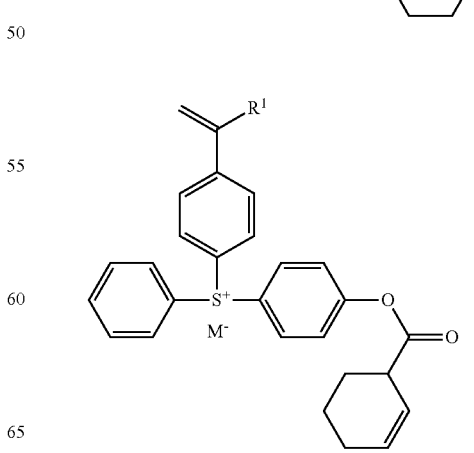

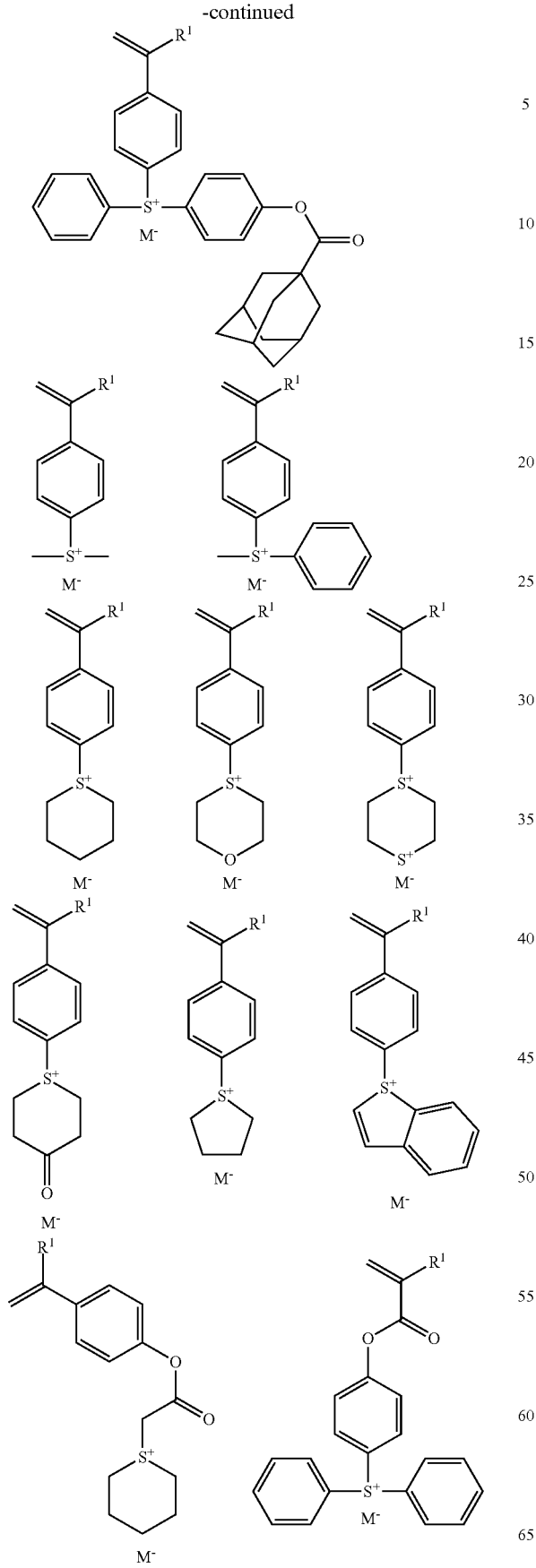
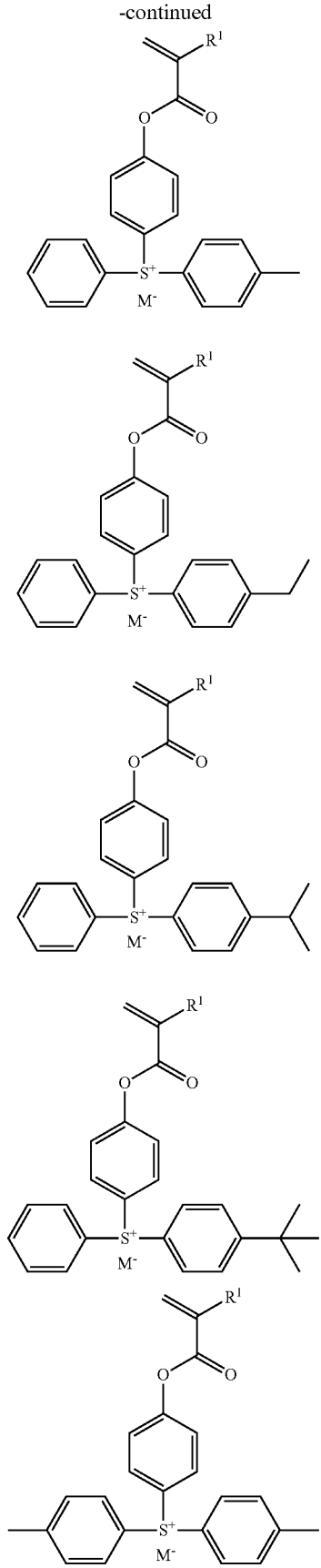

-continued
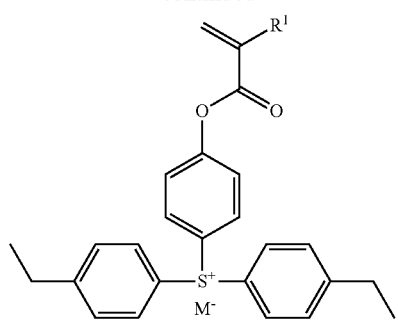
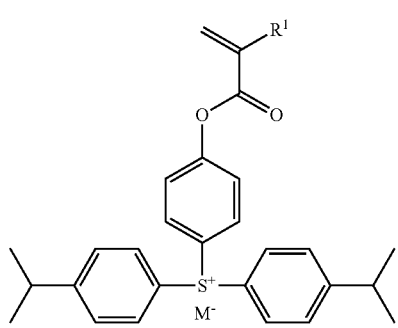
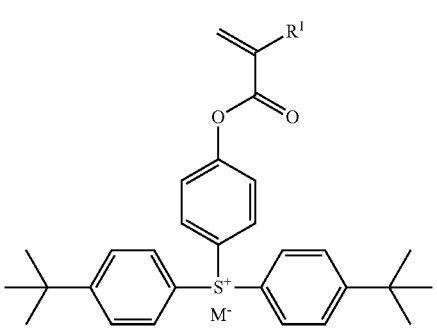
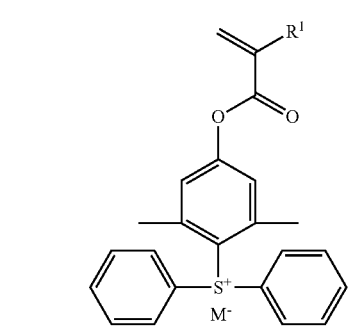
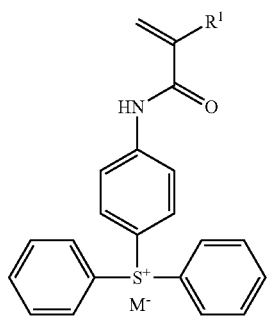
-continued
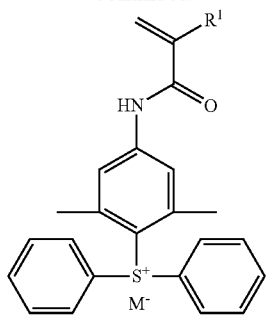
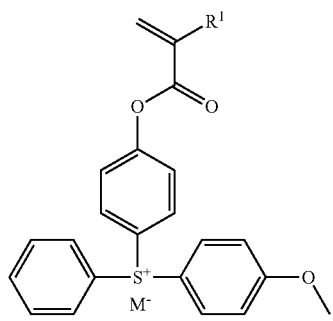
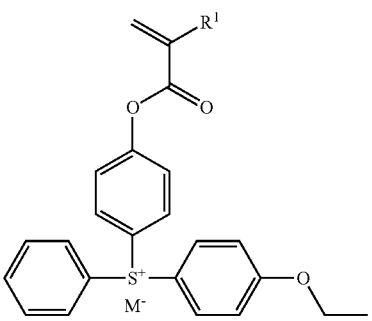
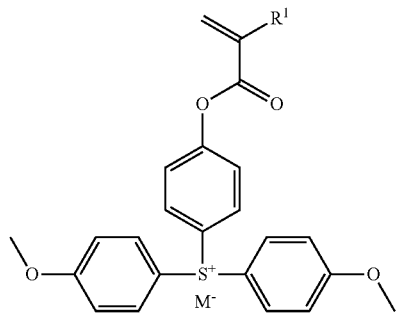
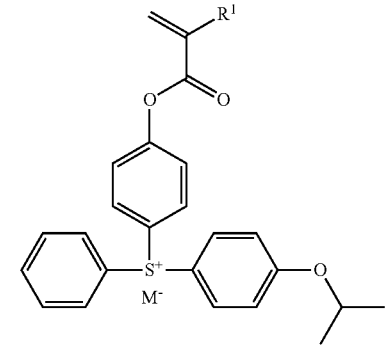

-continued
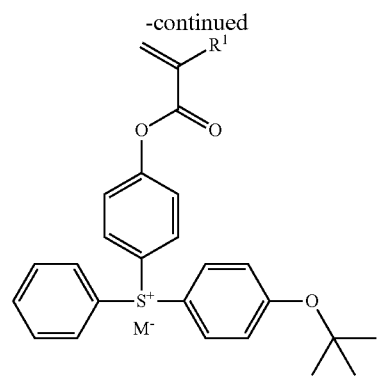
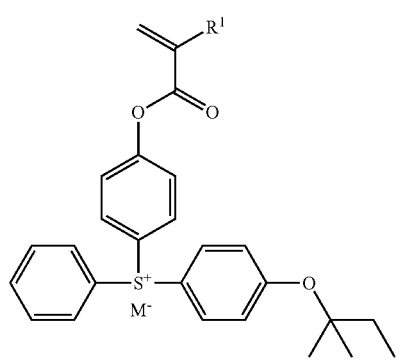
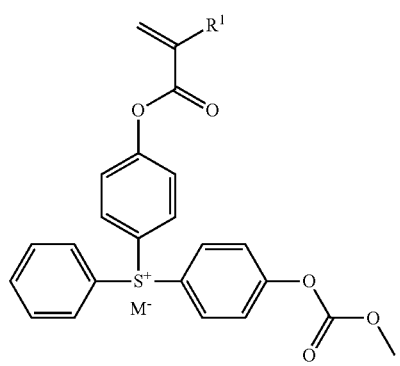
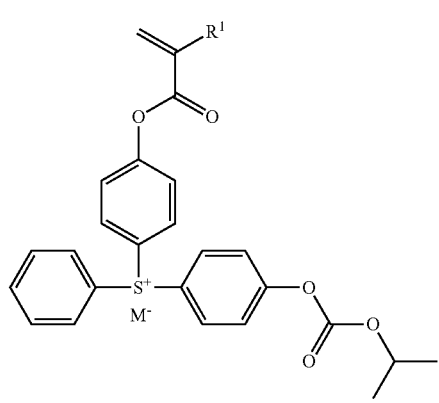
-continued
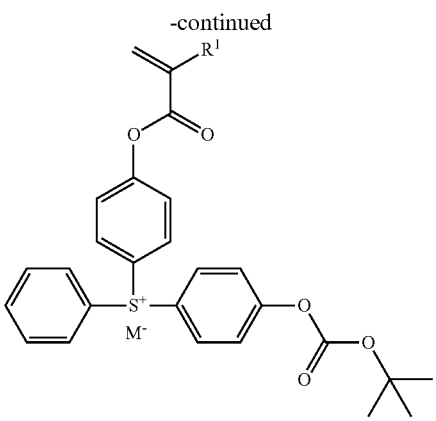
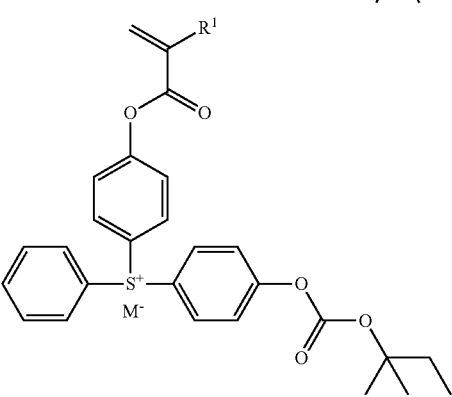
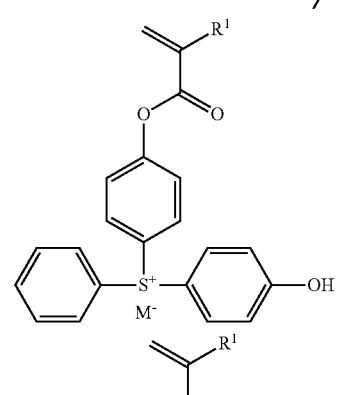
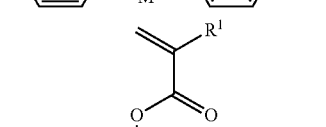
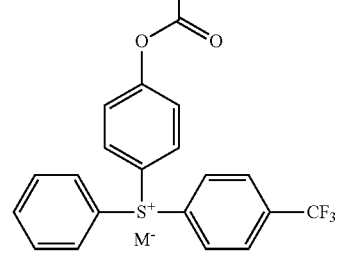

-continued
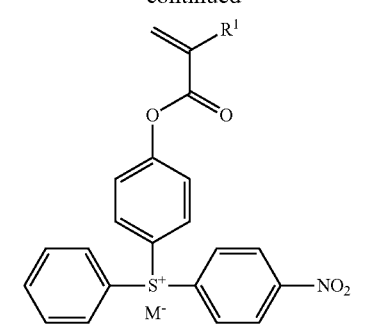
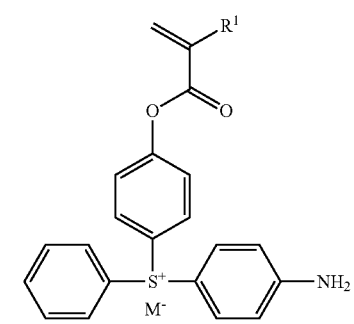
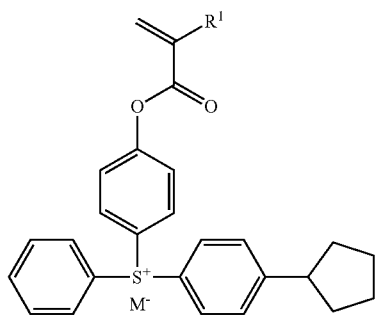
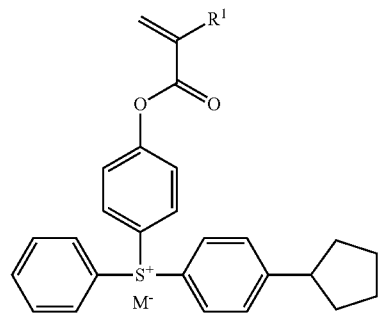
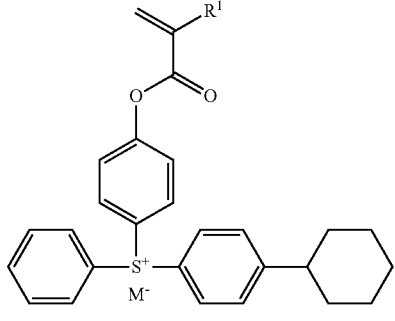
-continued
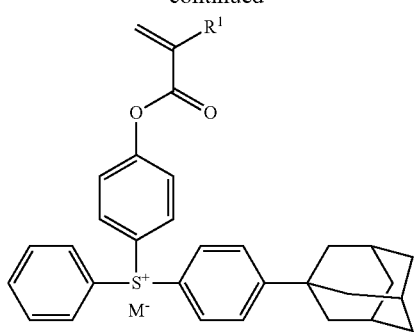
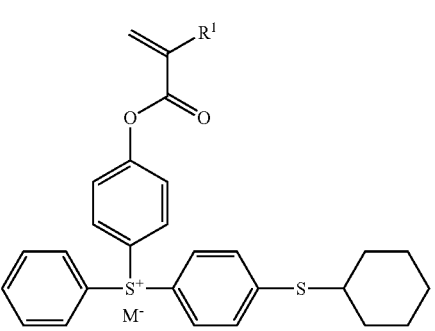
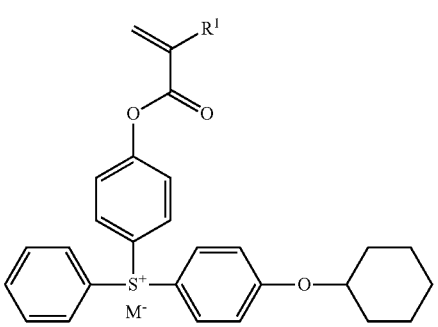
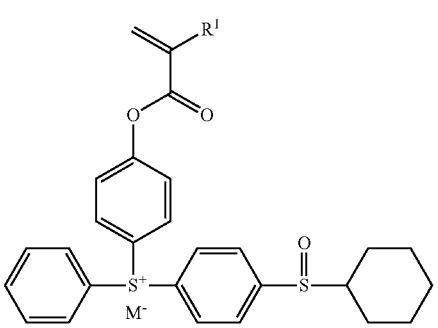
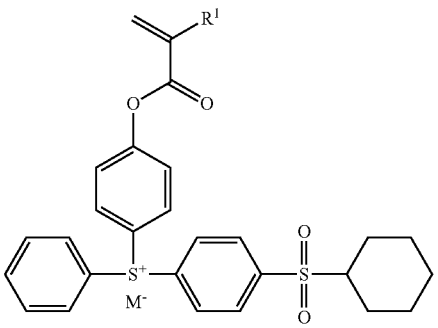

-continued
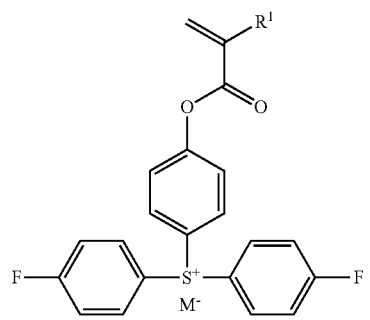
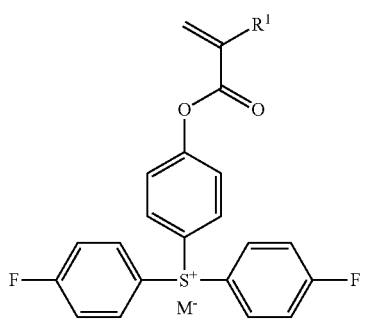
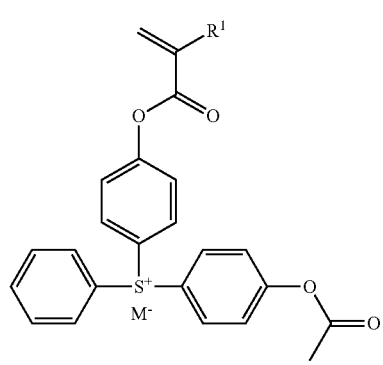
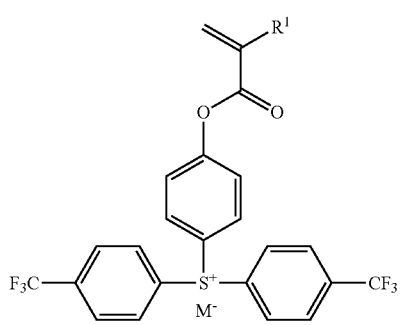
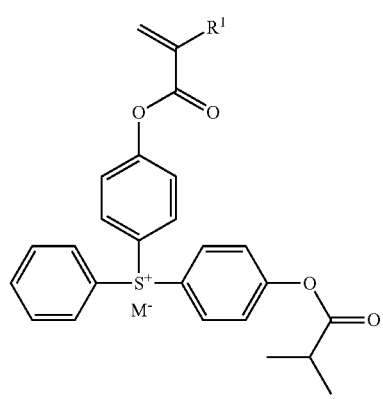
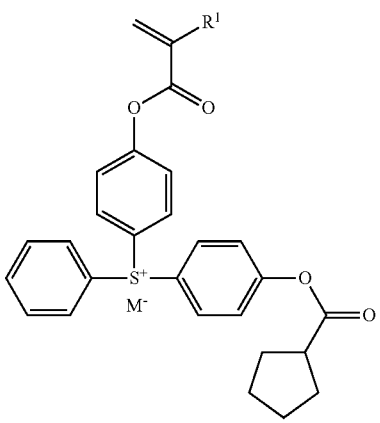
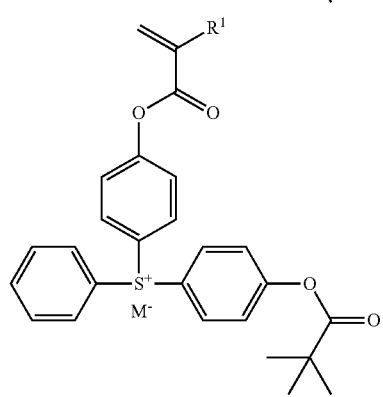
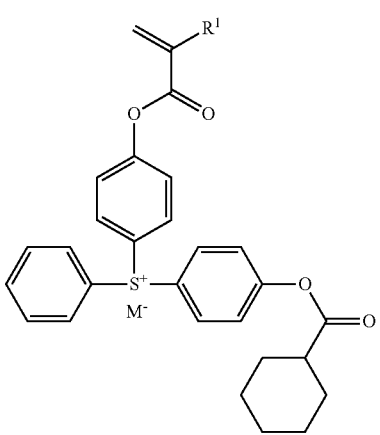

-continued
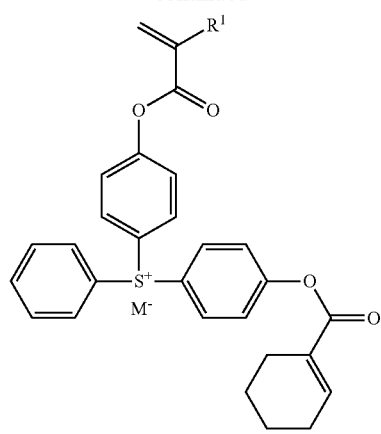
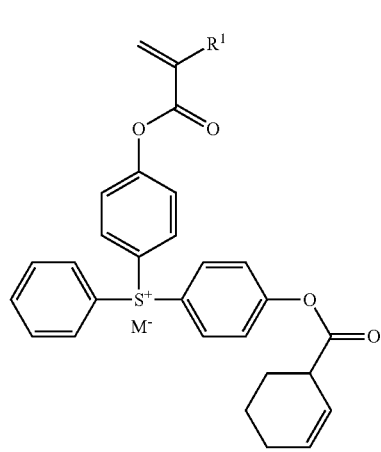
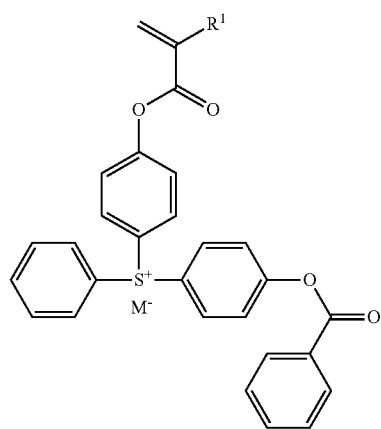
-continued
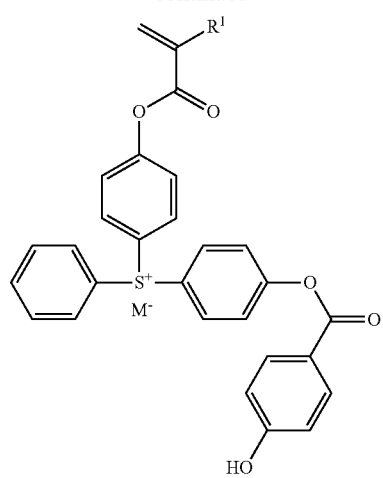
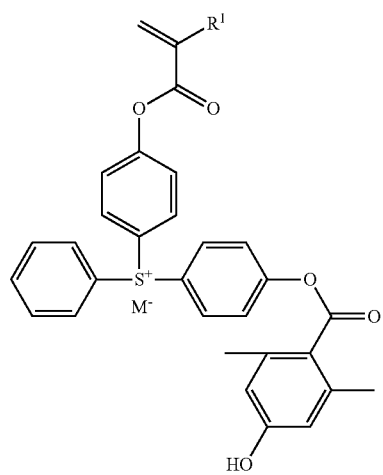
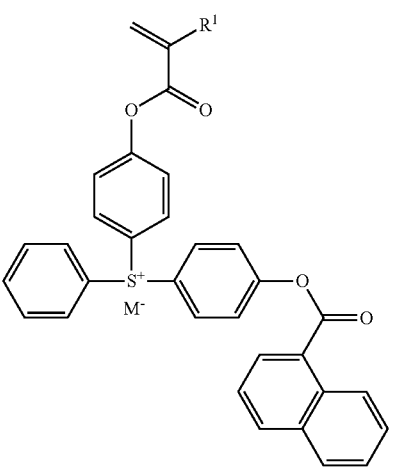

-continued
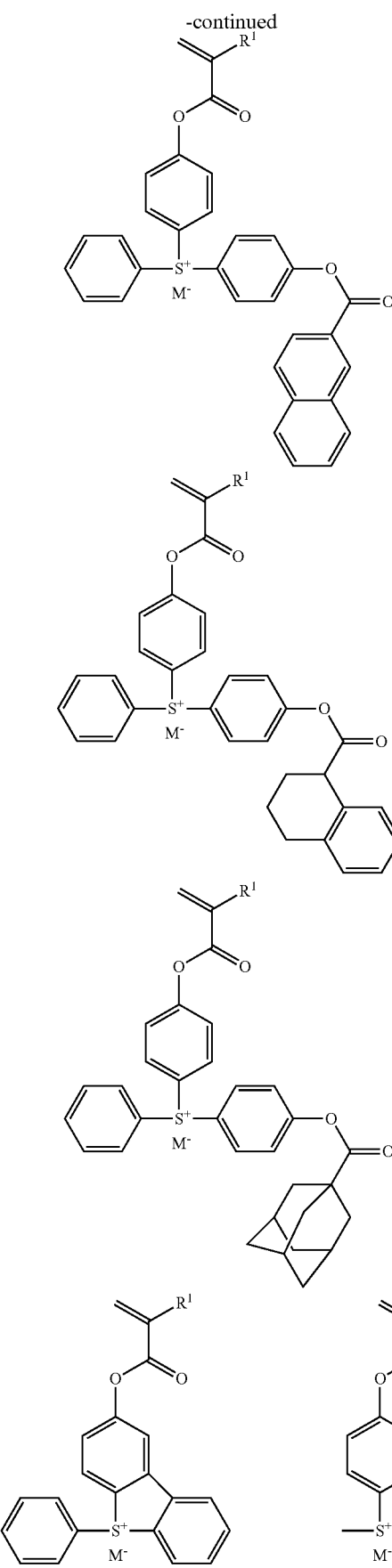
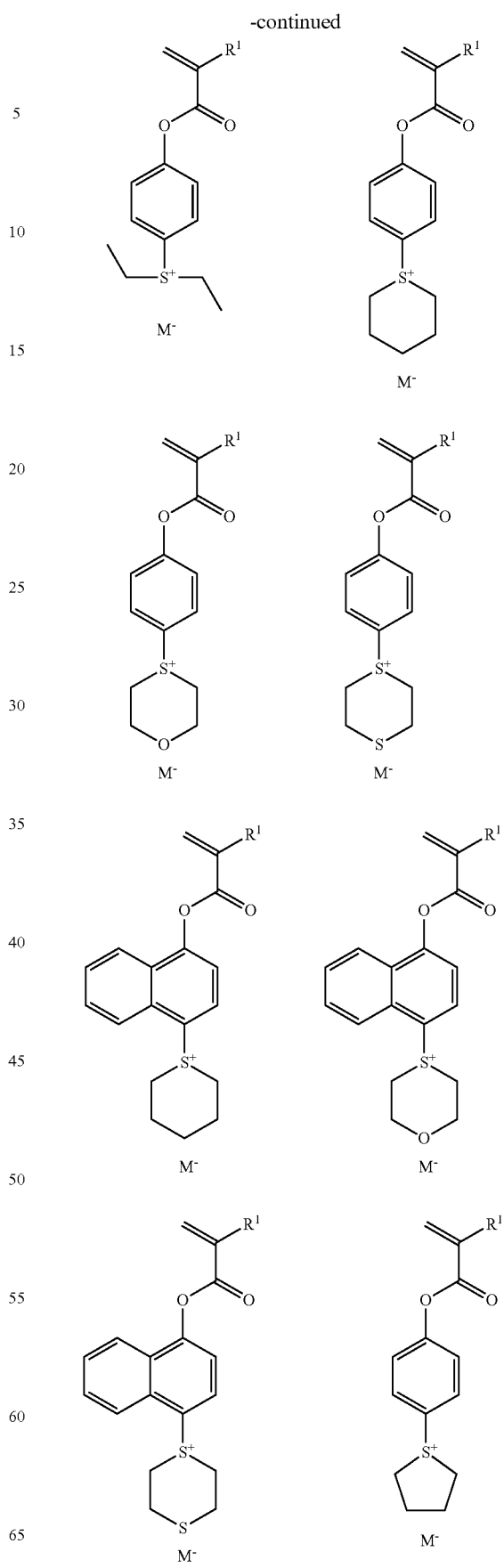

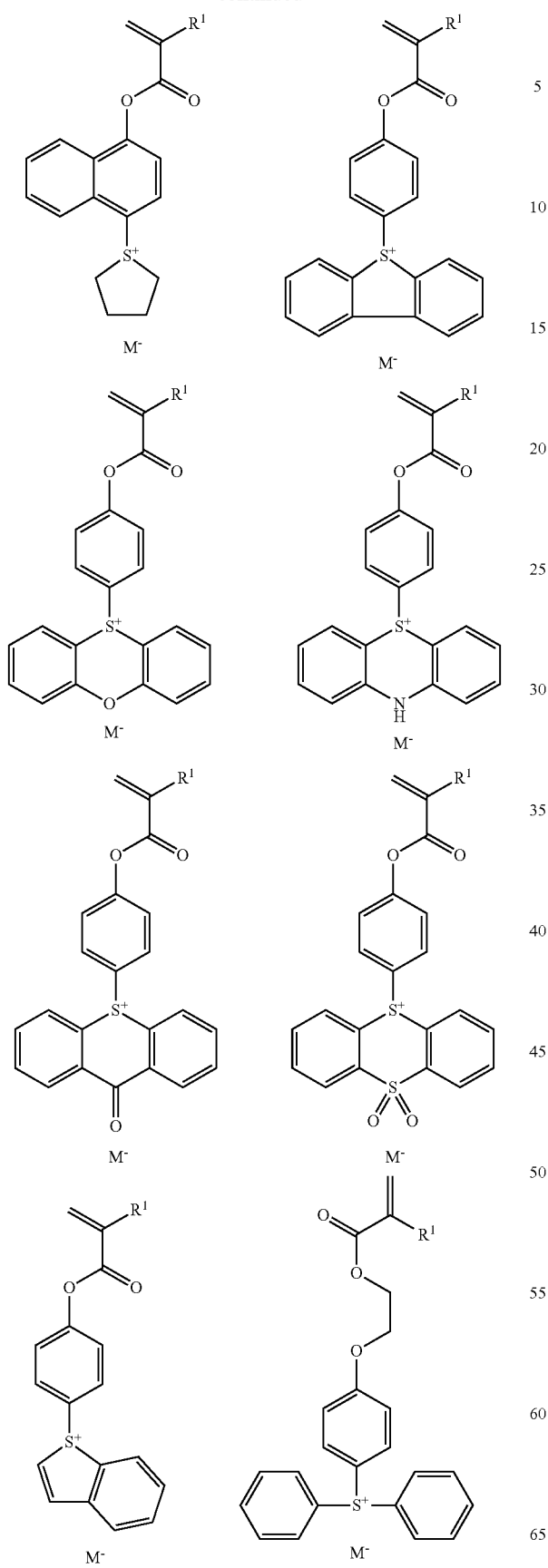

31
-continued
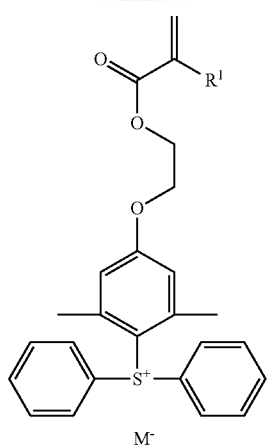
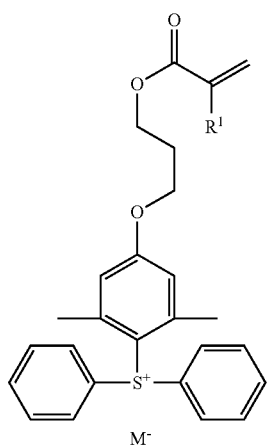
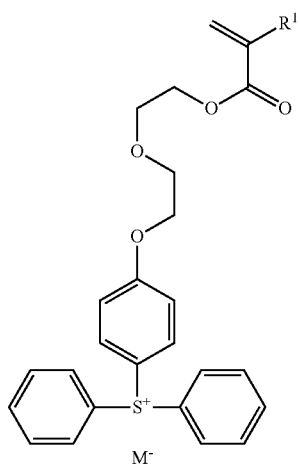
32
-continued
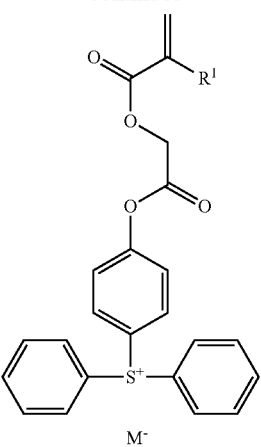
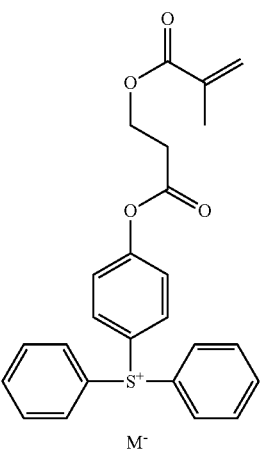
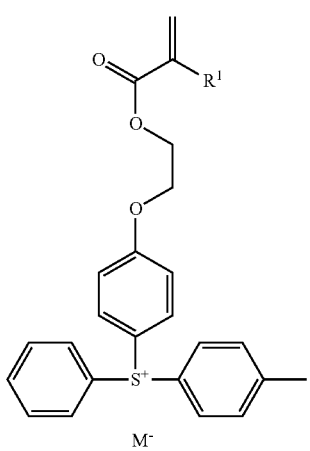

33
-continued
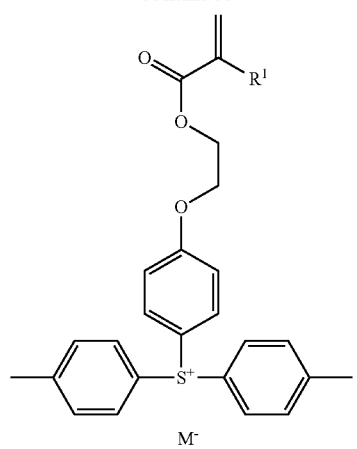
M⁻
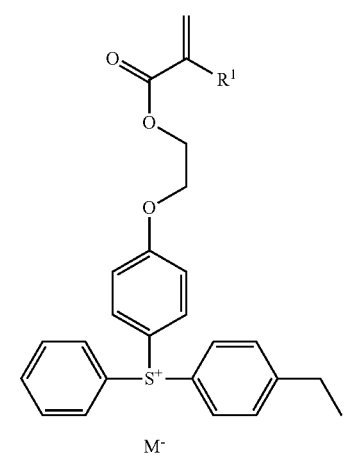
M⁻
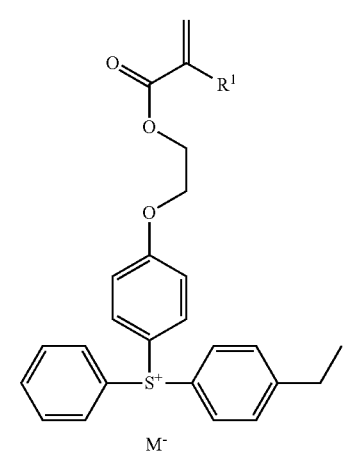
M⁻
34
-continued
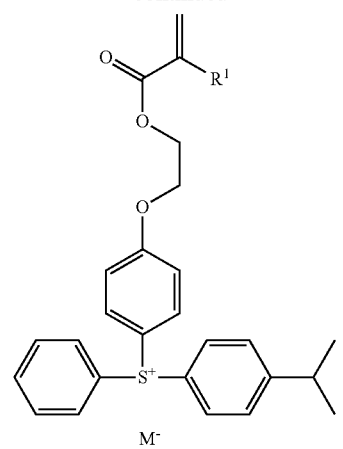
M⁻
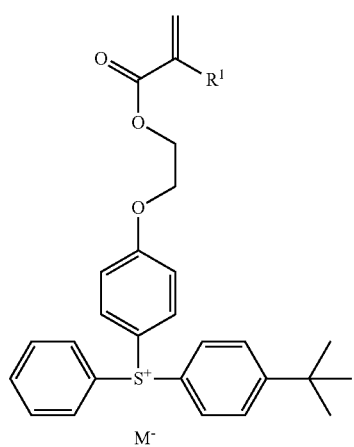
M⁻
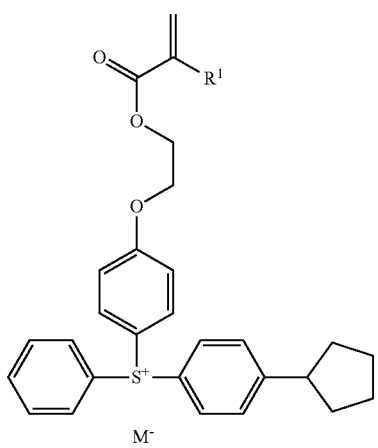
M⁻

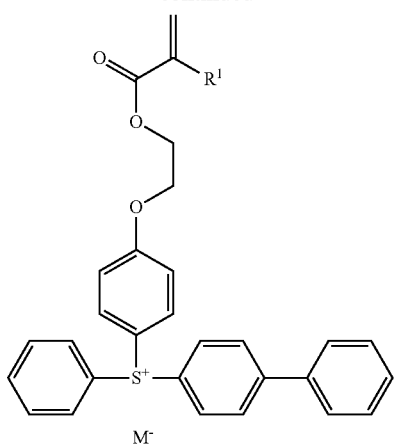
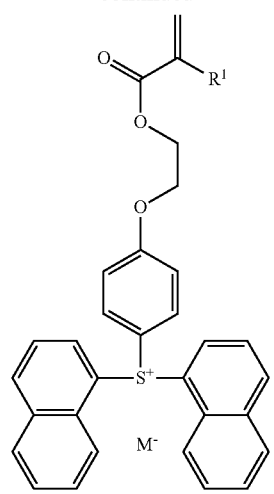
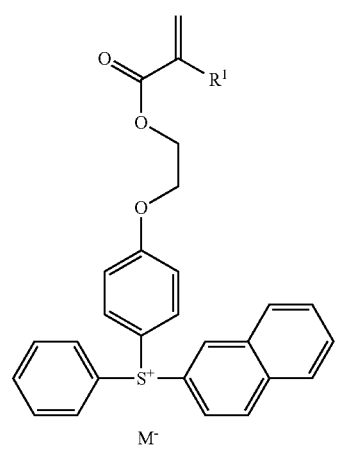
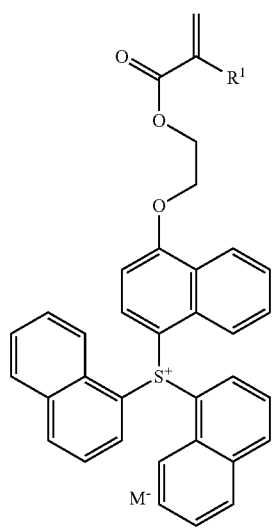
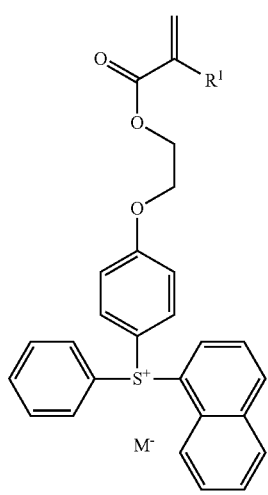
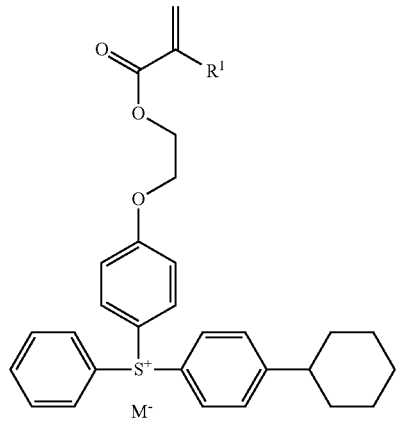

-continued
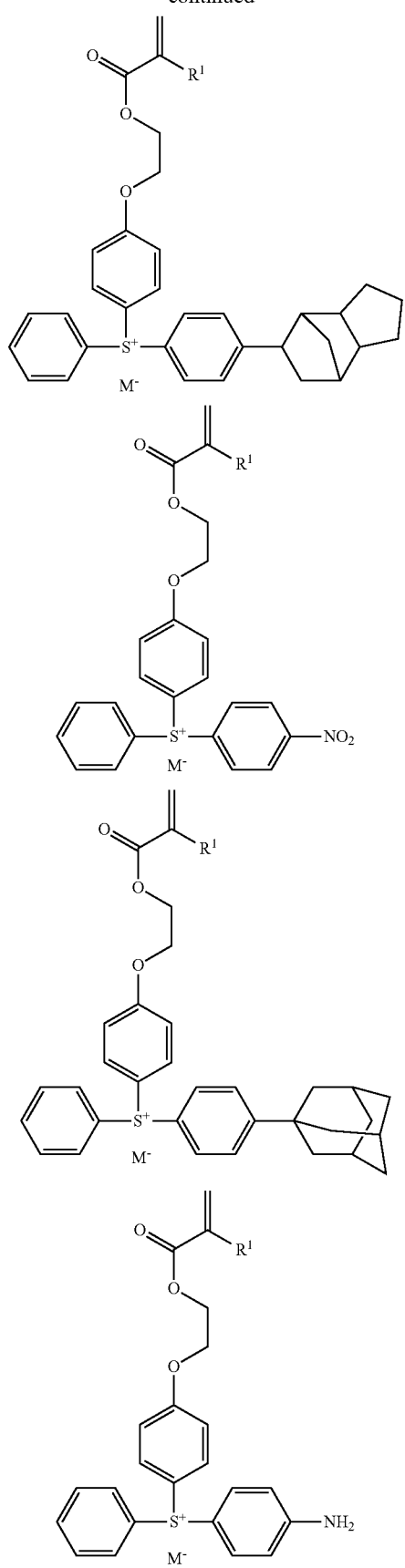
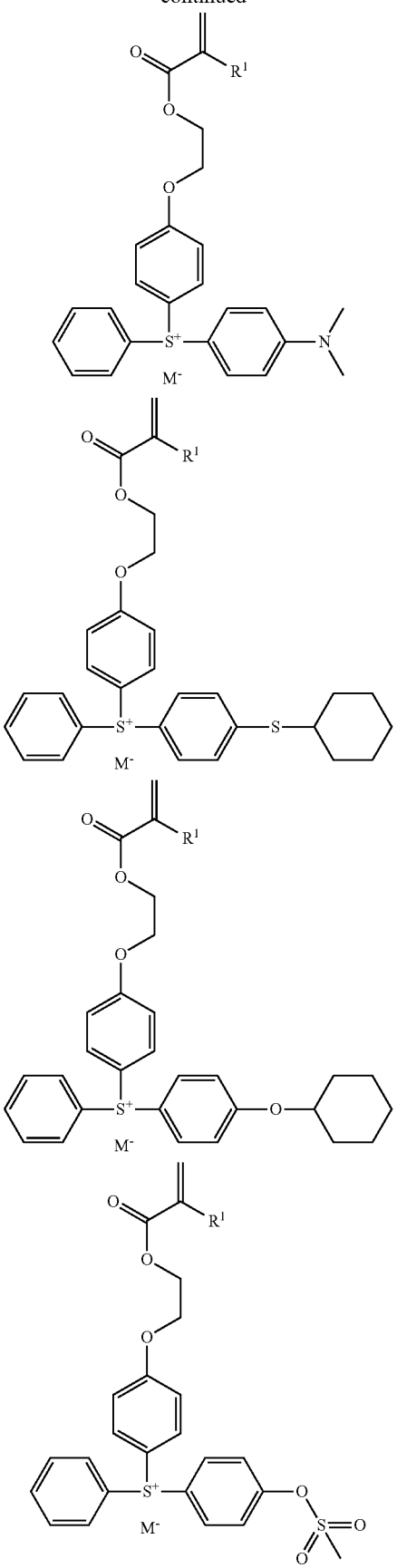

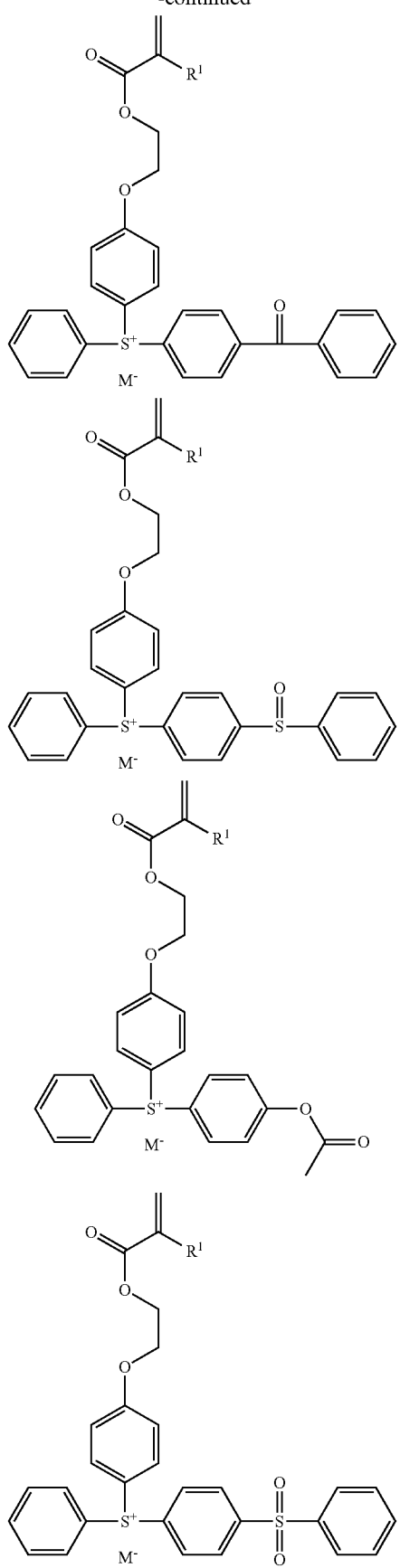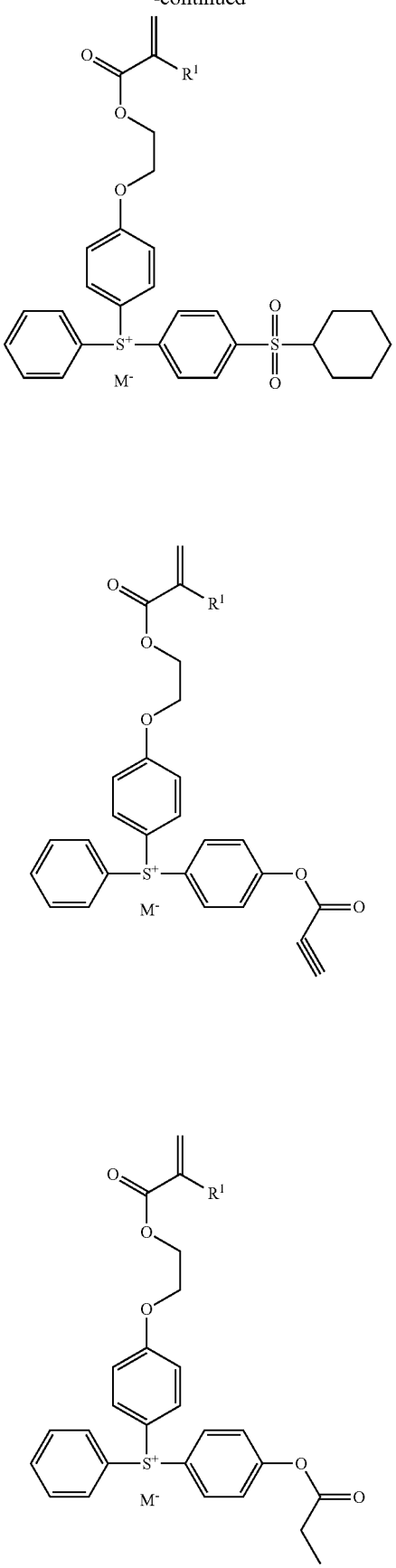

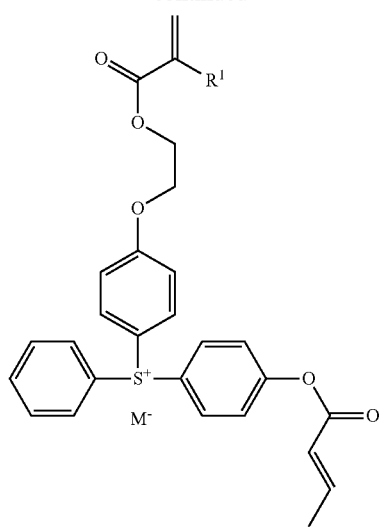
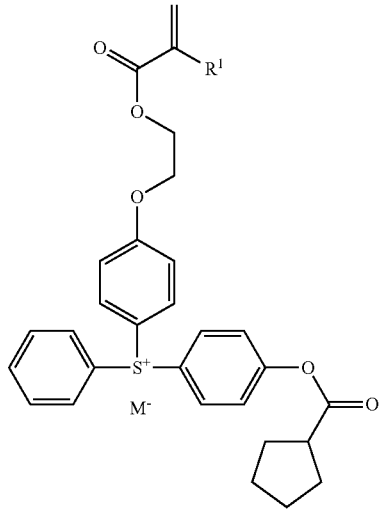
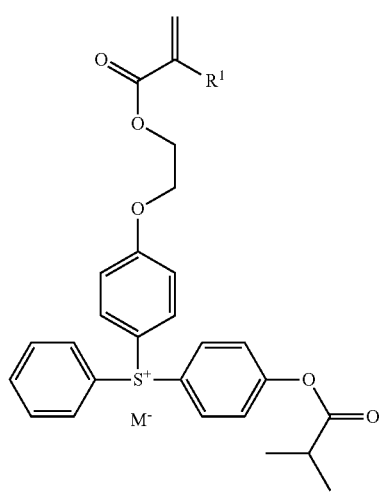
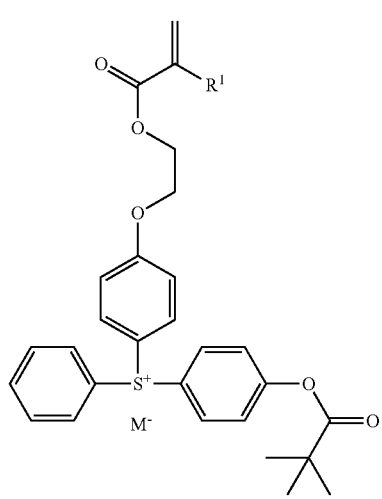
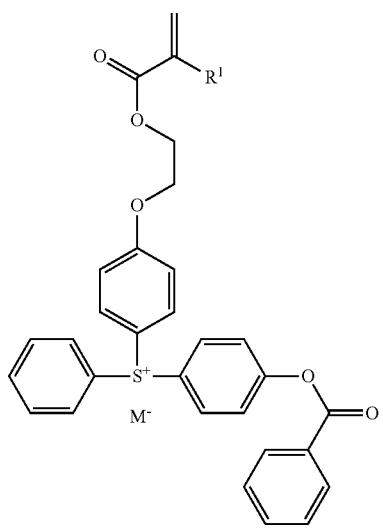

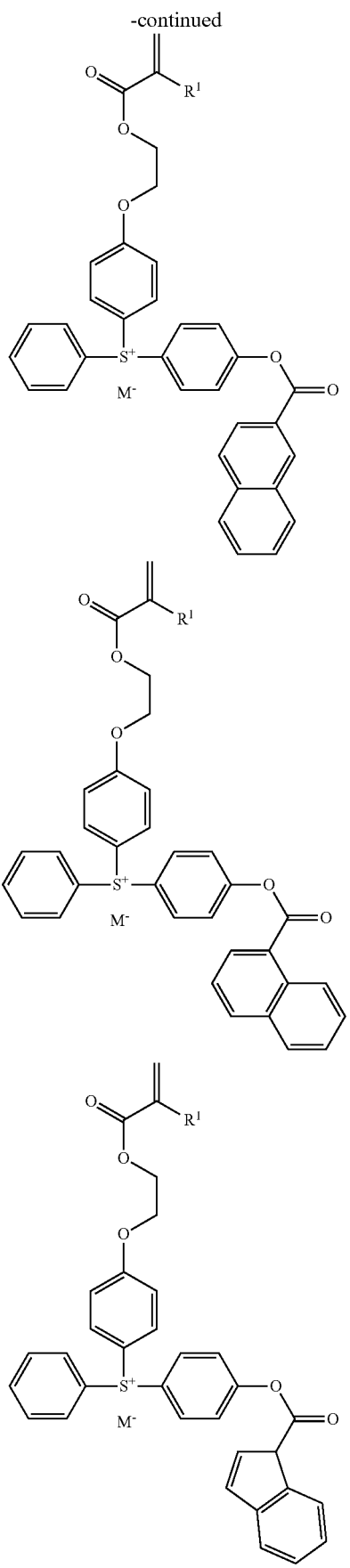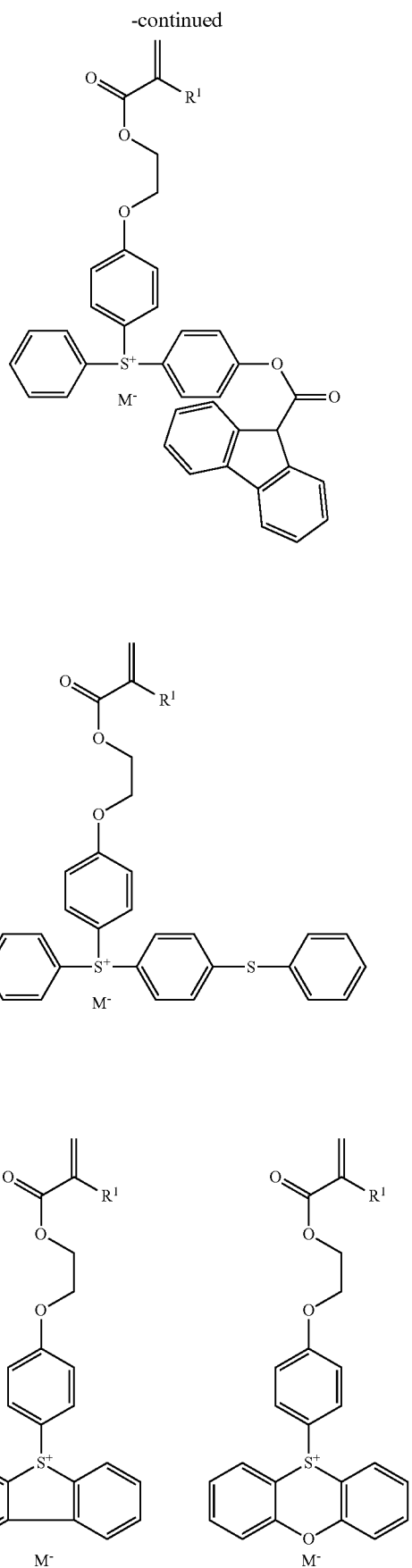

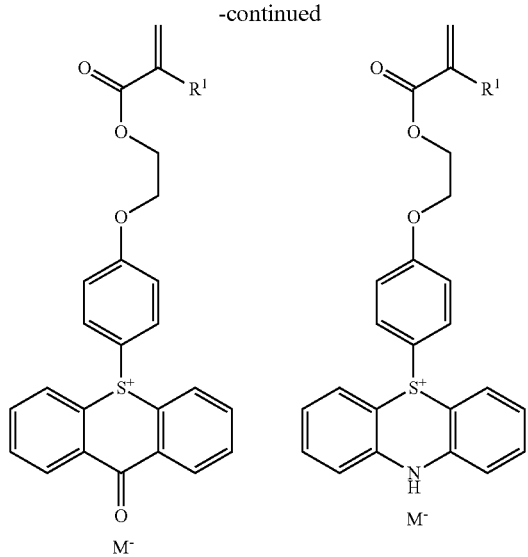
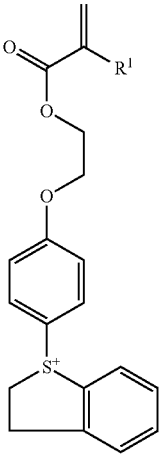
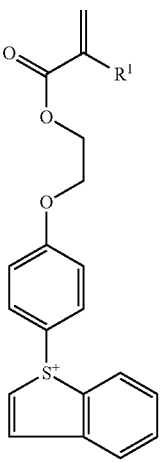
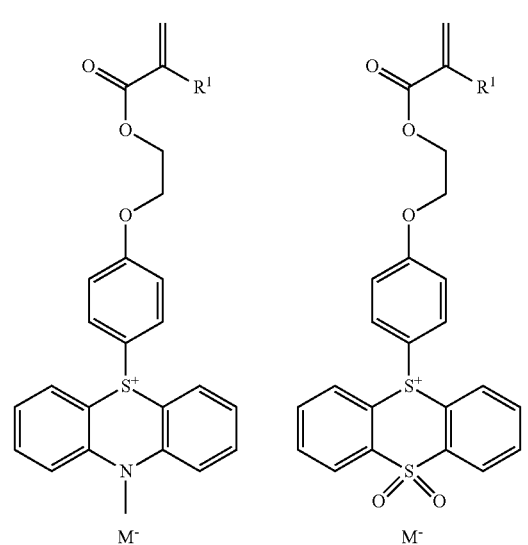
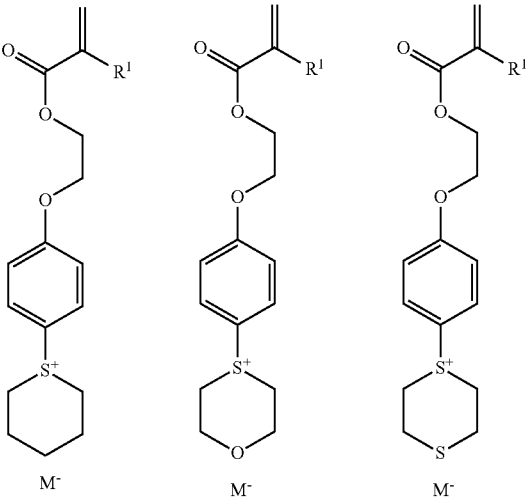
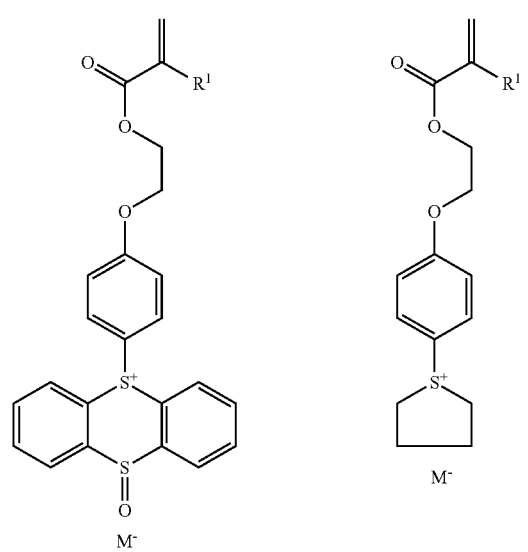
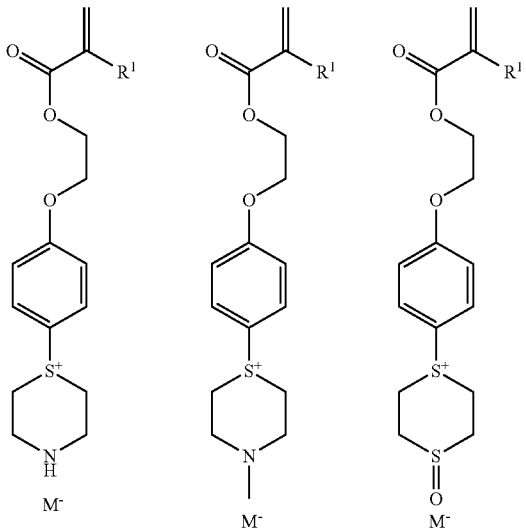

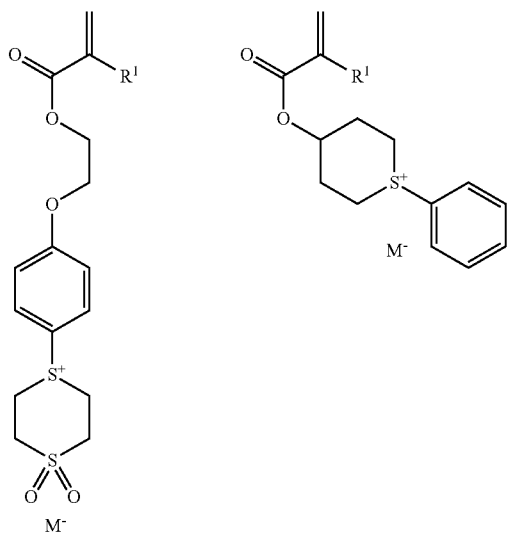
Examples of the monomer from which recurring unit (b) is derived are given below, but not limited thereto. Herein $R^7$ is as defined above.
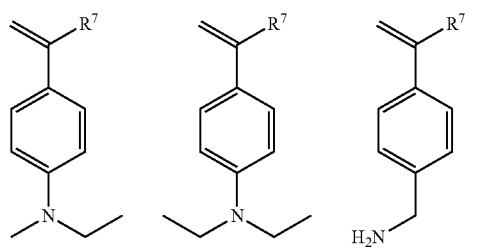
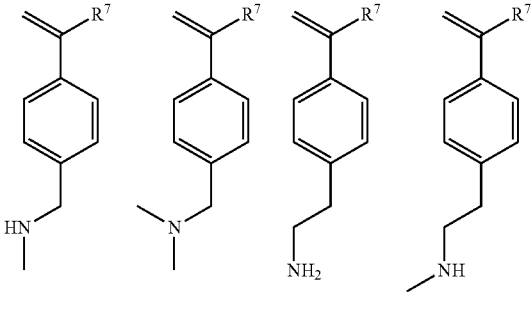
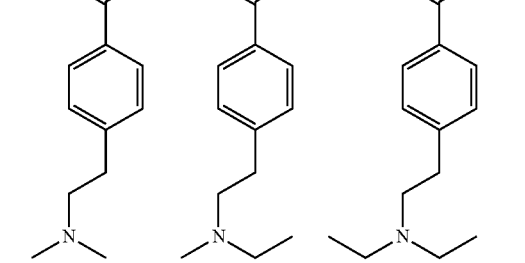
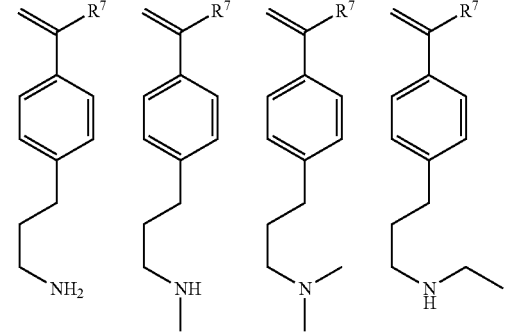
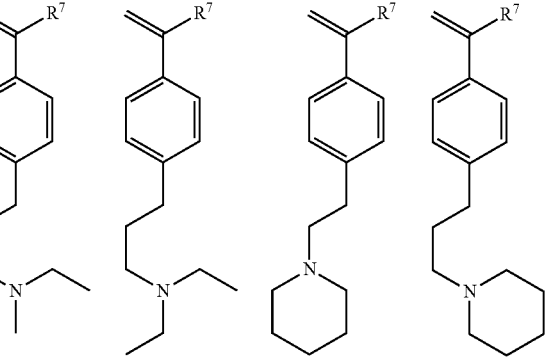

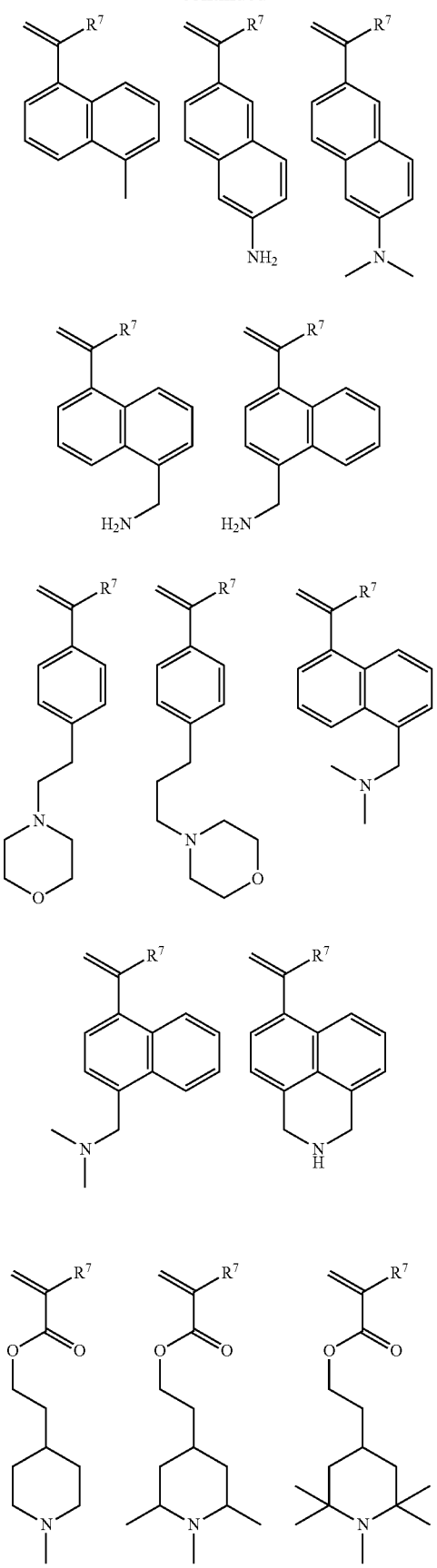
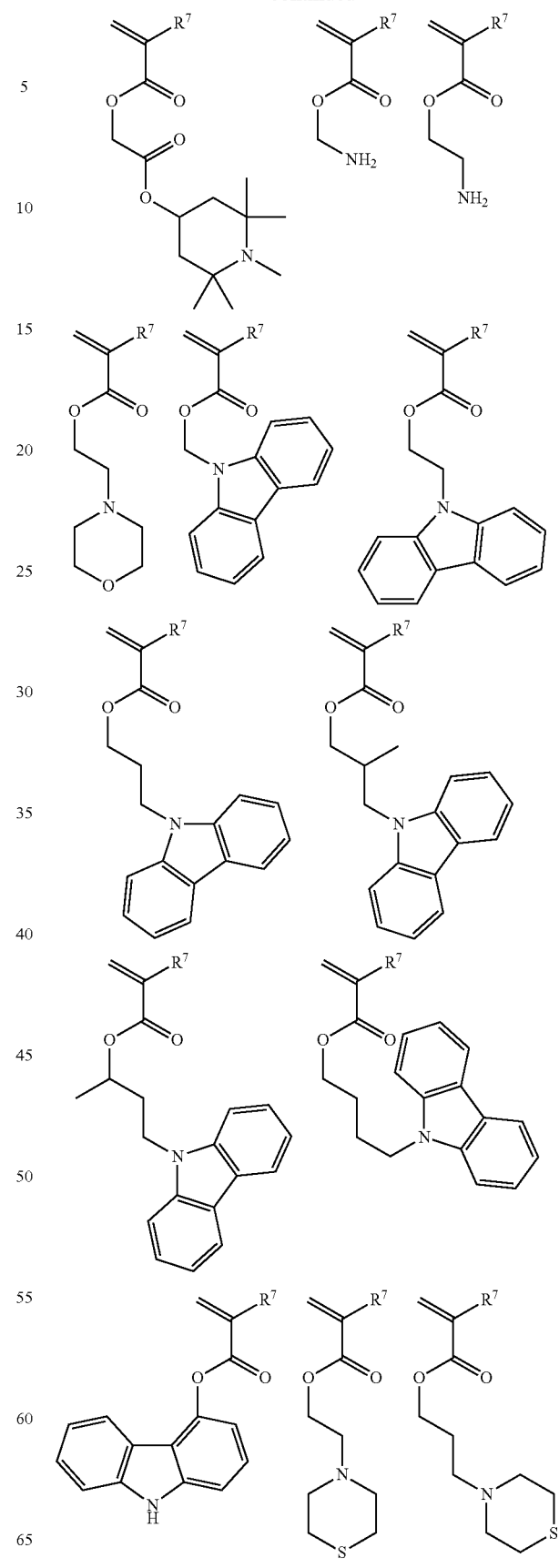

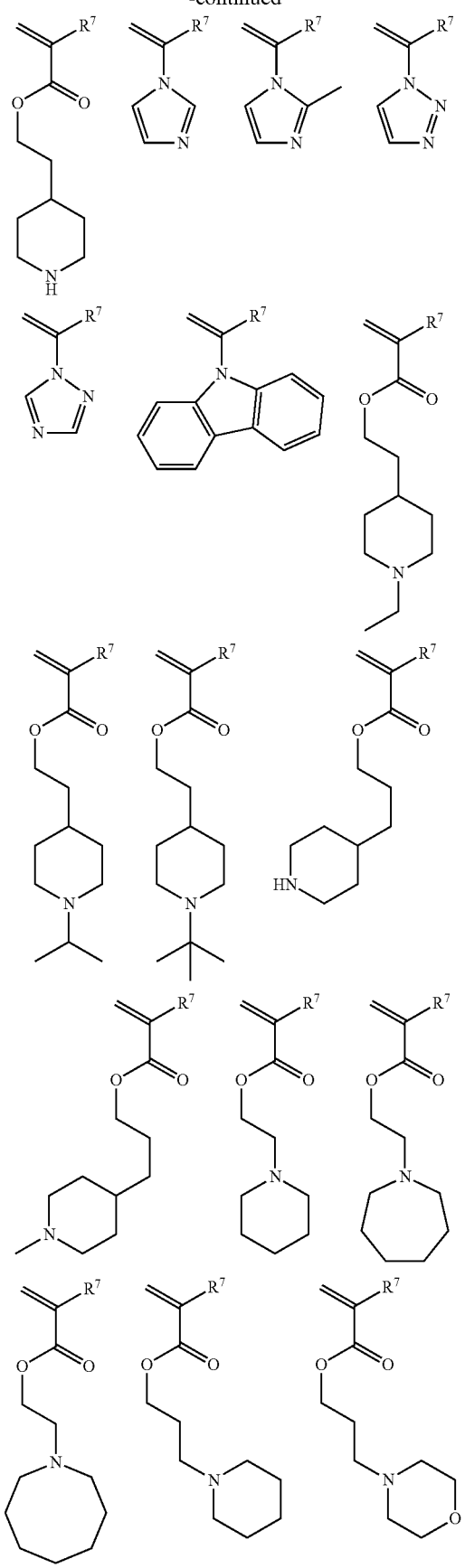
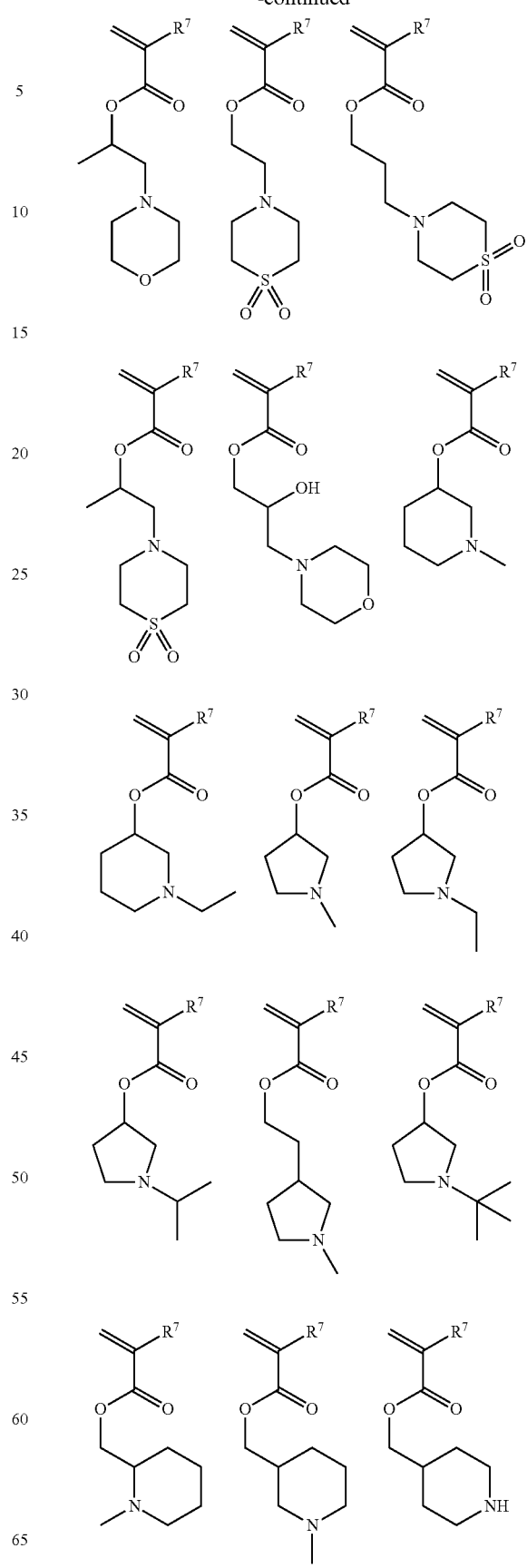

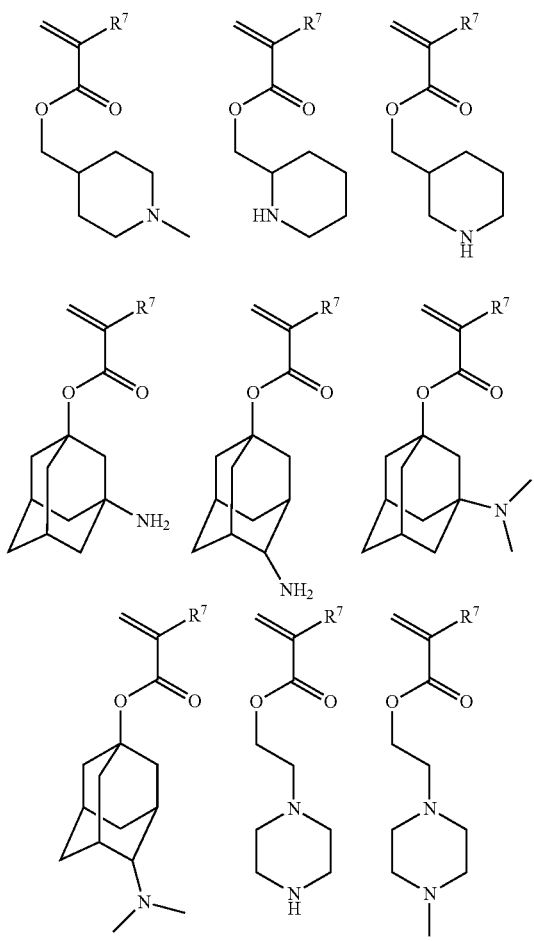

In formula (1), M⁻ is a non-nucleophilic counter ion containing at least one fluorine atom. Examples include fluoroalkylsulfonate ions such as triflate, 1,1,1-trifluoroethanesulfonate, and nonafluorobutanesulfonate; 2-fluorobenzenesulfonate, 3-fluorobenzenesulfonate, 4-fluorobenzenesulfonate, 4-trifluoromethylbenzenesulfonate, 1,2,3,4,5-pentafluorobenzenesulfonate, bis(trifluoromethylsulfonyl)imide, bis(perfluoroethylsulfonyl)imide, bis(perfluorobutylsulfonyl)imide, tris(trifluoromethylsulfonyl)methide, tris(perfluoroethylsulfonyl)methide, hexafluorophosphate, tetrafluoroborate, trifluoro(trifluoromethyl)borate, tetrakis(4-fluorophenyl)borate, tetrakis(pentafluorophenyl)borate, hexafluoroarsenate, and hexafluoroantimonate.

Also included in M⁻ are sulfonates having fluorine substituted at α-position as represented by the formula (K-1) and sulfonates having fluorine substituted at α- and β-positions as represented by the formula (K-2).

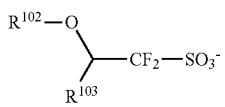

In formula (K-1), $R^{101}$ is hydrogen, or a $C_1$-$C_{30}$ straight, branched or cyclic alkyl group, $C_2$-$C_{30}$ straight, branched or cyclic acyl group, $C_2$-$C_{20}$ alkenyl group, $C_6$-$C_{20}$ aryl group, or $C_6$-$C_{20}$ aryloxy group, which may contain an ether, ester, carbonyl moiety, lactone ring, lactam ring, sultone ring, amino, sulfone, sulfonic acid ester, carbonate, hydroxyl, thiol, carboxyl, carbamate, amide or imide moiety.

In formula (K-2), $R^{102}$ is hydrogen, or a $C_1$-$C_{30}$ straight, branched or cyclic alkyl group, $C_2$-$C_{30}$ straight, branched or cyclic acyl group, $C_2$-$C_{20}$ alkenyl group, $C_6$-$C_{20}$ aryl group or $C_6$-$C_{20}$ aryloxy group, which may contain an ether, ester, carbonyl moiety, lactone ring, lactam ring, sultone ring, amino, sulfone, sulfonic acid ester, carbonate, hydroxyl, thiol, carboxyl, carbamate, amide or imide moiety. $R^{103}$ is hydrogen, methyl, ethyl or trifluoromethyl.

The polymer does not contain recurring units adapted to increase a polarity by deprotection reaction with the aid of acid. The recurring units adapted to increase a polarity by deprotection reaction with the aid of acid are typically recurring units containing a so-called acid labile group. Examples of the recurring units containing an acid labile group include recurring units containing a carboxyl group substituted with an acid labile group and recurring units containing a phenolic hydroxyl group substituted with an acid labile group. Since the polymer does not contain these recurring units, the inventive resist composition is a non-chemically-amplified resist composition.

The polymer may further comprise recurring units (a) containing a phenolic hydroxyl group, preferably recurring units (c) having the formula (3).

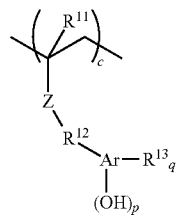

(3)

Herein Ar is a $C_6$-$C_{14}$ aromatic group which may contain a nitrogen atom. $R^{11}$ is hydrogen or methyl. $R^{12}$ is a single bond or a $C_1$-$C_{10}$ straight or branched alkylene group which may contain a hydroxyl, carboxyl, ester, ether moiety or lactone ring. $R^{13}$ is hydrogen, fluorine, a trifluoromethyl group, cyano group, $C_1$-$C_{10}$ straight, branched or cyclic alkyl group, $C_1$-$C_{10}$ straight, branched or cyclic alkoxy group, $C_6$-$C_{14}$ aryl group, $C_2$-$C_{10}$ straight, branched or cyclic alkenyl group, $C_2$-$C_{10}$ straight, branched or cyclic alkynyl group, $C_2$-$C_{10}$ straight, branched or cyclic alkoxycarbonyl group, $C_2$-$C_{10}$ straight, branched or cyclic acyl group, or $C_2$-$C_{10}$ straight, branched or cyclic acyloxy group. Z is a single bond, —C(=O)—O— or —C(=O)—NH—, p is an integer of 1 to 5, and q is an integer of 0 to 4.

Examples of the monomer from which recurring unit (c) is derived are given below, but not limited thereto. Herein $R^{11}$ is as defined above.

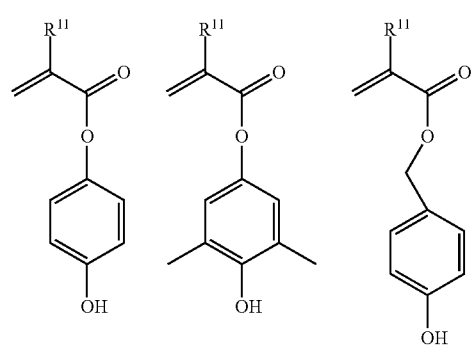
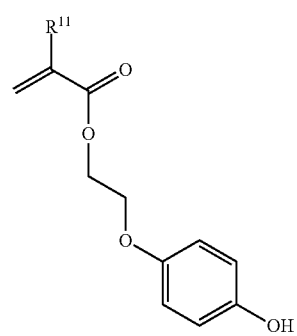
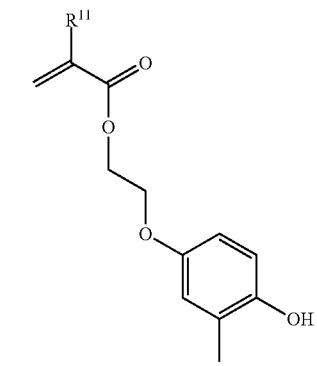
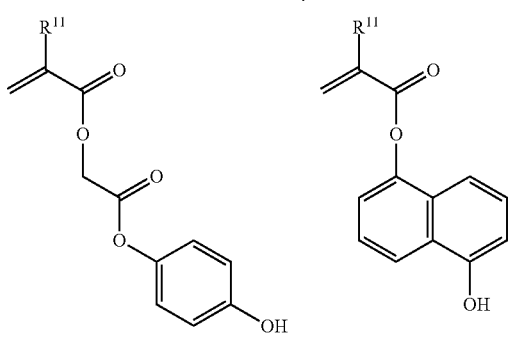
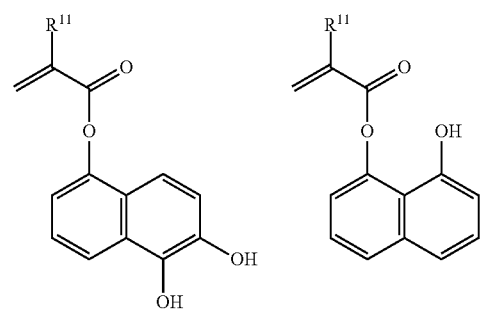
-continued
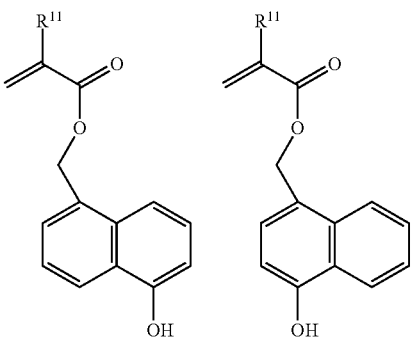
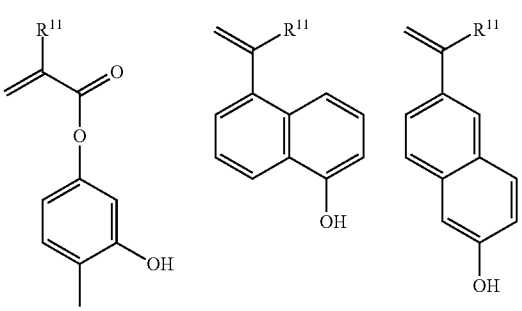
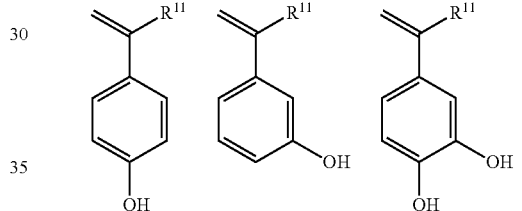
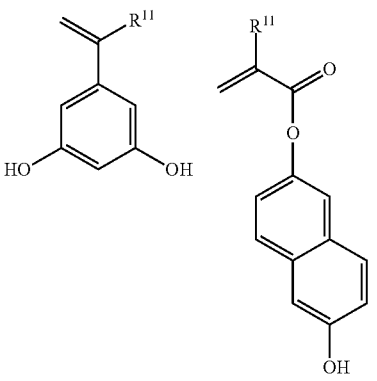
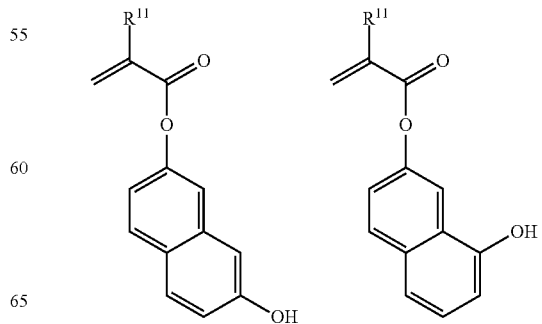

-continued
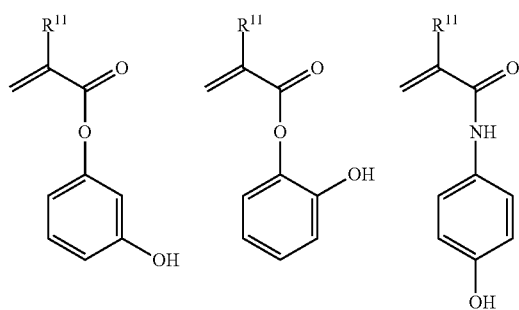
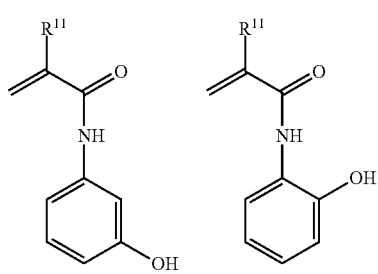
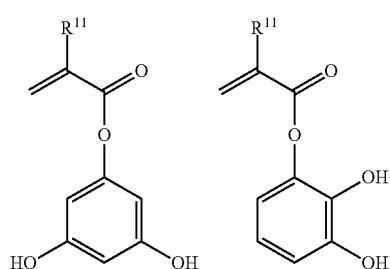
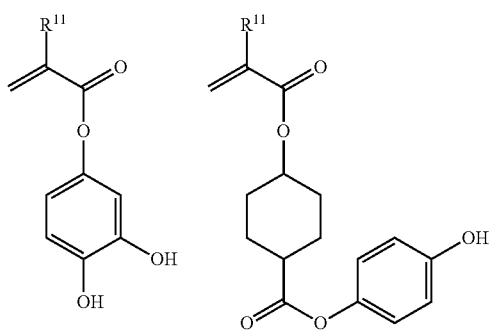
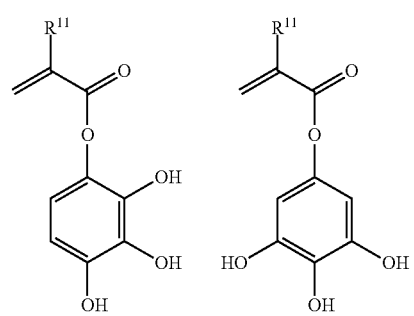
-continued
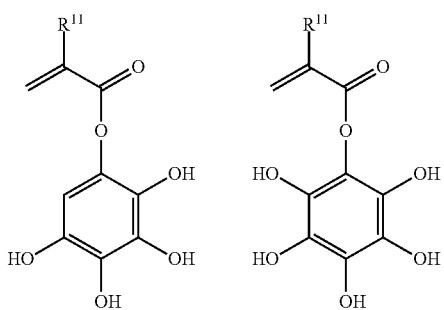
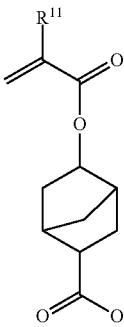
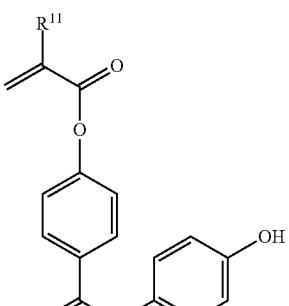
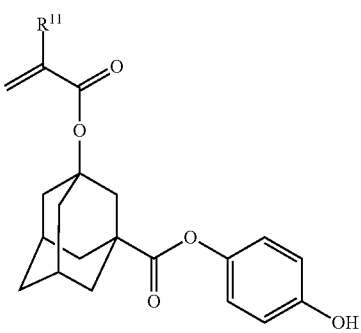
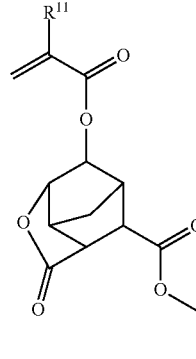

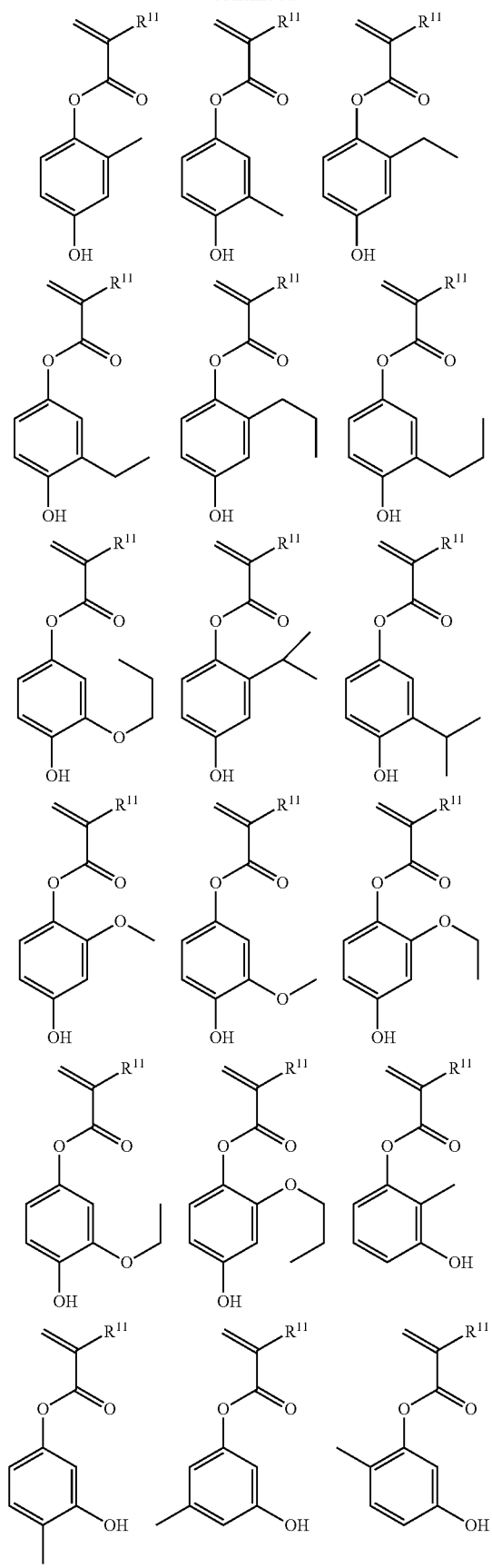
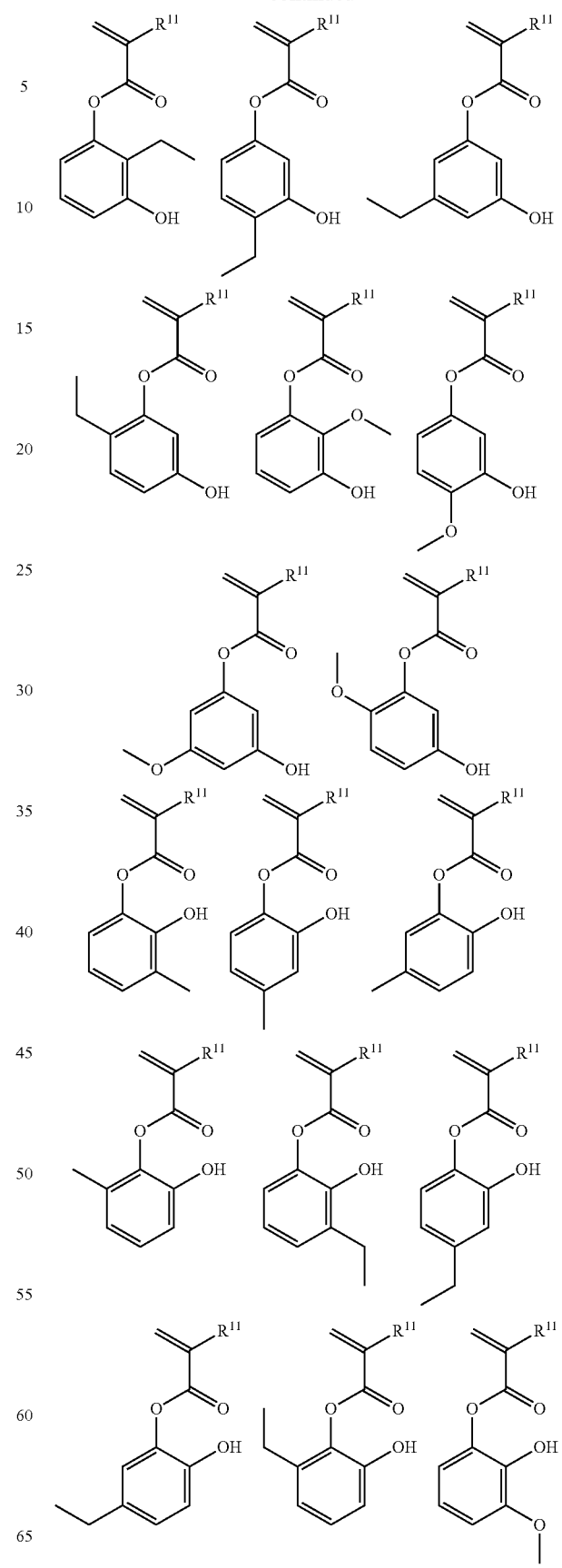

61
-continued
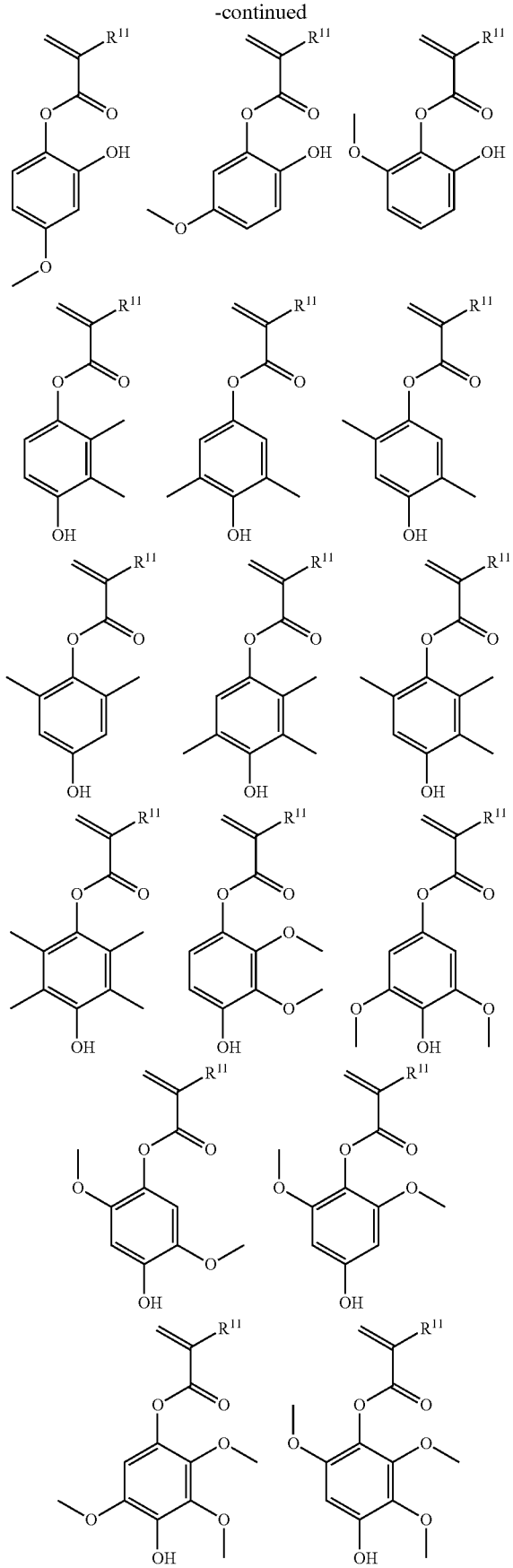
62
-continued
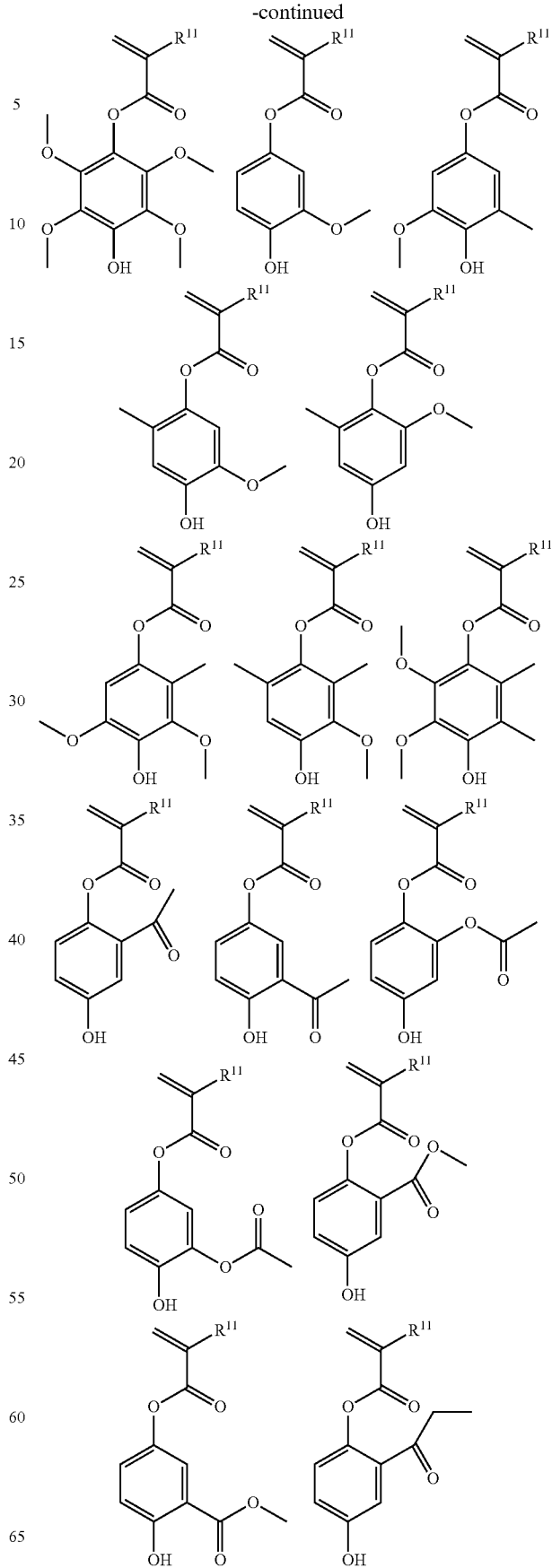

-continued
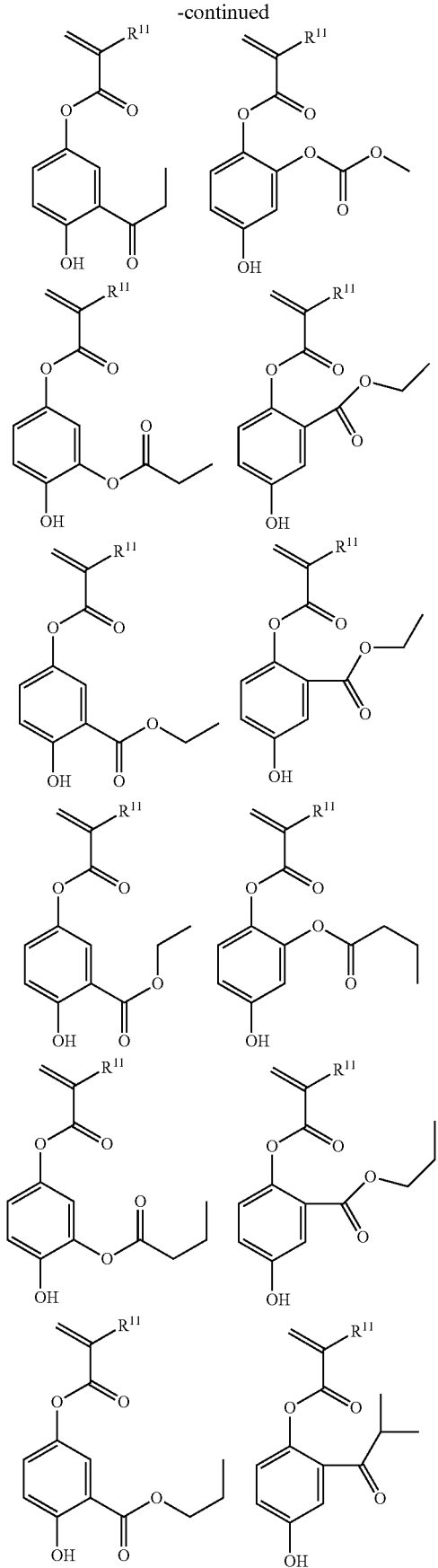
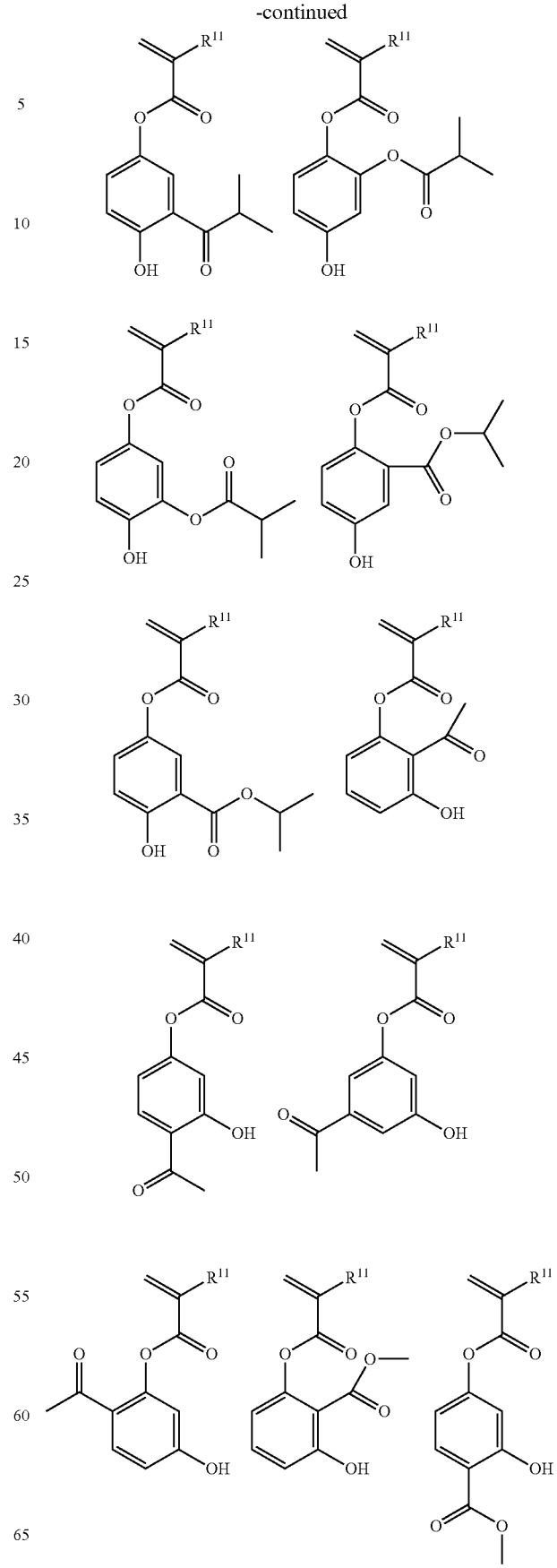

-continued
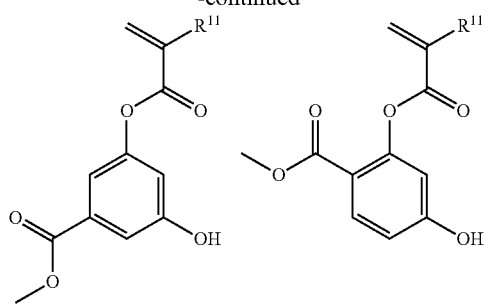
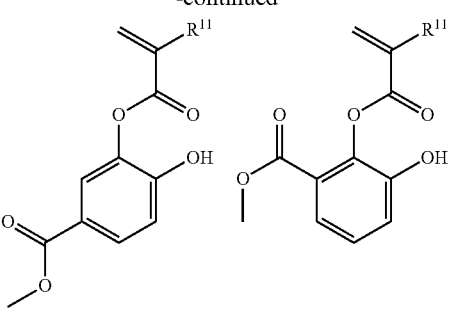
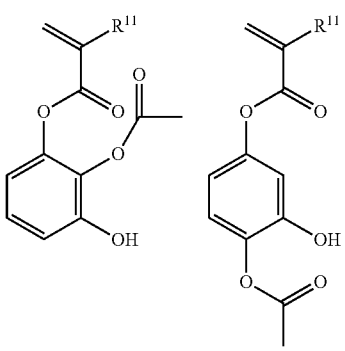
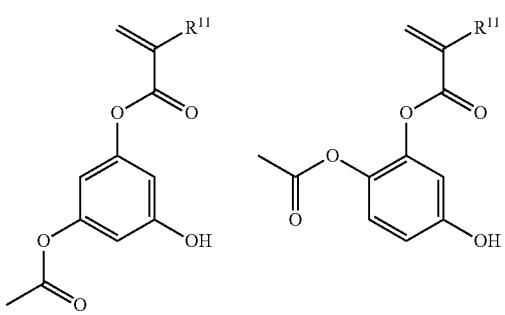
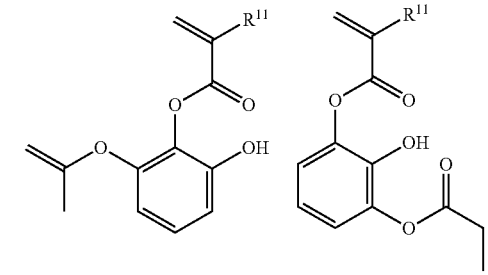
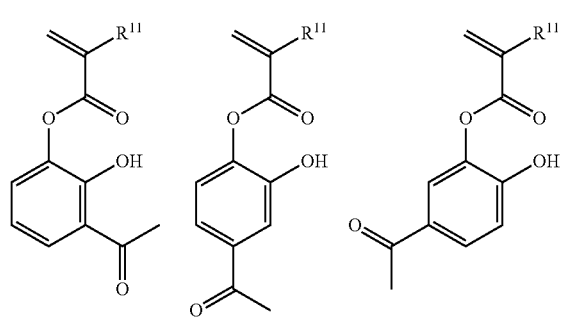
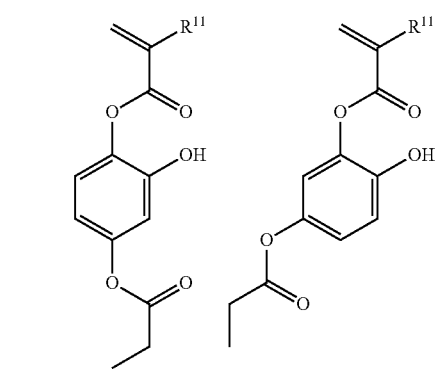
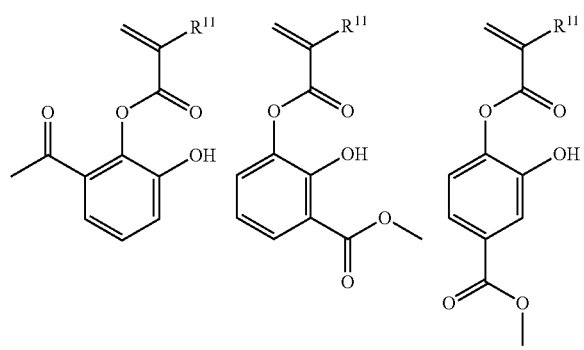
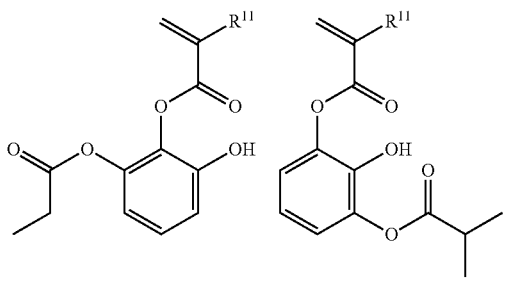

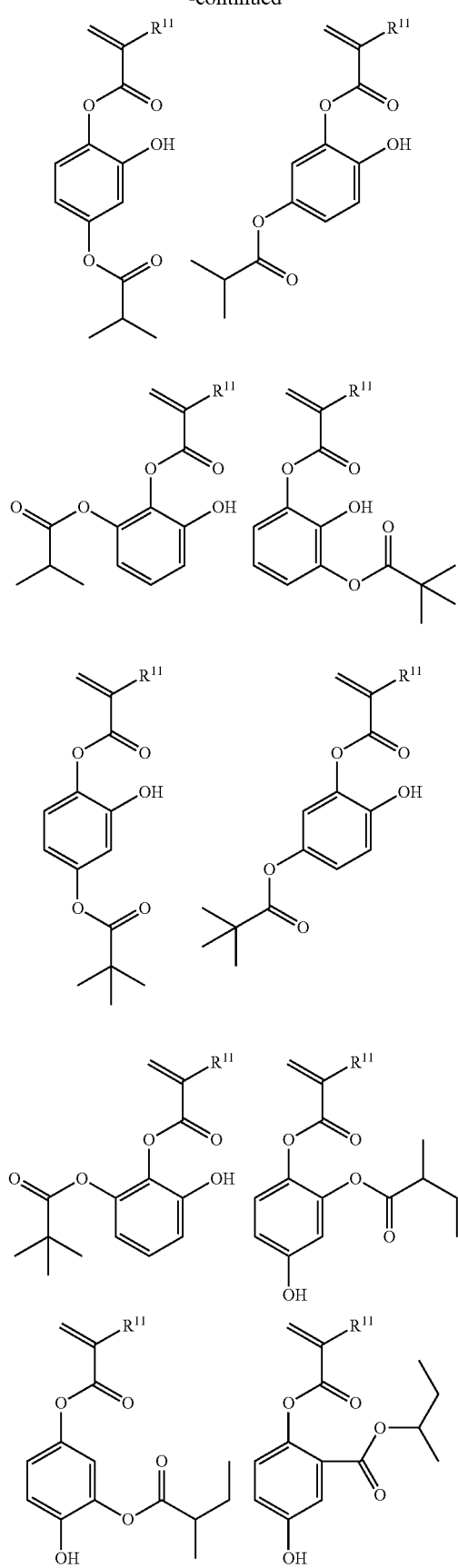
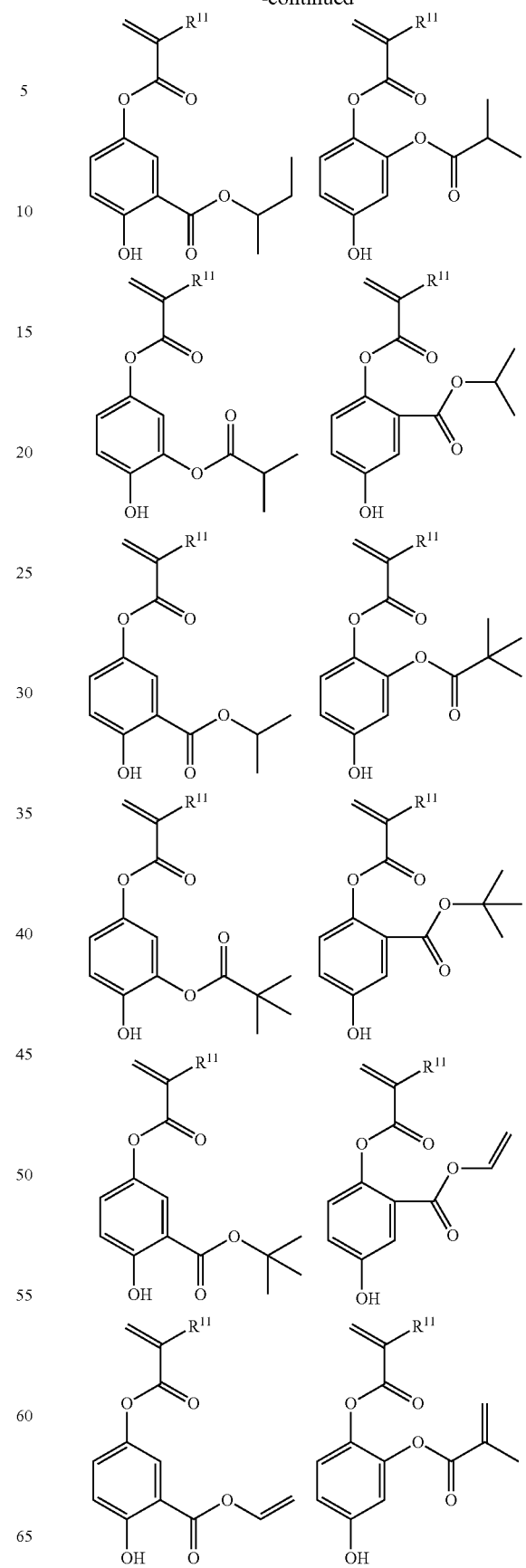

-continued
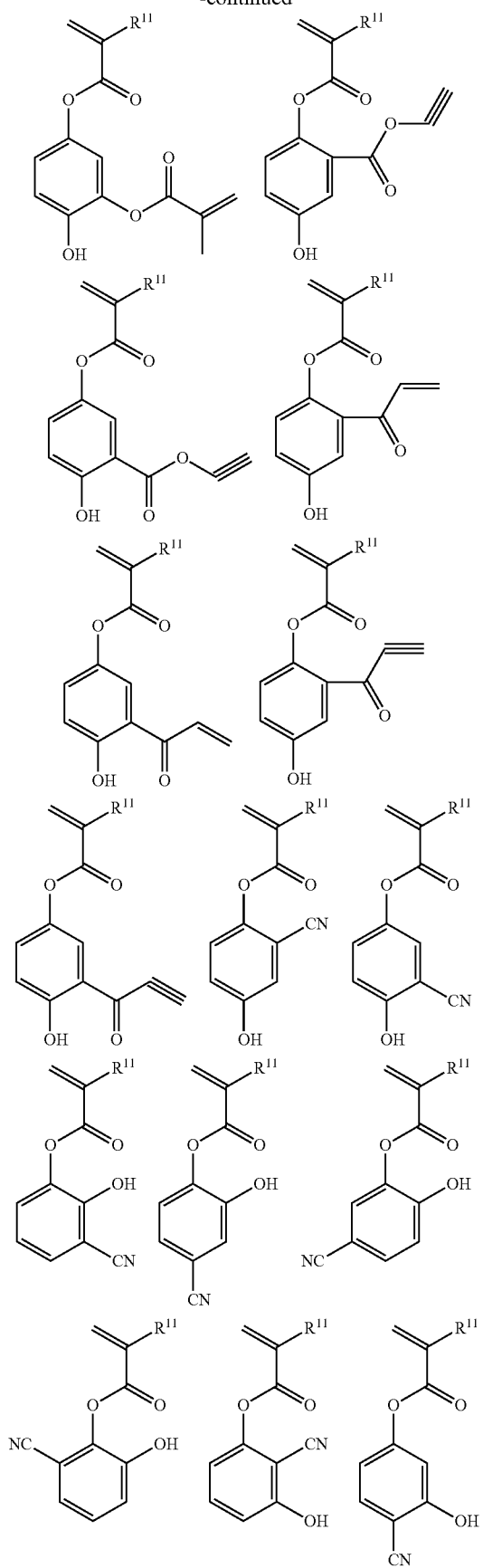
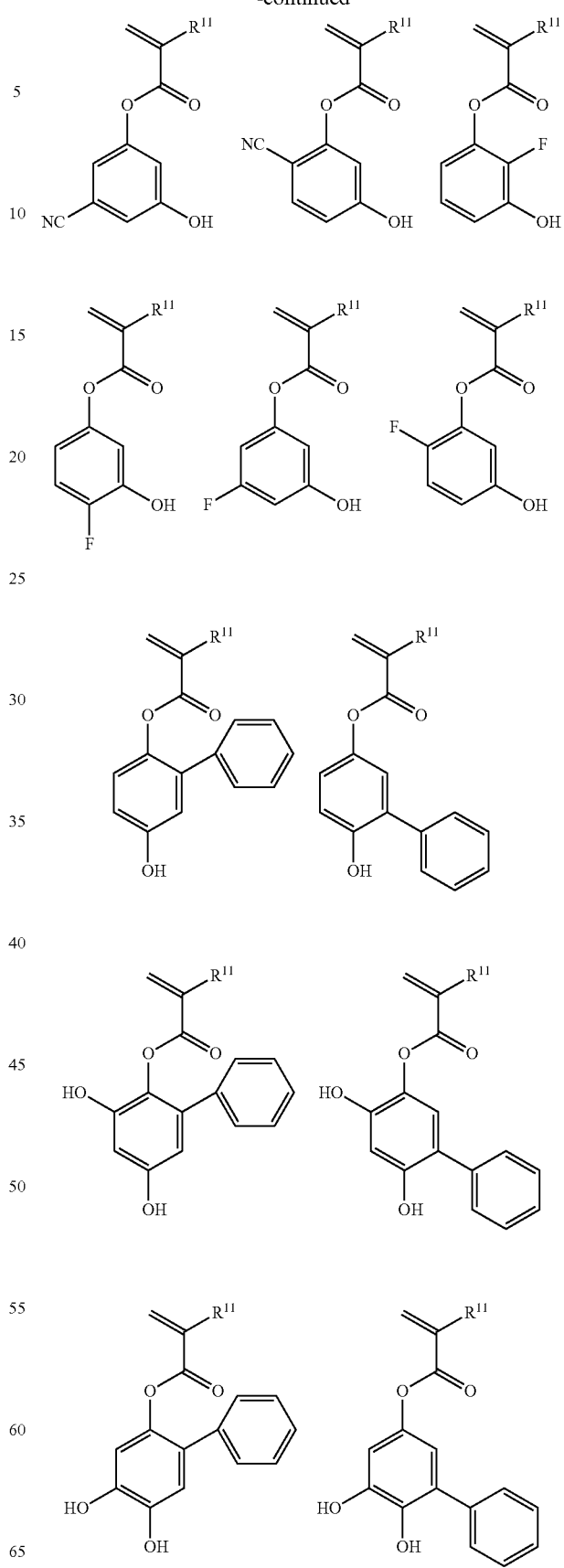

71
-continued
72
-continued
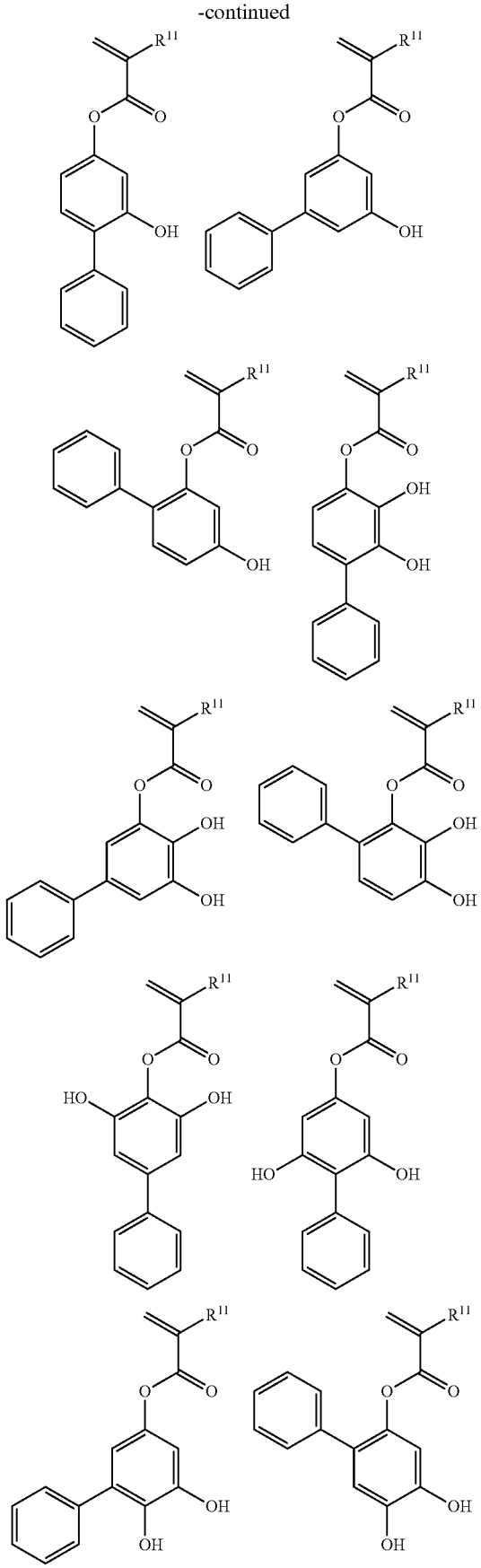
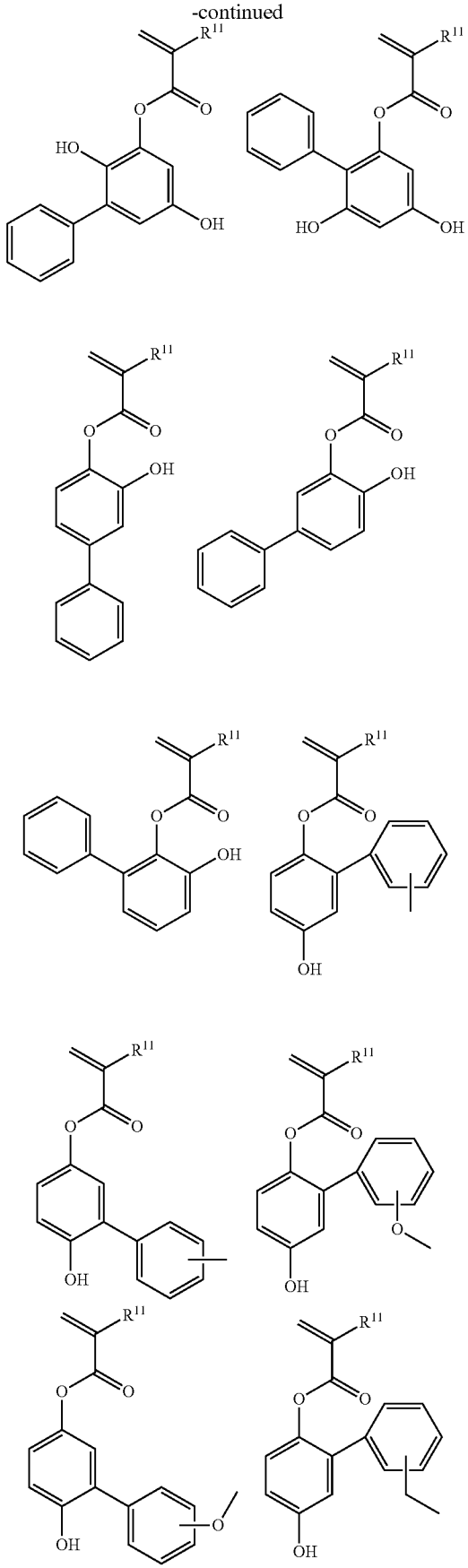

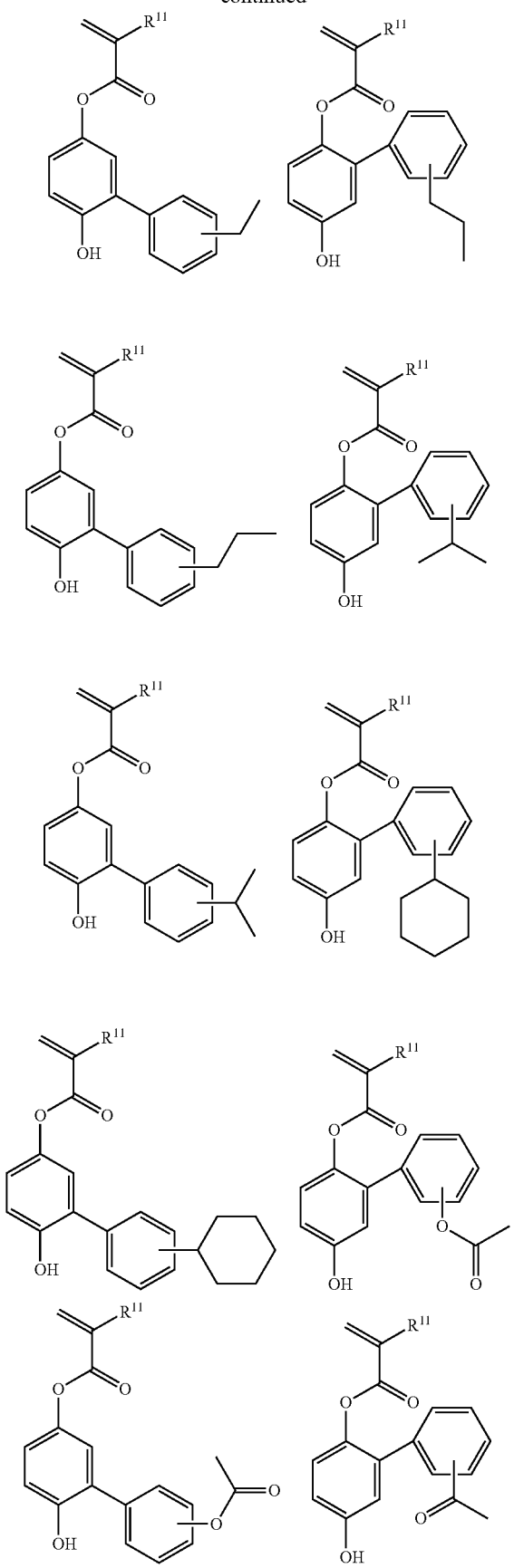
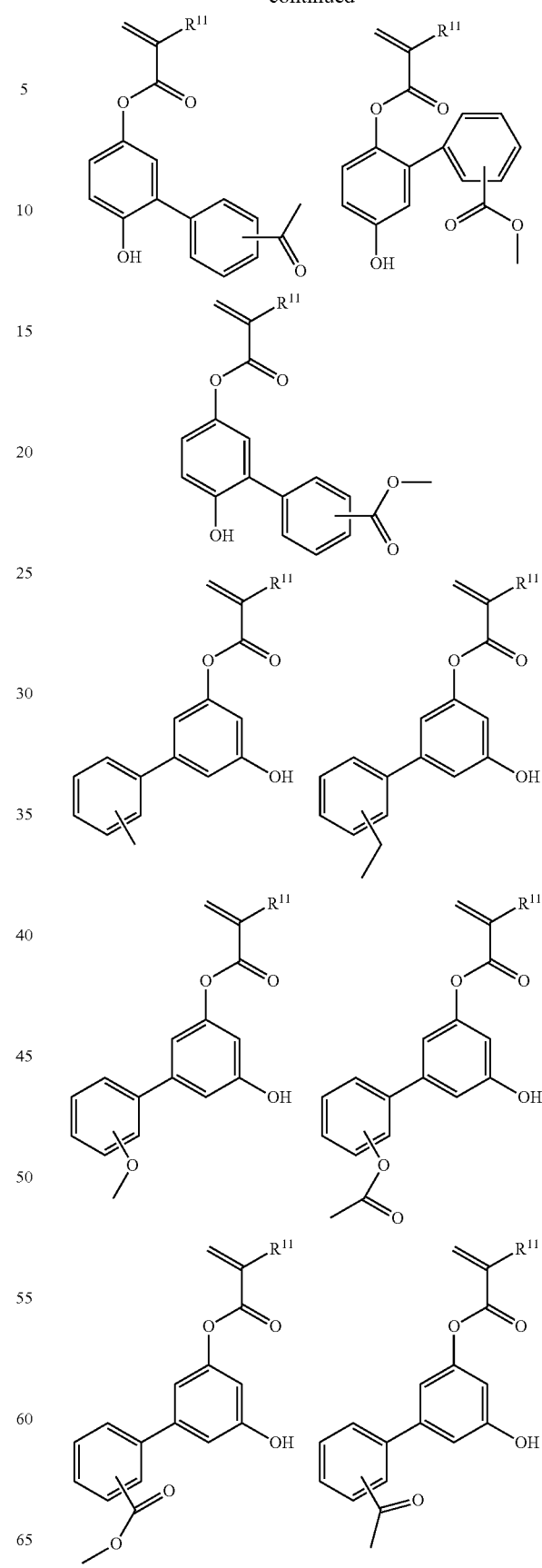

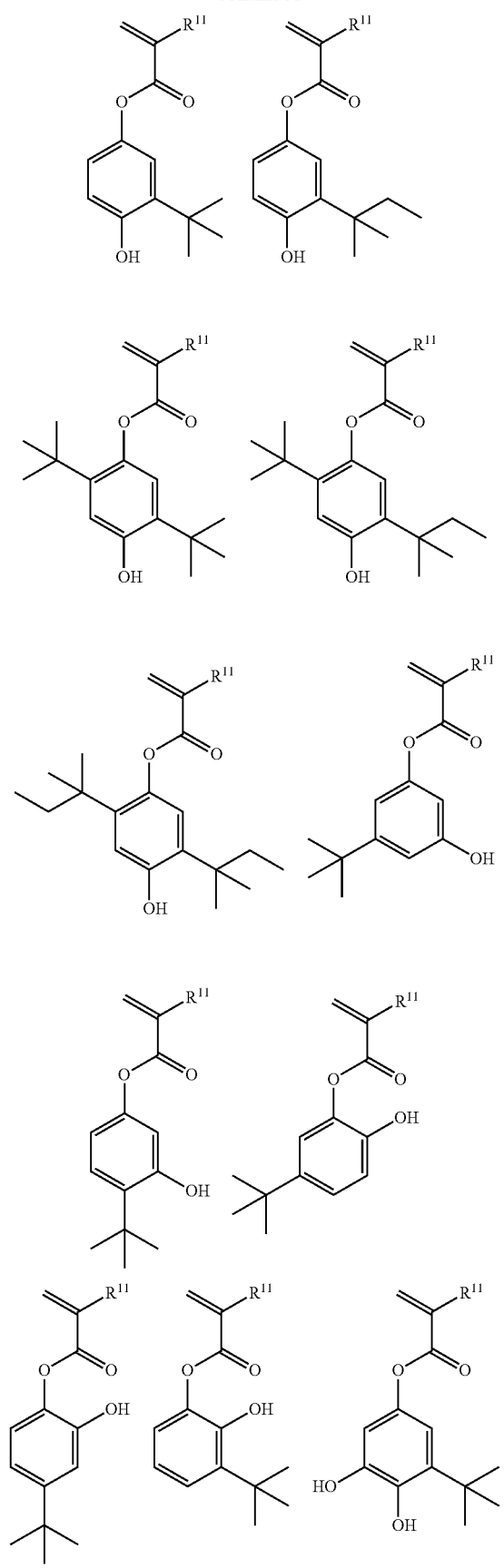
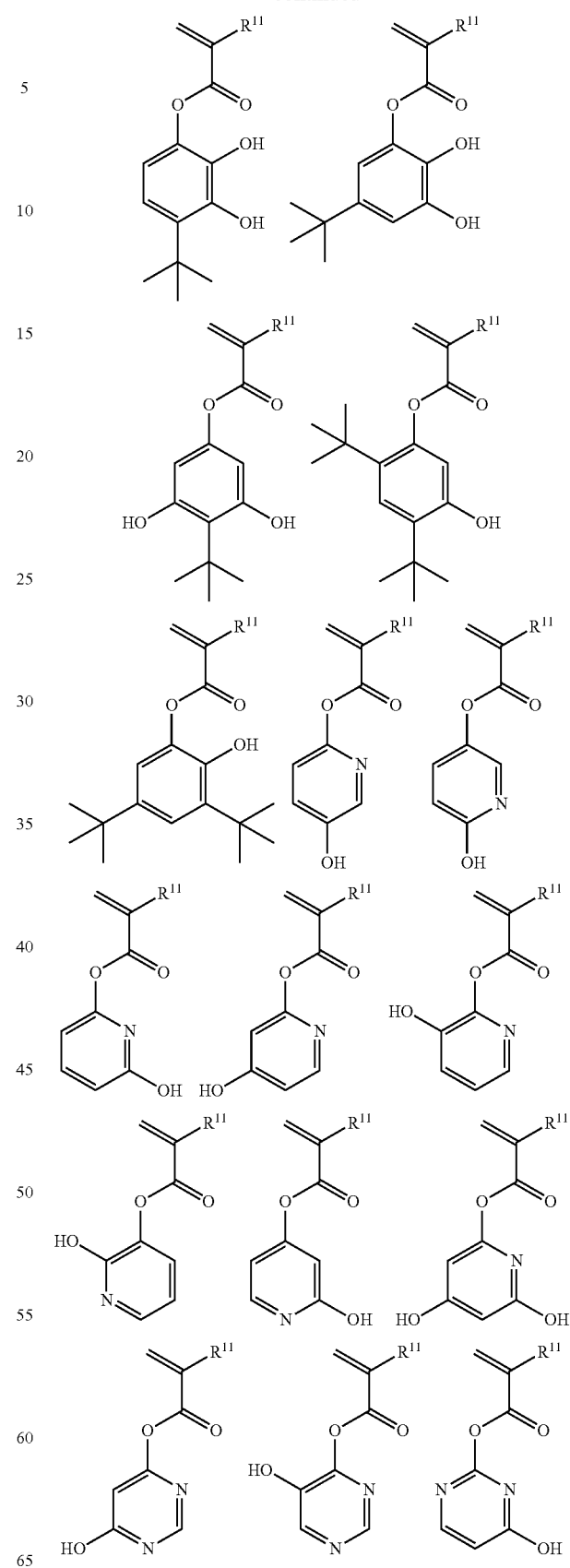

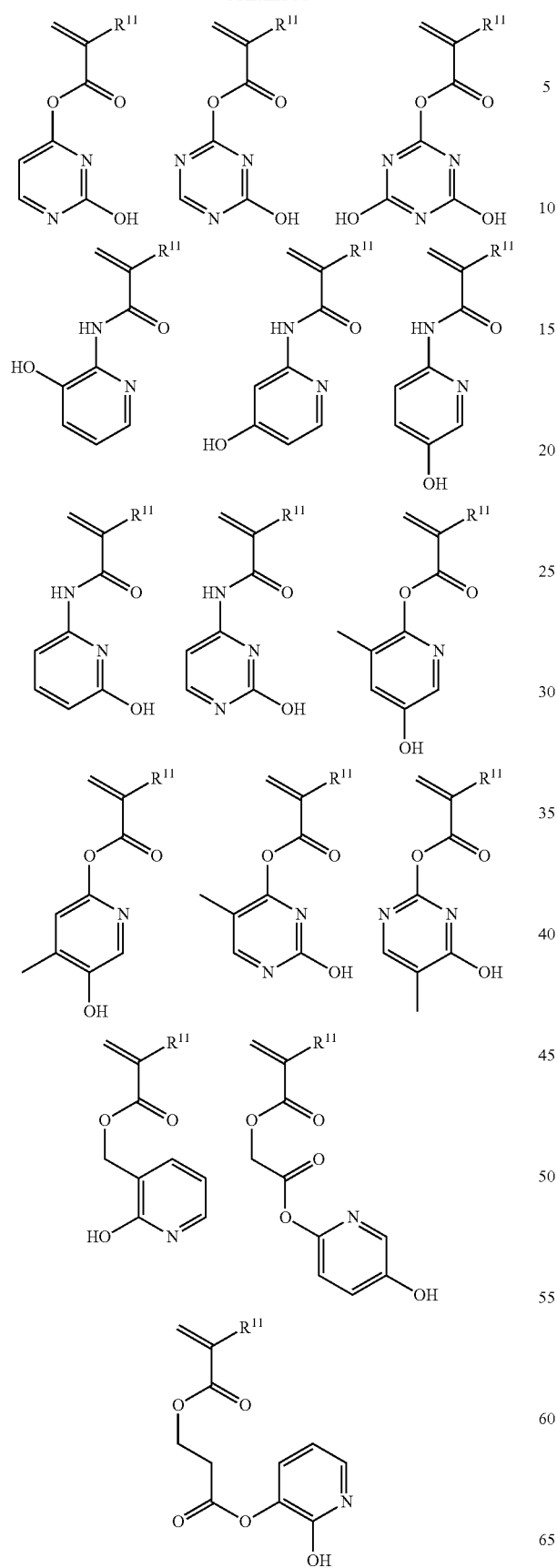
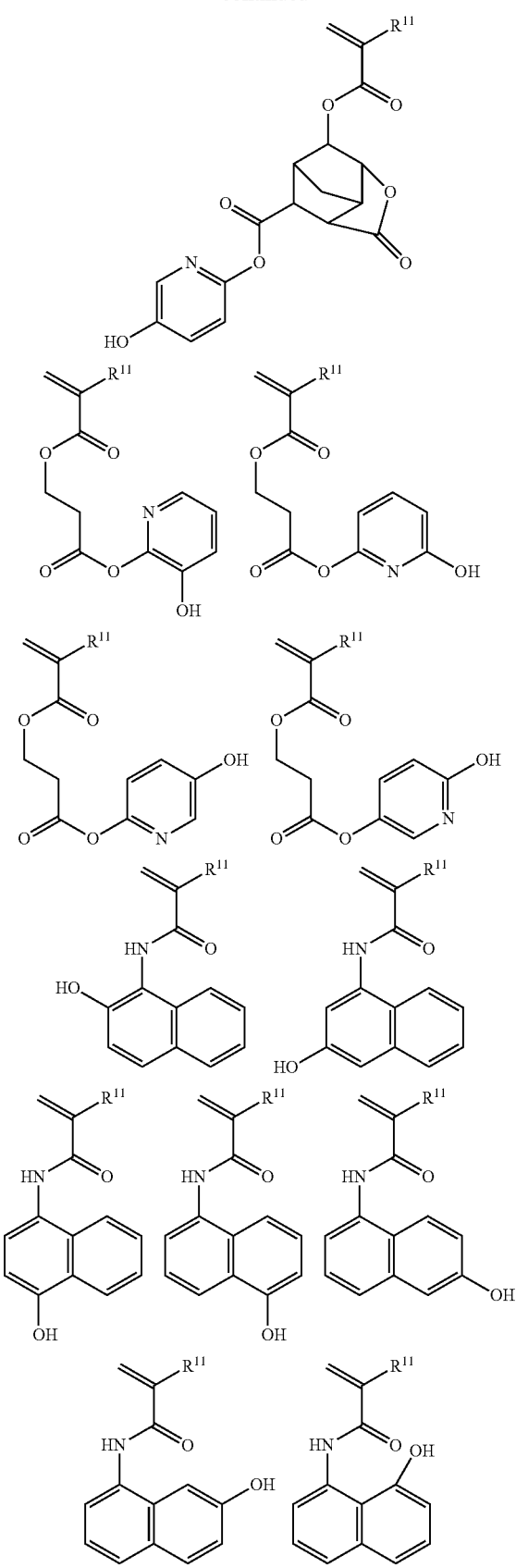

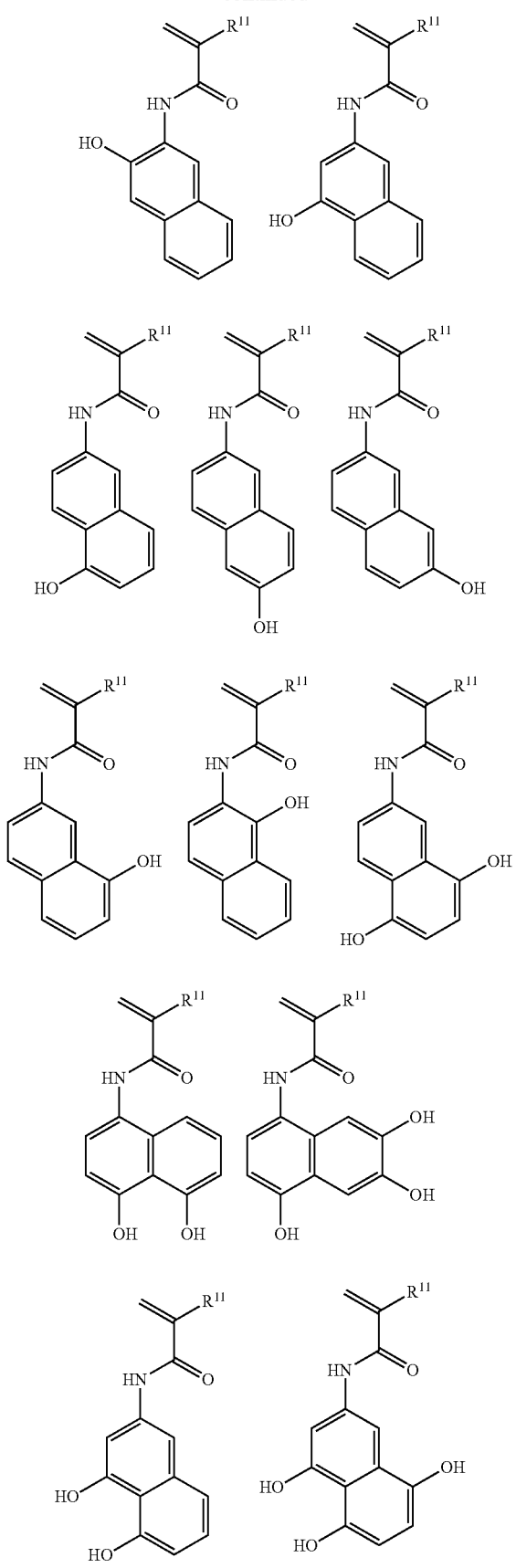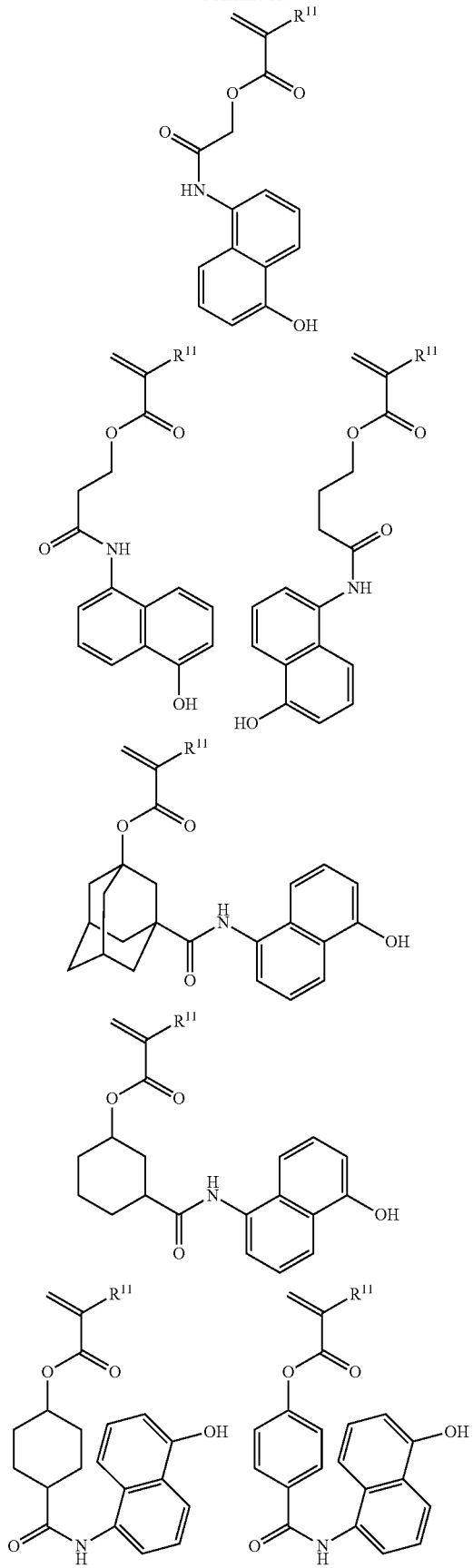

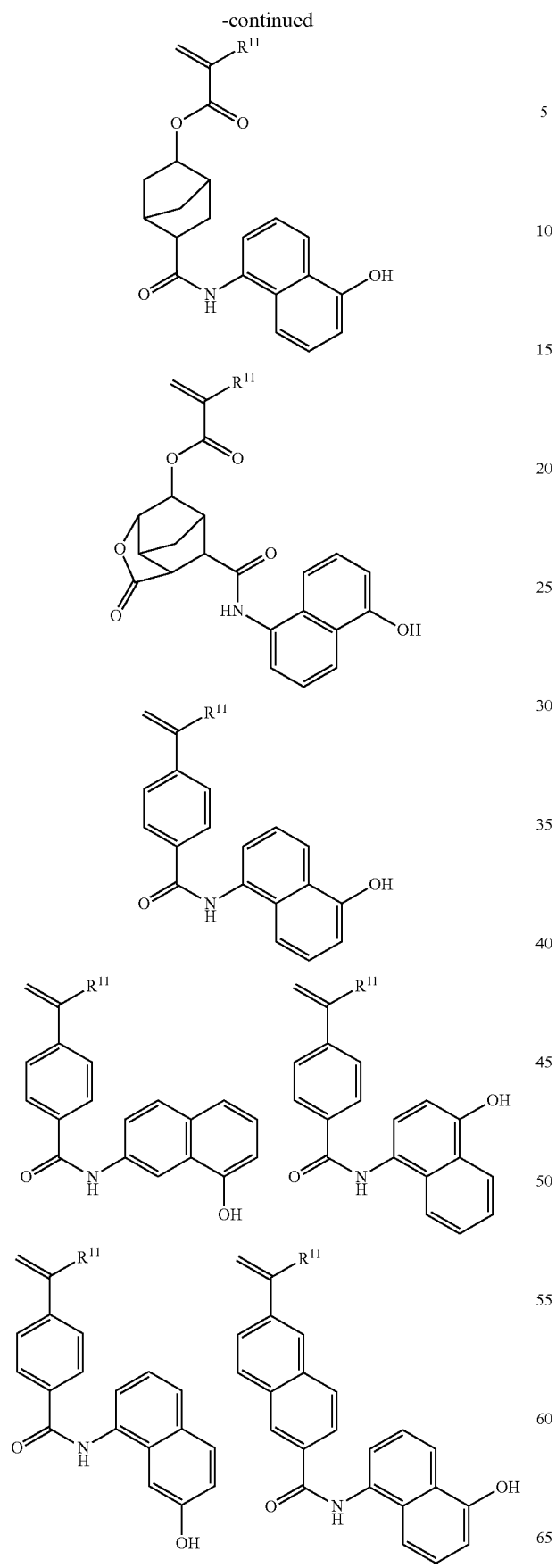
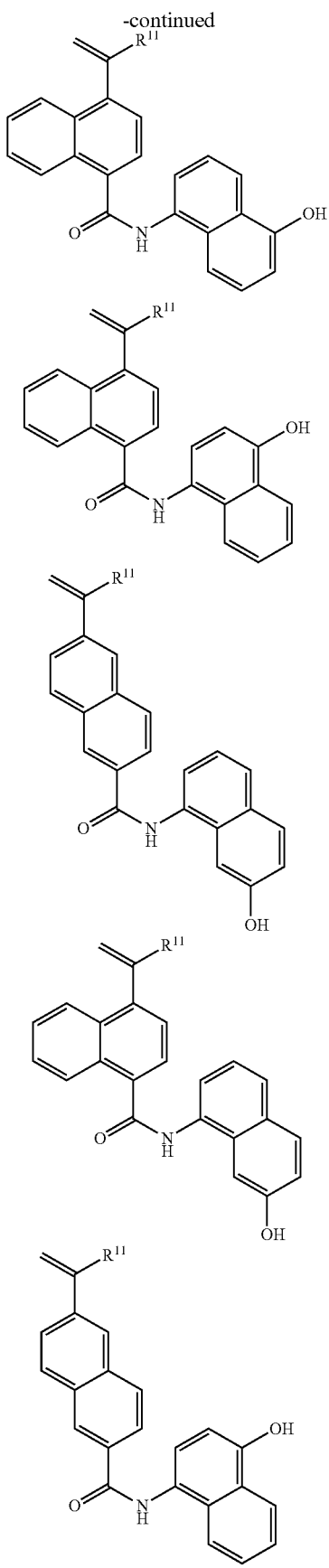

Inclusion of recurring units (c) having a phenolic hydroxyl group is effective for enhancing a sensitizing effect to an acid generator and improving the resist sensitivity.

In a more preferred embodiment, the polymer may further comprise recurring units (d) containing an adhesive group. The adhesive group is selected from among ether, ester, carbonyl, lactone ring, lactam ring, sultone ring, amino, sulfone, sulfonic acid ester, carbonate, hydroxyl (exclusive of phenolic hydroxyl), thiol, carboxyl, carbamate, amide and imide groups.

Examples of the monomer from which the recurring units (d) containing an adhesive group are derived are shown below, but not limited thereto. Notably $R^{14}$ is hydrogen or methyl.

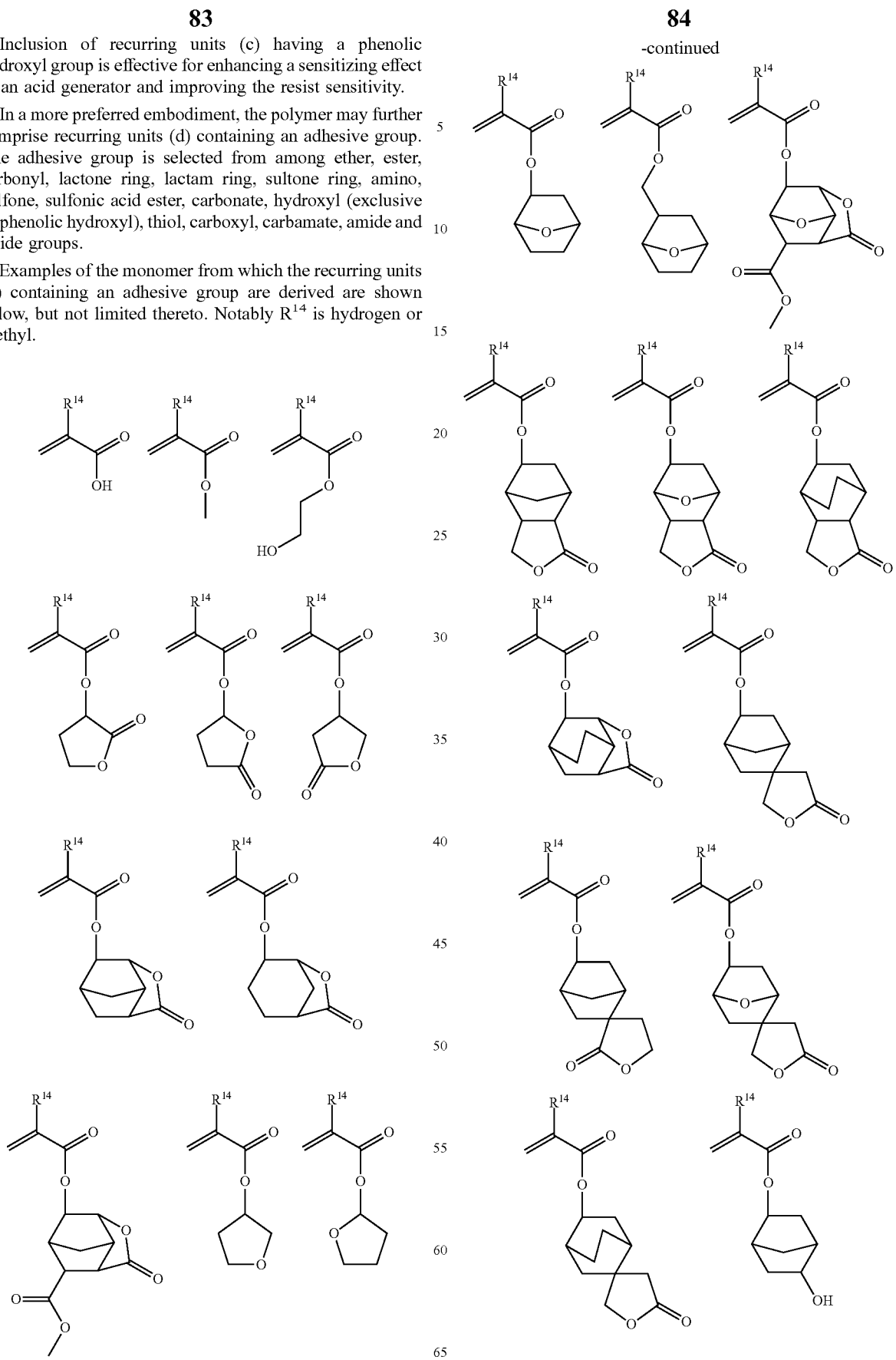

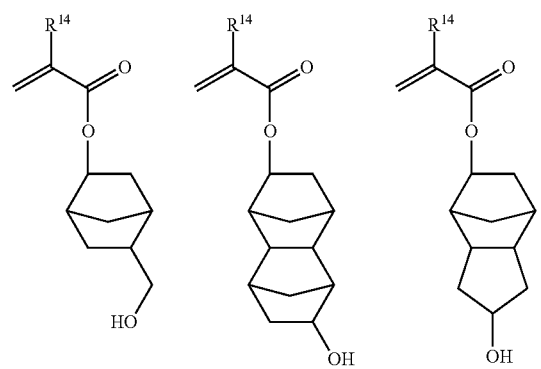
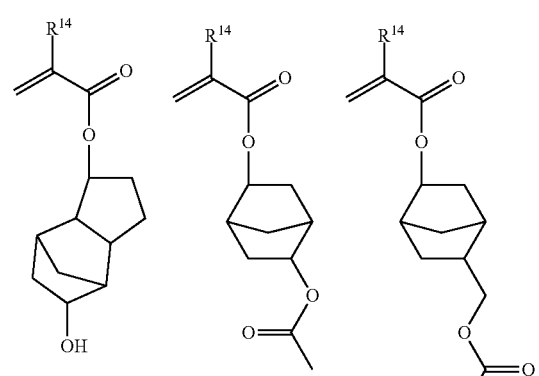
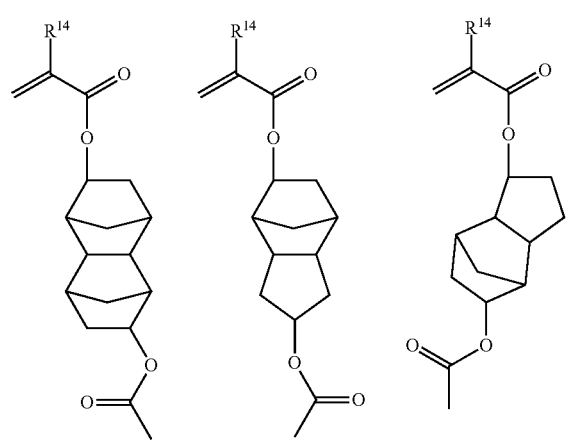
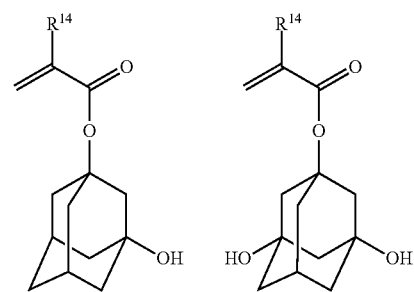
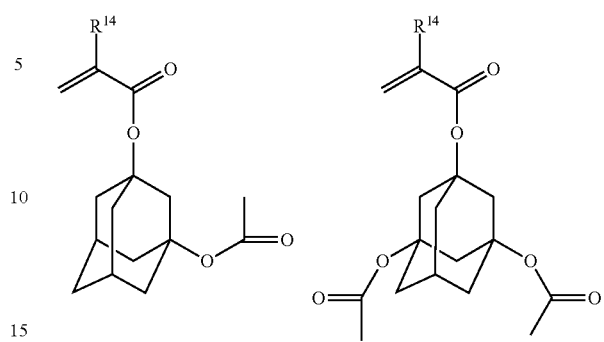
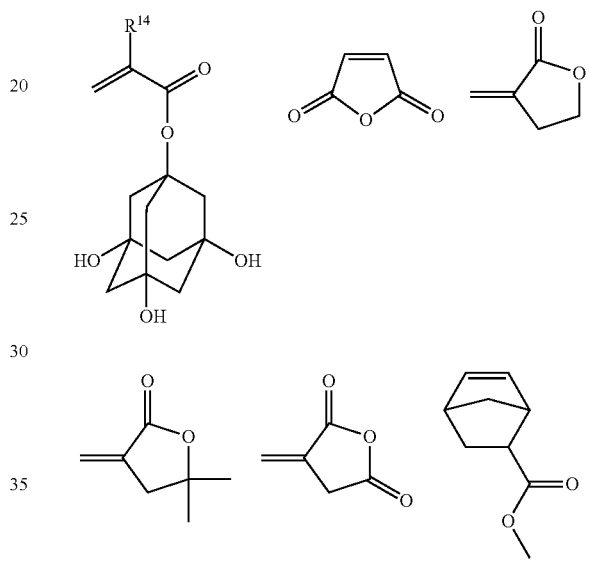
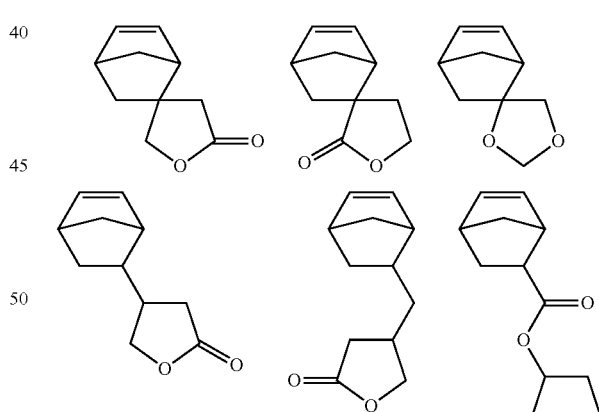
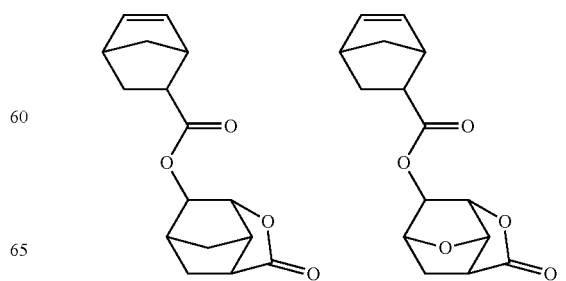

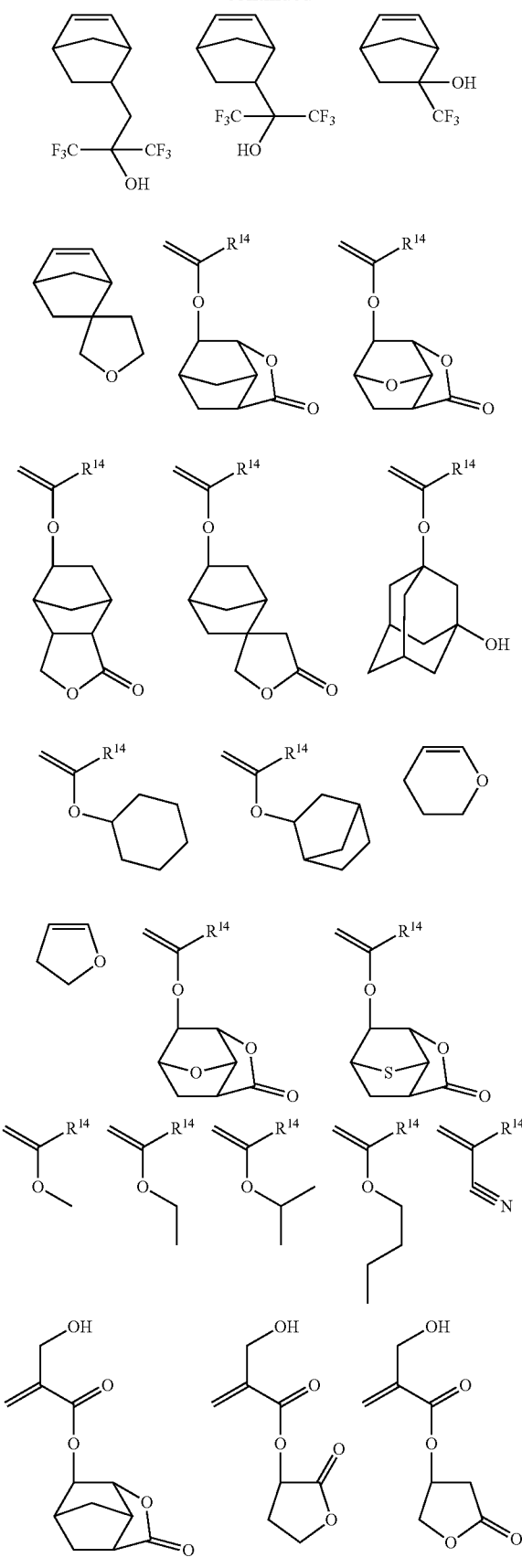
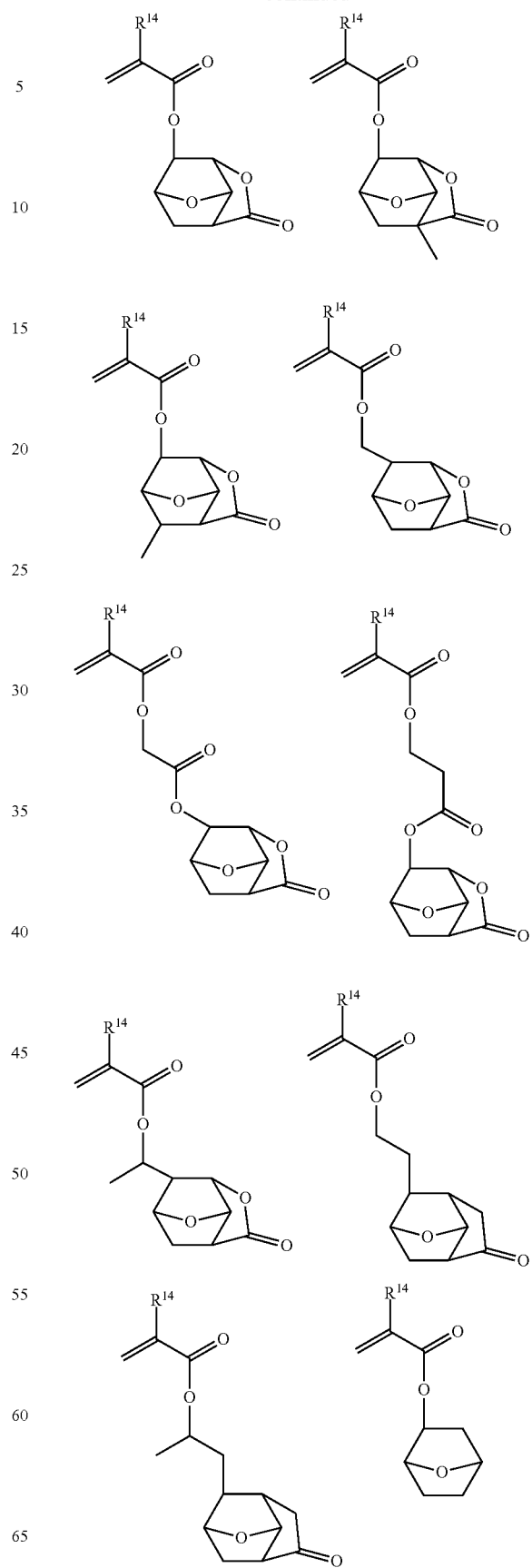

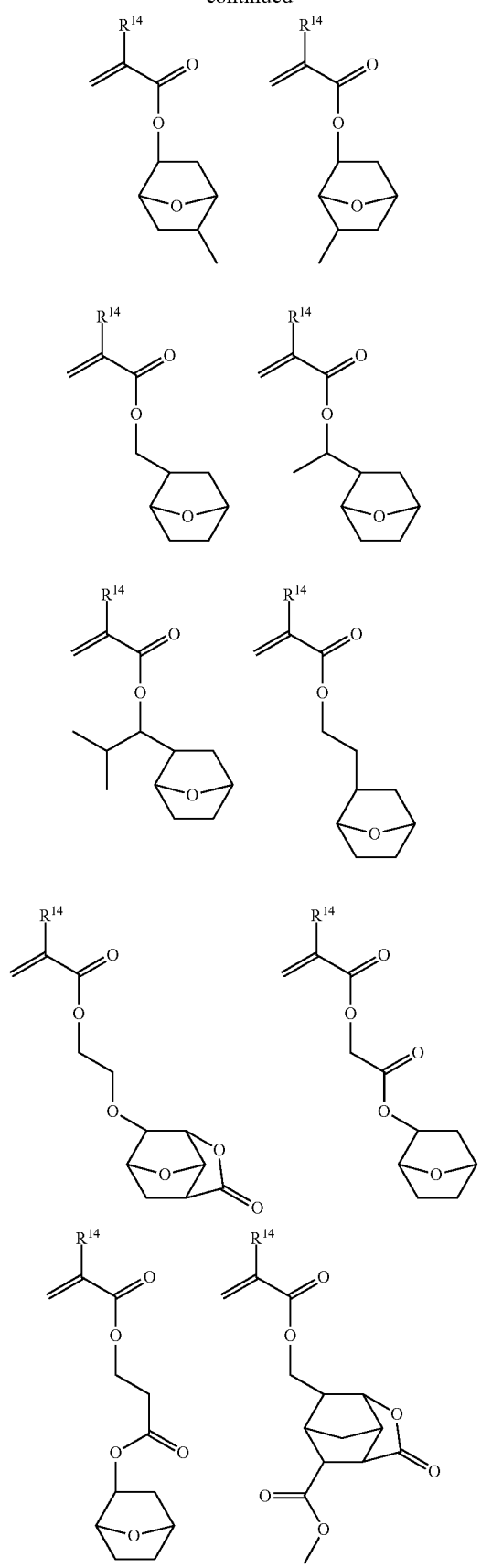
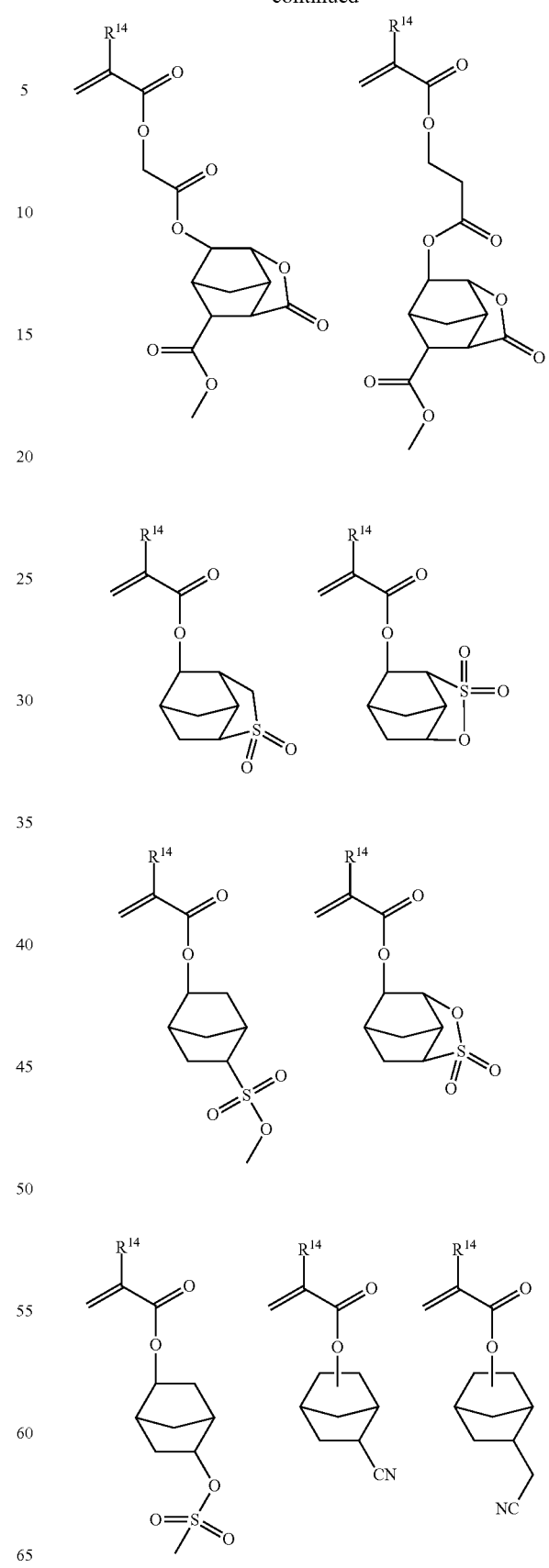

-continued
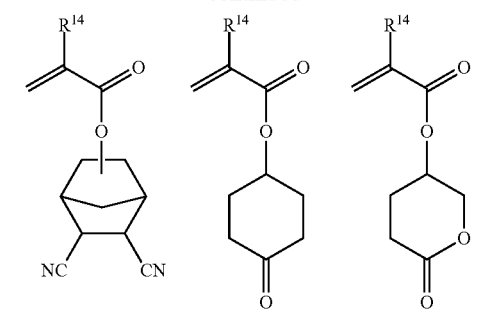
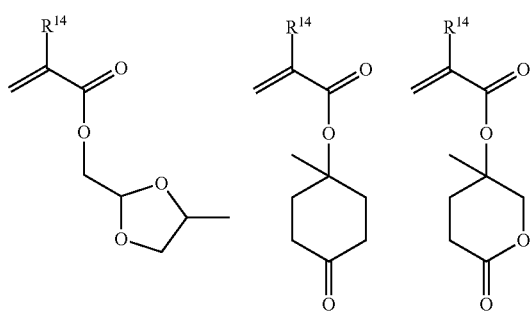
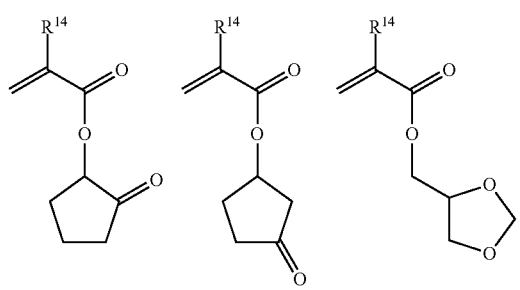
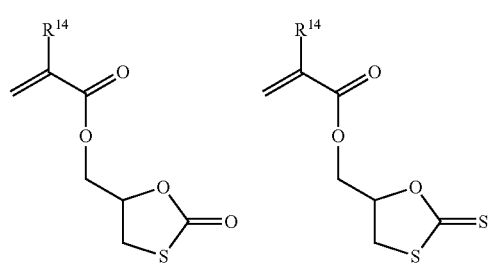
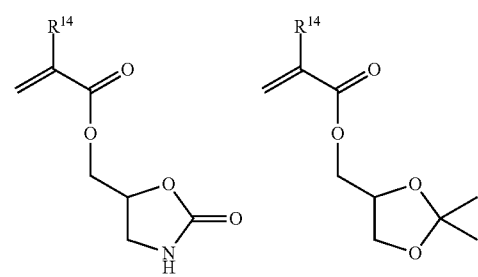
-continued
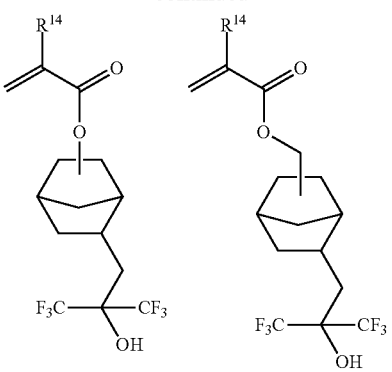
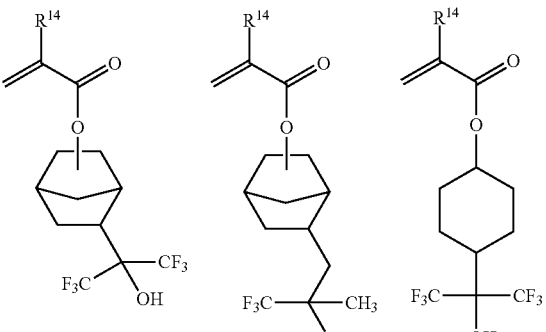
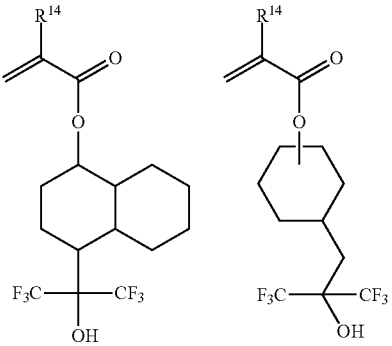
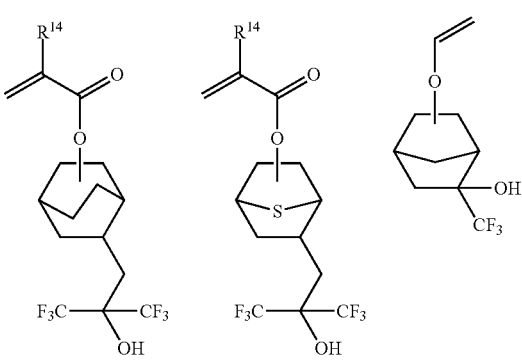

93
-continued
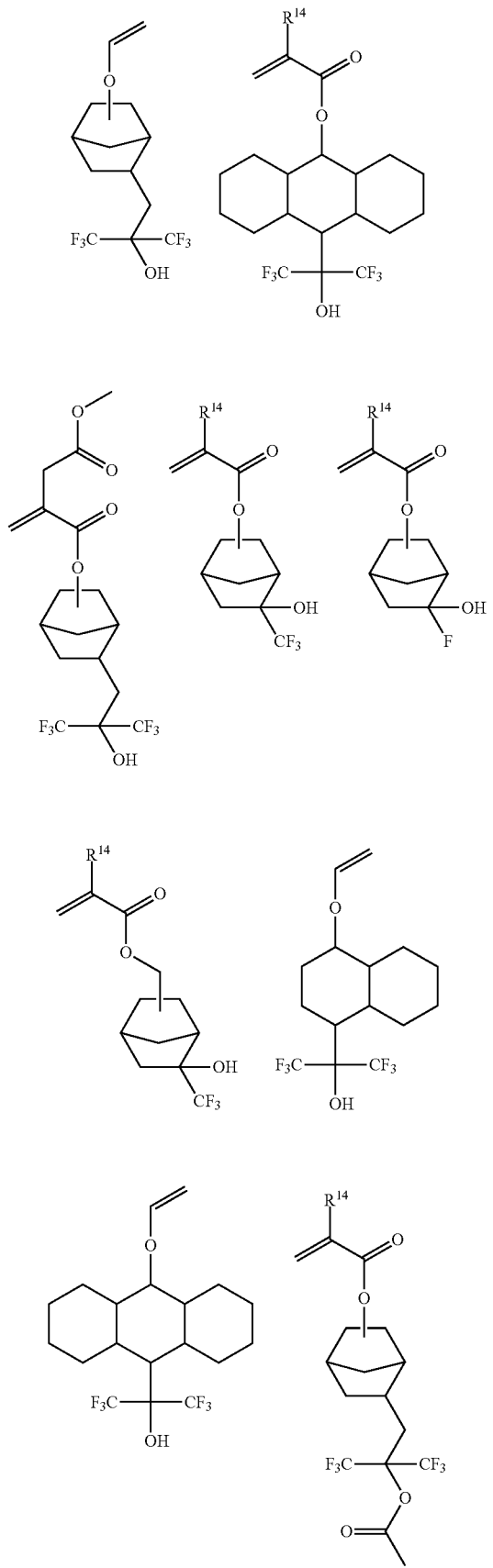
94
-continued
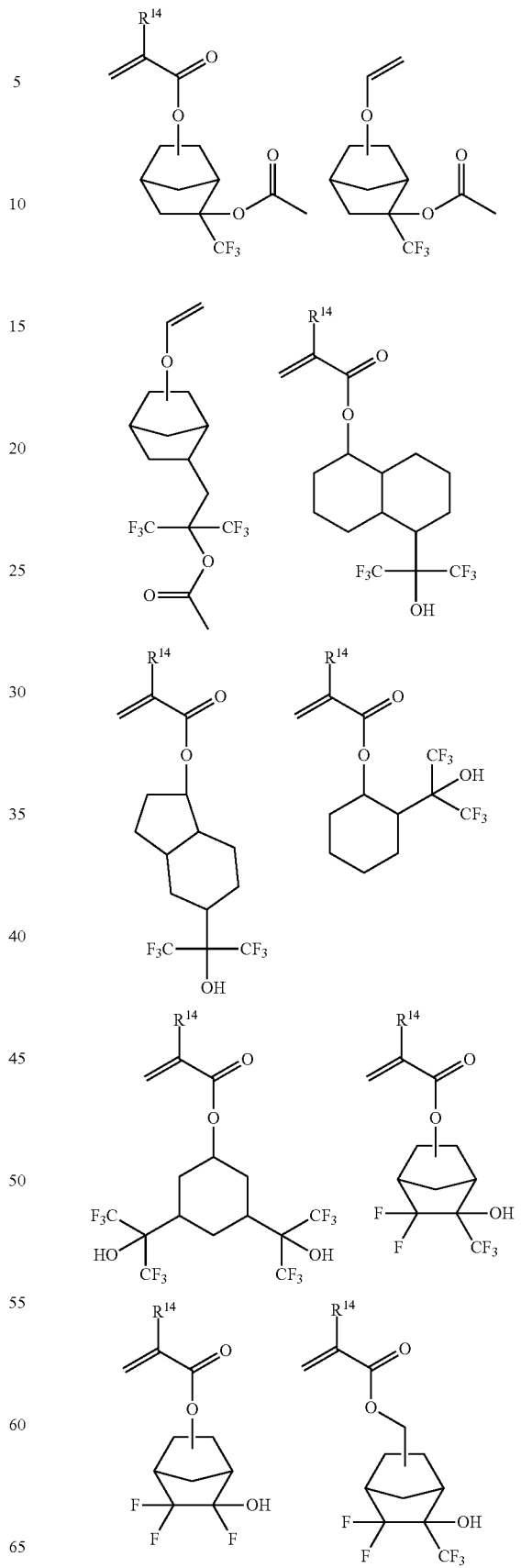

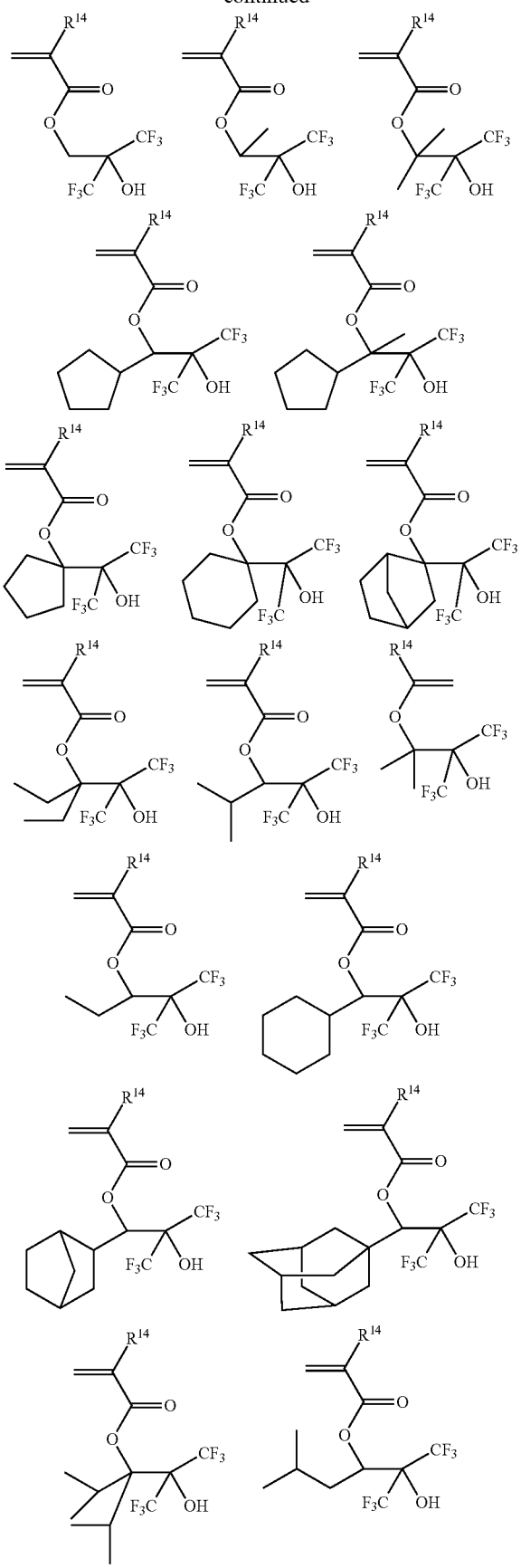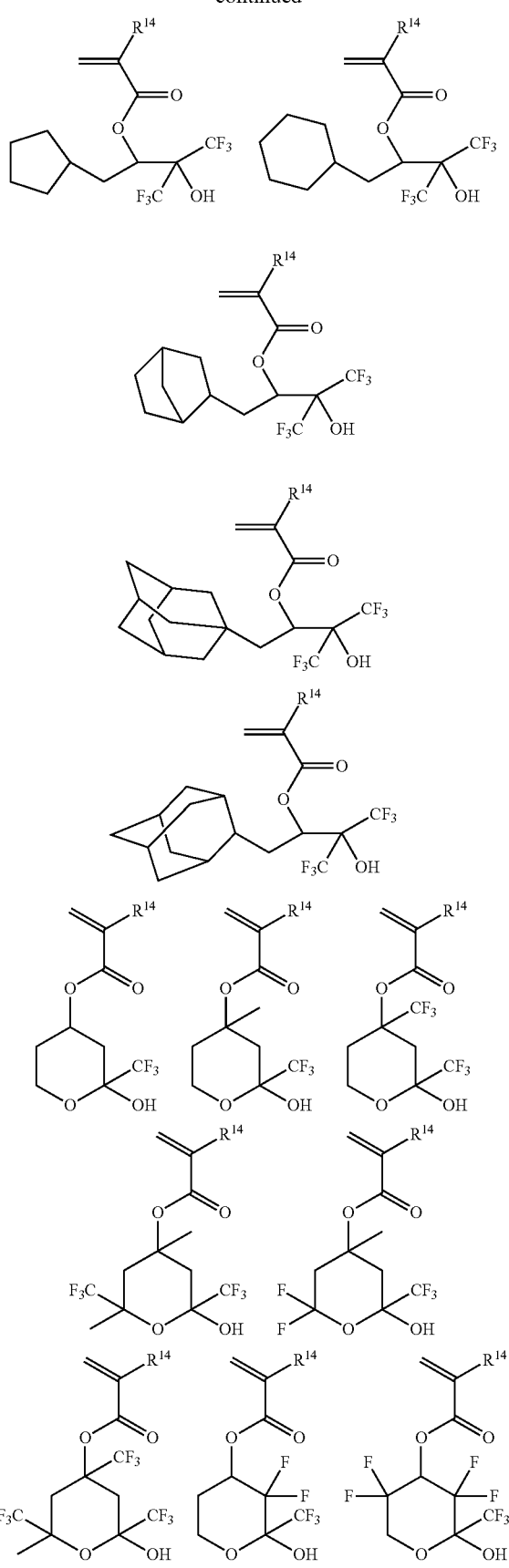

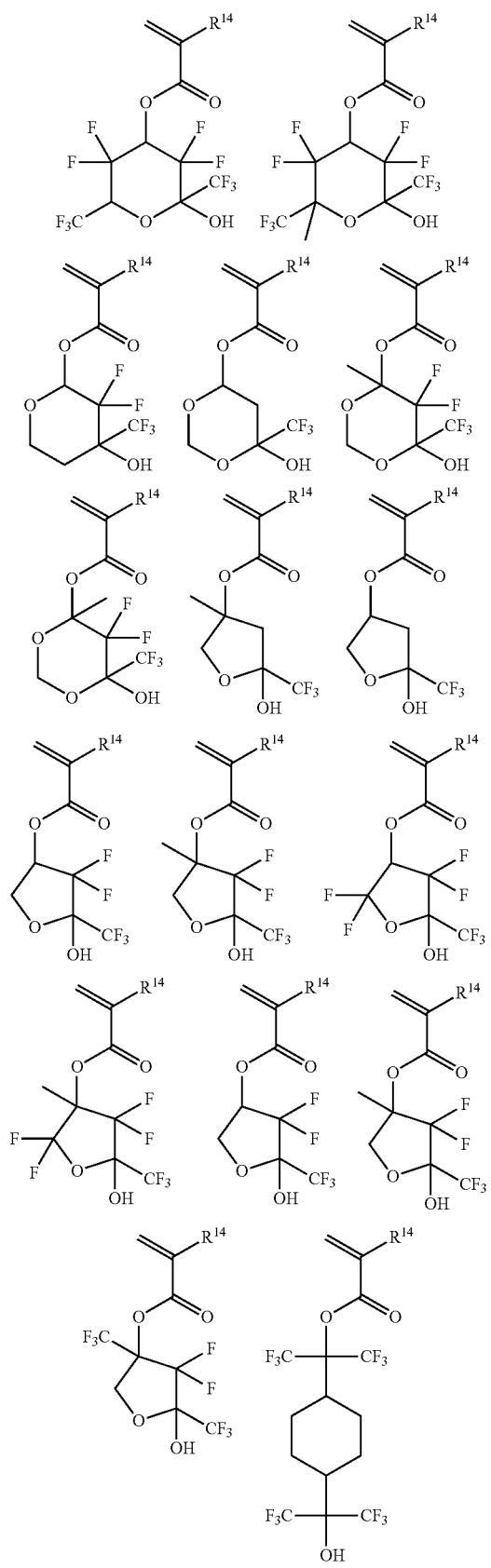
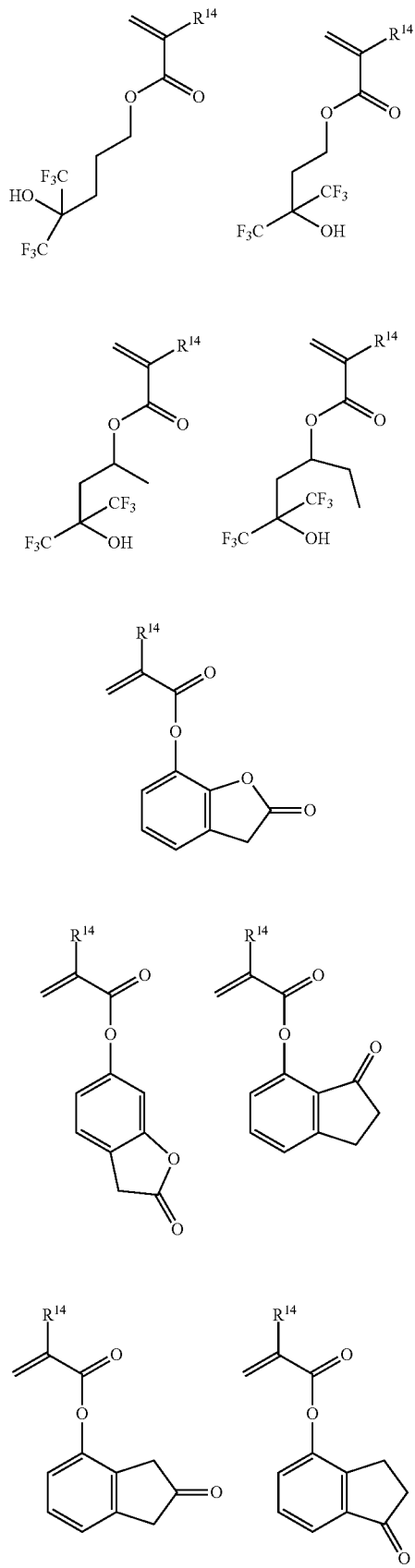

99
-continued
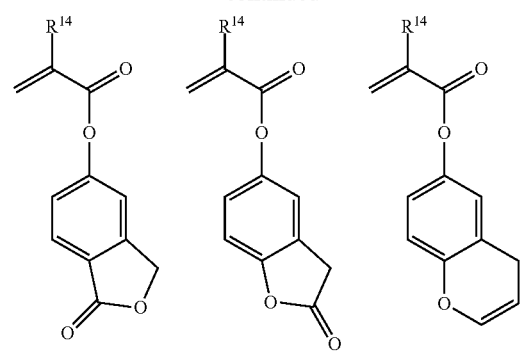
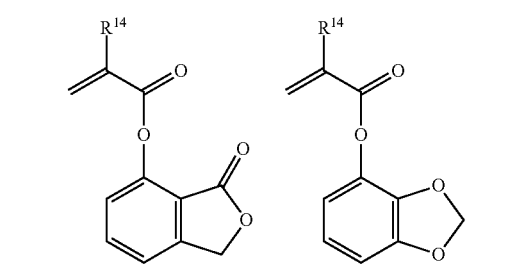
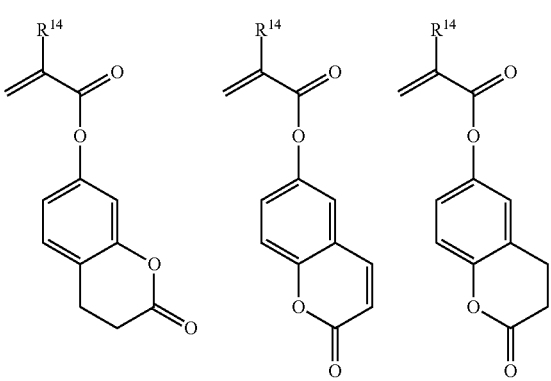
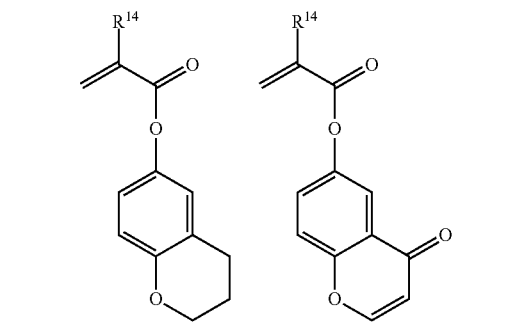
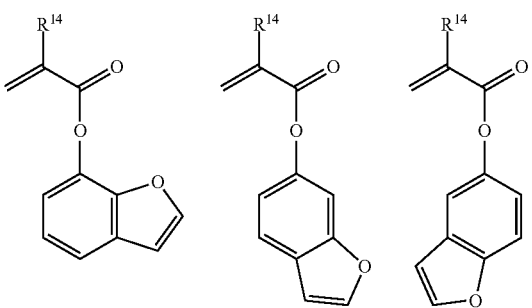
100
-continued
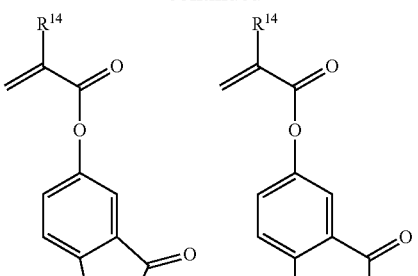
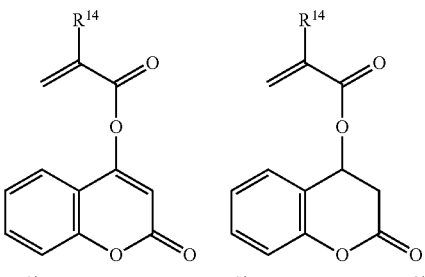
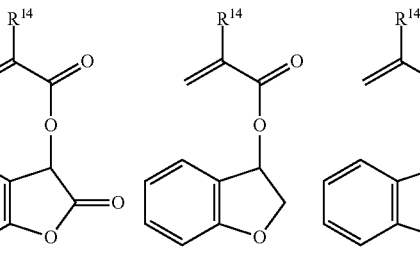
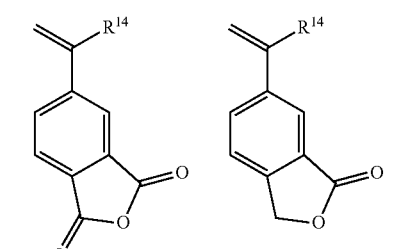
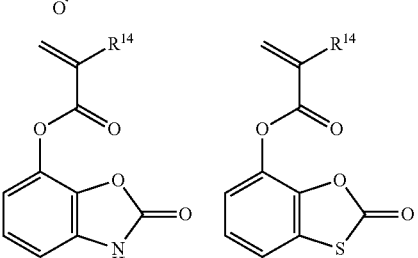
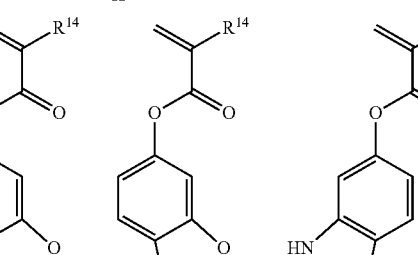

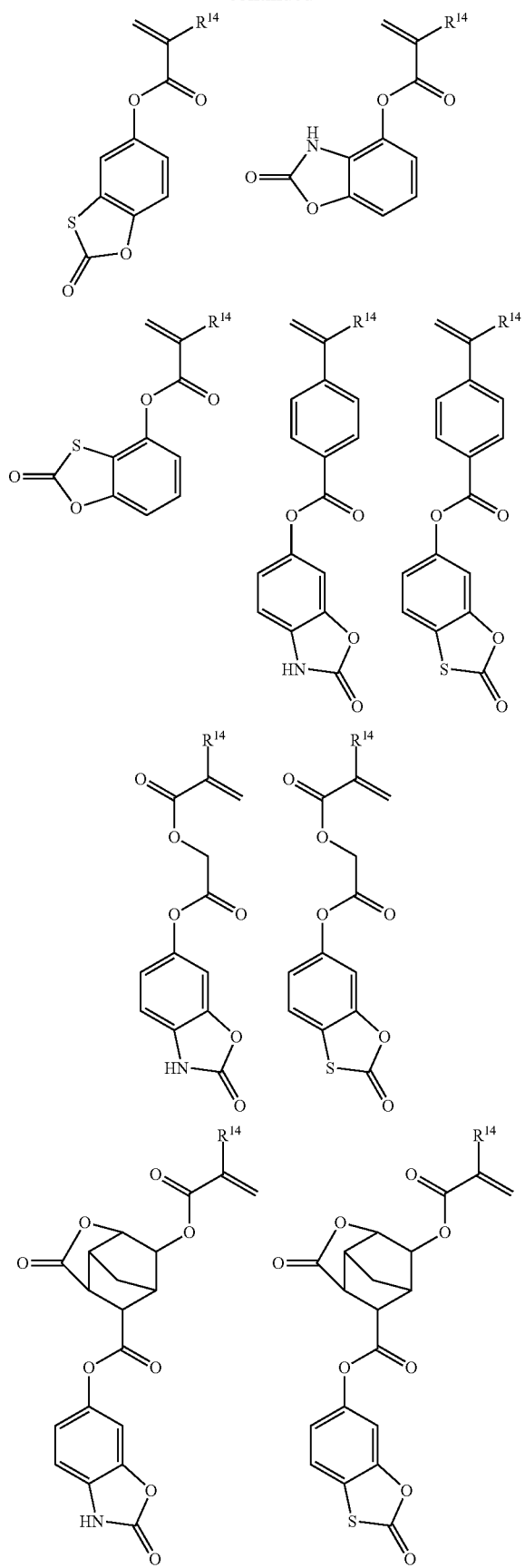
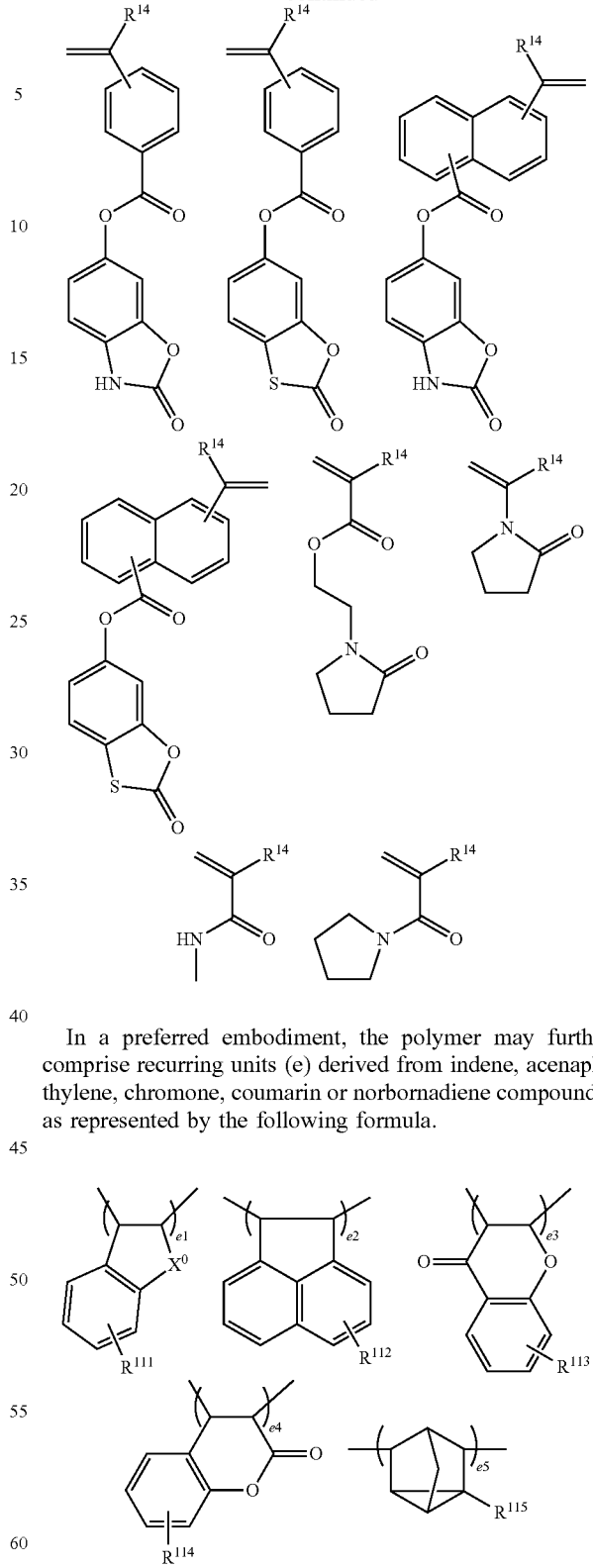

In a preferred embodiment, the polymer may further comprise recurring units (e) derived from indene, acenaphthylene, chromone, coumarin or norbornadiene compounds, as represented by the following formula.

Herein $R^{111}$ to $R^{115}$ are each independently hydrogen, a $C_1$-$C_{30}$ straight, branched or cyclic alkyl group, a $C_1$-$C_{30}$ straight, branched or cyclic haloalkyl group, hydroxy group, $C_1$-$C_{30}$ straight, branched or cyclic alkoxy group, $C_1$-$C_{30}$ straight, branched or cyclic acyl group, $C_2$-$C_{30}$ straight, branched or cyclic alkoxycarbonyl group, $C_6$-$C_{10}$ aryl group, halogen, or 1,1,1,3,3,3-hexafluoro-2-propanol group, $X^0$ is methylene, oxygen or sulfur, e1 to e5 are numbers in the range: $0 \leq e1 \leq 0.5$, $0 \leq e2 \leq 0.5$, $0 \leq e3 \leq 0.5$, $0 \leq e4 \leq 0.5$, $0 \leq e5 \leq 0.5$, and $0 \leq e1+e2+e3+e4+e5 \leq 0.5$.

In a preferred embodiment, the polymer may further comprise recurring units (f) derived from styrene, vinylnaphthalene, vinylanthracene, vinylpyrene or methyleneindane compounds.

The polymer defined herein may be synthesized by any desired methods, for example, by dissolving suitable monomers selected from the monomers corresponding to recurring units (a) to (f) in an organic solvent, adding a radical polymerization initiator thereto, and effecting heat polymerization. Examples of the organic solvent which can be used for polymerization include toluene, benzene, tetrahydrofuran, diethyl ether, dioxane, cyclohexane, cyclopentane, methyl ethyl ketone, and γ-butyrolactone. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably the system is heated at 50 to 80° C. for polymerization to take place. The reaction time is 2 to 100 hours, preferably 5 to 20 hours.

When hydroxystyrene or hydroxyvinylnaphthalene is copolymerized, an alternative method is possible. Specifically, acetoxystyrene or acetoxyvinylnaphthalene is used instead of hydroxystyrene or hydroxyvinylnaphthalene, and after polymerization, the acetoxy group is deprotected by alkaline hydrolysis, for conversion to hydroxystyrene or hydroxyvinylnaphthalene units. For alkaline hydrolysis, a base such as aqueous ammonia or triethylamine may be used. The reaction temperature is −20° C. to 100° C., preferably 0° C. to 60° C., and the reaction time is 0.2 to 100 hours, preferably 0.5 to 20 hours.

In the polymer, recurring units (a) to (f) may be incorporated in the following molar fraction: $0.1 \leq a \leq 0.9$, $0.1 \leq b \leq 0.9$, $0 \leq c \leq 0.8$, $0 \leq d \leq 0.8$, $0 \leq e \leq 0.5$, $0 \leq f \leq 0.5$, and $0.1 \leq a/b \leq 1.5$; preferably $0.12 \leq a \leq 0.7$, $0.15 \leq b \leq 0.8$, $0 \leq c \leq 0.7$, $0 \leq d \leq 0.7$, $0 \leq e \leq 0.4$, $0 \leq f \leq 0.4$, and $0.2 \leq a/b \leq 1.4$; and more preferably $0.15 \leq a \leq 0.6$, $0.18 \leq b \leq 0.7$, $0 \leq c \leq 0.6$, $0 \leq d \leq 0.6$, $0 \leq e \leq 0.3$, $0 \leq f \leq 0.3$, and $0.3 \leq a/b \leq 1.3$. Notably, they preferably meet $a+b+c+d+e+f=1$.

The polymer described in Patent Document 4 has a higher proportion of amino-containing recurring units than the proportion of anion-bound PAG units. If the proportion of amino-containing recurring units is higher, the acid generated upon light exposure is overall quenched with the amine, and thus acid-catalyzed reaction no longer takes place. By contrast, the resist composition of the invention is not a chemically amplified resist composition utilizing acid-catalyzed reaction. This means that no limits are imposed on the proportion of acid generator-containing recurring units and the proportion of amino-containing recurring units, that is, these proportions may be equal or either one may be more than the other.

The polymer should preferably have a weight average molecular weight (Mw) in the range of 1,000 to 500,000, and more preferably 2,000 to 30,000, as measured versus polystyrene standards by GPC using tetrahydrofuran solvent. With Mw<1,000, the resist composition may be less heat resistant. A polymer with Mw>500,000 may be less organic solvent-soluble and likely to invite a footing phenomenon after pattern formation.

If a polymer has a wide molecular weight distribution or dispersity (Mw/Mn), which indicates the presence of lower and higher molecular weight polymer fractions, there is a possibility that foreign matter is left on the pattern or the pattern profile is degraded. The influences of molecular weight and dispersity become stronger as the pattern rule becomes finer. Therefore, the polymer should preferably have a narrow dispersity (Mw/Mn) of 1.0 to 2.0, especially 1.0 to 1.5, in order to provide a resist composition suitable for micropatterning to a small feature size.

The base resin in the resist composition of the invention includes a polymer comprising recurring units (a) having a sulfonium cation bonded to the backbone and recurring units (b) having an amino group bonded to the backbone. The recurring unit (a) having a sulfonium cation bonded to the backbone serves to reduce the solubility of the polymer in the developer, but the solubility in developer is improved after the sulfonium salt is photo-decomposed. Additionally, the fluorosulfonic acid generated by photo-decomposition of the sulfonium salt forms an ammonium salt with the amino-containing recurring unit whereby the solubility in developer is further improved. In this way, a positive resist pattern is formed at a high contrast.

If the base resin does not include a polymer comprising both recurring units (a) having a sulfonium cation bonded to the backbone and recurring units (b) having an amino group bonded to the backbone, for example, if the base resin is a blend of a polymer comprising recurring units (a) and a polymer comprising recurring units (b), then it fails to achieve a dissolution contrast satisfactory as positive resist.

If the base resin includes recurring units having an acid labile group, then the dissolution rate of resist film in the unexposed region is increased. Additionally, since all or almost all of the acid generated upon light exposure is converted into an ammonium salt, acid-catalyzed deprotection reaction does not take place. Therefore, the base resin including recurring units having an acid labile group becomes a positive resist composition having a low dissolution contrast.

The polymer defined herein is adequate as a base resin in a positive resist composition adapted to form a positive pattern via organic solvent development. The polymer is used as the base resin and combined with an organic solvent, dissolution regulator, surfactant and other components, in a suitable combination for a particular purpose, to formulate a positive resist composition. The composition is of positive tone in the sense that the polymer in the exposed region is converted to an ammonium salt having the structure of ionic liquid, whereby the dissolution rate in developer is accelerated. The resulting resist pattern has improved edge roughness. By virtue of these advantages, the resist composition is fully useful in commercial application and suited as a pattern-forming resist material for the fabrication of VLSIs.

As mentioned above, the resist composition may comprise an organic solvent, basic compound, surfactant, and/or acetylene alcohol in addition to the base resin.

The organic solvent used herein is not particularly limited as long as the base resin and other components are dissolvable therein. Exemplary organic solvents include ketones such as cyclohexanone and methyl-2-n-pentyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, t-butyl acetate, t-butyl propionate, and propylene glycol mono-t-butyl ether acetate; and lactones such as γ-butyrolactone, and mixtures thereof. An appropriate amount of the organic solvent used is 200 to 3,000 parts, more preferably 400 to 2,500 parts by weight per 100 parts by weight of the base resin.

Suitable basic compounds are described in JP-A 2008-111103, paragraphs [0146]-[0164], suitable surfactants in paragraphs [0165]-[0166], and suitable acetylene alcohols in paragraphs [0179]-[0182] (U.S. Pat. No. 7,537,880).

Process

The positive resist composition is used in the fabrication of various integrated circuits. Pattern formation using the resist composition may be performed by well-known lithography processes. The process generally involves coating, exposure, and development.

For example, the positive resist composition is first applied onto a substrate on which an integrated circuit is to be formed (e.g., Si, $SiO_2$, SiN, SiON, TiN, WSi, BPSG, SOG, or organic antireflective coating) or a substrate on which a mask circuit is to be formed (e.g., Cr, CrO, CrON, or MoSi) by a suitable coating technique such as spin coating, roll coating, flow coating, dip coating, spray coating or doctor coating. The coating is prebaked on a hot plate at a temperature of 60 to 150° C. for 10 seconds to 30 minutes, preferably 80 to 120° C. for 30 seconds to 20 minutes. The resulting resist film is generally 0.01 to 2.0 μm thick.

If desired, a protective film may be formed on the resist film. The protective film is preferably formed of a developer-soluble composition so that both formation of a resist pattern and stripping of the protective film may be achieved during development. The protective film has the functions of restraining outgassing from the resist film, filtering or cutting off out-of-band (OOB) light having a wavelength of 140 to 300 nm emitted by the EUV laser (other than 13.5 nm), and preventing the resist film from assuming T-top profile or from losing its thickness under environmental impacts.

The resist film is then exposed to a desired pattern of high-energy radiation such as UV, deep-UV, EB, EUV of wavelength 3 to 15 nm, x-ray, soft x-ray, excimer laser light, γ-ray or synchrotron radiation directly or through a mask. The exposure dose is preferably about 1 to 1,000 $mJ/cm^2$, more preferably about 10 to 500 $mJ/cm^2$, or about 0.1 to 1,000 $\mu C/cm^2$, more preferably about 0.5 to 500 $\mu C/cm^2$. The resist film is optionally baked (PEB) on a hot plate, preferably at 50 to 150° C. for 10 seconds to 30 minutes, more preferably at 60 to 120° C. for 30 seconds to 20 minutes.

Thereafter the resist film is developed in a developer for 3 seconds to 3 minutes, preferably 5 seconds to 2 minutes by conventional techniques such as dip, puddle or spray techniques. The resist film in the exposed area is dissolved in the developer whereas the resist film in the unexposed area is not dissolved. In this way, the desired positive pattern is formed on the substrate. It is appreciated that the resist composition of the invention is best suited for micropatterning using such high-energy radiation as EB, EUV, x-ray, soft x-ray, γ-ray and synchrotron radiation among others.

For the development, an organic solvent is used. The developer used herein contains at least one organic solvent selected from among 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate, which may be used alone or in admixture.

At the end of development, the resist film may be dried or rinsed. For example, the developer may be removed by spin drying. In the case of rinsing, a solvent which is miscible with the developer and does not dissolve the resist film is preferred as the rinsing liquid. Suitable solvents include alcohols of 3 to 10 carbon atoms, ether compounds of 8 to 12 carbon atoms, alkanes, alkenes, and alkynes of 6 to 12 carbon atoms, and aromatic solvents.

Specifically, suitable alcohols of 3 to 10 carbon atoms include n-propyl alcohol, isopropyl alcohol, 1-butyl alcohol, 2-butyl alcohol, isobutyl alcohol, t-butyl alcohol, 1-pentanol, 2-pentanol, 3-pentanol, t-pentyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether compounds of 8 to 12 carbon atoms include di-n-butyl ether, diisobutyl ether, di-s-butyl ether, di-n-pentyl ether, diisopentyl ether, di-s-pentyl ether, di-t-pentyl ether, and di-n-hexyl ether. Suitable alkanes of 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Suitable alkenes of 6 to 12 carbon atoms include hexene, heptene, octene, cyclohexene, methylcyclohexene, dimethylcyclohexene, cycloheptene, and cyclooctene. Suitable alkynes of 6 to 12 carbon atoms include hexyne, heptyne, and octyne. Suitable aromatic solvents include toluene, xylene, ethylbenzene, isopropylbenzene, t-butylbenzene, and mesitylene. The solvents may be used alone or in admixture.

The positive resist composition is used not only in the lithography for forming semiconductor circuits, but also in the formation of mask circuit patterns, micromachines, and thin-film magnetic head circuits.

EXAMPLE

Examples and Comparative Examples are given below for further illustrating the invention, but they should not be construed as limiting the invention thereto. All parts (pbw) are by weight. Mw is a weight average molecular weight as measured versus polystyrene standards by GPC using tetrahydrofuran (THF) solvent.

The following polymer Synthesis Examples use PAG Monomers 1 to 10 and Comparative PAG Monomer 1 which are identified below.

PAG Monomer 1
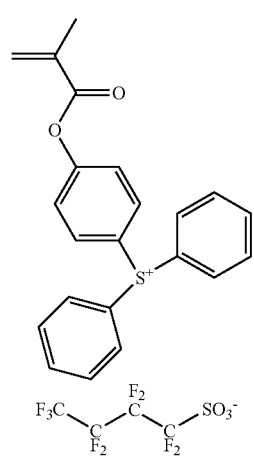
PAG Monomer 2
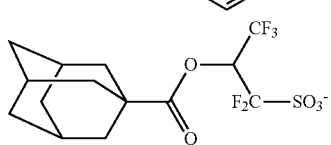
PAG Monomer 3
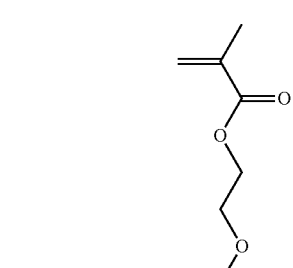
PAG Monomer 4
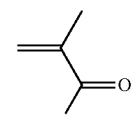
PAG Monomer 5
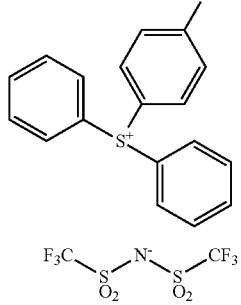

PAG Monomer 6
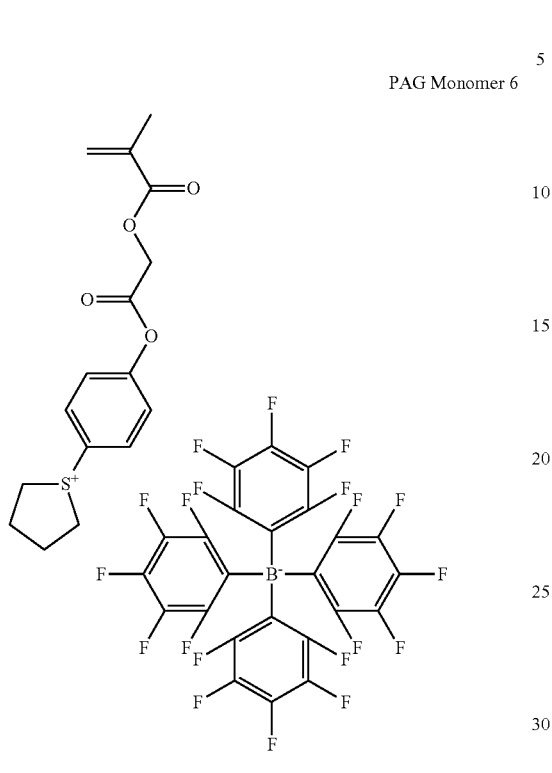
PAG Monomer 7
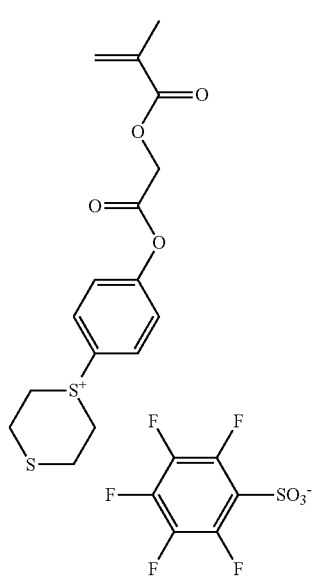
PAG Monomer 8
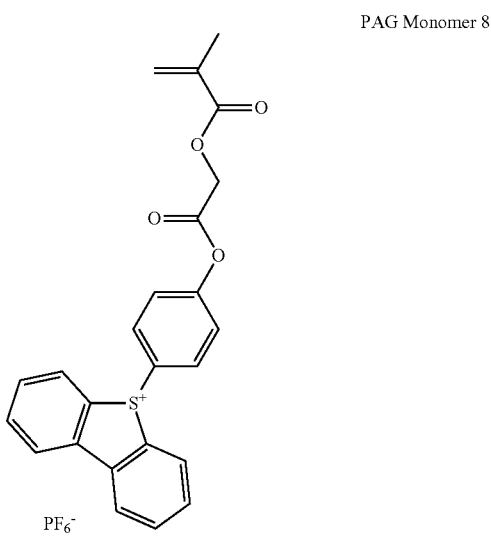
PAG Monomer 9
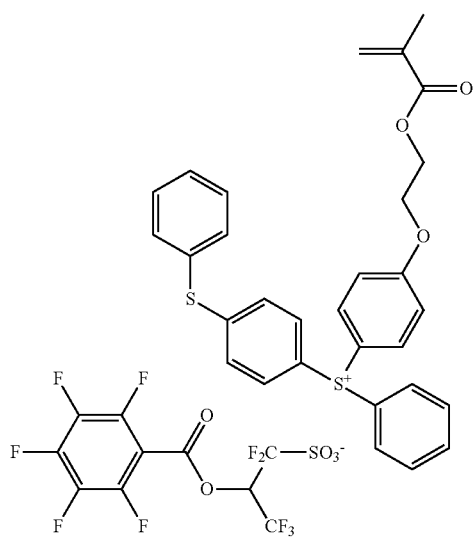
PAG Monomer 10
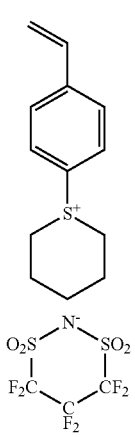

Comparative PAG Monomer 1

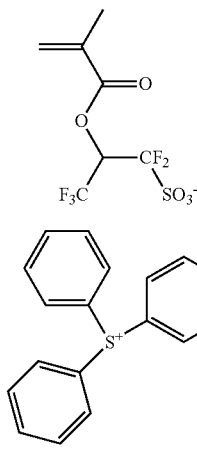

1. Synthesis of Polymers

Synthesis Example 1

A 2-L flask was charged with 19.4 g of PAG Monomer 1, 4.7 g of 2-(dimethylamino)ethyl methacrylate, 7.1 g of 4-hydroxyphenyl methacrylate, and 40 g of THF solvent. The reactor was cooled at −70° C. in nitrogen atmosphere, after which vacuum pumping and nitrogen blow were repeated three times. The reactor was warmed up to room temperature, whereupon 1.2 g of 2,2′-azobisisobutyronitrile (AIBN) as polymerization initiator was added. The reactor was heated at 60° C., whereupon reaction ran for 15 hours. The reaction solution was poured into 1 L of isopropyl alcohol for precipitation. The precipitate was collected by filtration and dried in vacuum at 60° C., yielding a white polymer, designated Polymer 1. The polymer was analyzed by $^{13}$C- and $^1$H-NMR and GPC, with the results shown below.

Copolymer Composition Ratio (Molar Ratio)

PAG Monomer 1: 2-(dimethylamino)ethyl methacrylate: 4-hydroxyphenyl methacrylate=0.3:0.3:0.4

Mw=10,900

Mw/Mn=1.71

Polymer 1

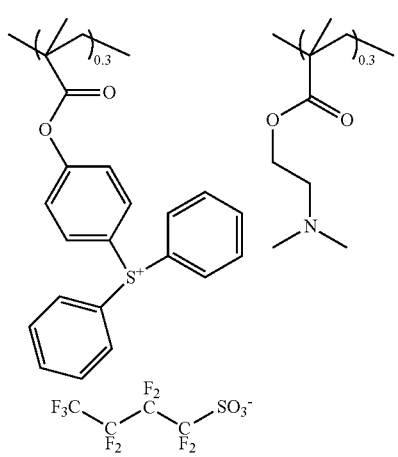

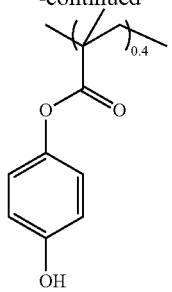

Synthesis Example 2

A 2-L flask was charged with 39.1 g of PAG Monomer 2, 9.5 g of 2-(diethylamino)ethyl methacrylate, and 40 g of THF solvent. The reactor was cooled at −70° C. in nitrogen atmosphere, after which vacuum pumping and nitrogen blow were repeated three times. The reactor was warmed up to room temperature, whereupon 1.2 g of AIBN as polymerization initiator was added. The reactor was heated at 60° C., whereupon reaction ran for 15 hours. The reaction solution was poured into 1 L of isopropyl alcohol for precipitation. The precipitate was collected by filtration and dried in vacuum at 60° C., yielding a white polymer, designated Polymer 2. The polymer was analyzed by $^{13}$C- and $^1$H-NMR and GPC, with the results shown below.

Copolymer Composition Ratio (Molar Ratio)

PAG Monomer 2: 2-(diethylamino)ethyl methacrylate=0.46:0.54

Mw=7,600

Mw/Mn=1.89

Polymer 2

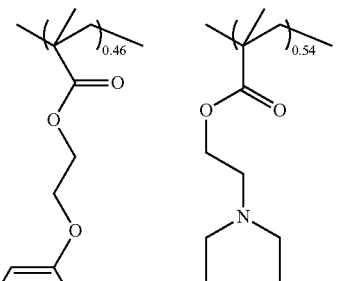
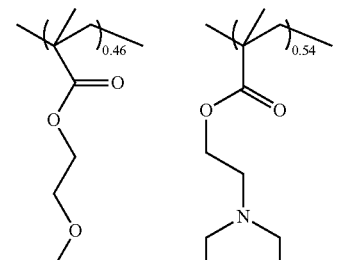

Synthesis Example 3

A 2-L flask was charged with 23.5 g of PAG Monomer 3, 5.5 g of 2-(dimethylamino)ethyl methacrylate, 5.3 g of 4-hydroxyphenyl methacrylamide, and 40 g of THF solvent.

The reactor was cooled at −70° C. in nitrogen atmosphere, after which vacuum pumping and nitrogen blow were repeated three times. The reactor was warmed up to room temperature, whereupon 1.2 g of AIBN as polymerization initiator was added. The reactor was heated at 60° C., whereupon reaction ran for 15 hours. The reaction solution was poured into 1 L of isopropyl alcohol for precipitation. The precipitate was collected by filtration and dried in vacuum at 60° C., yielding a white polymer, designated Polymer 3. The polymer was analyzed by $^{13}$C- and $^1$H-NMR and GPC, with the results shown below.

Copolymer Composition Ratio (Molar Ratio)
PAG Monomer 3: 2-(dimethylamino)ethyl methacrylate: 4-hydroxyphenyl methacrylamide=0.35:0.35:0.3
Mw=7,100
Mw/Mn=1.69

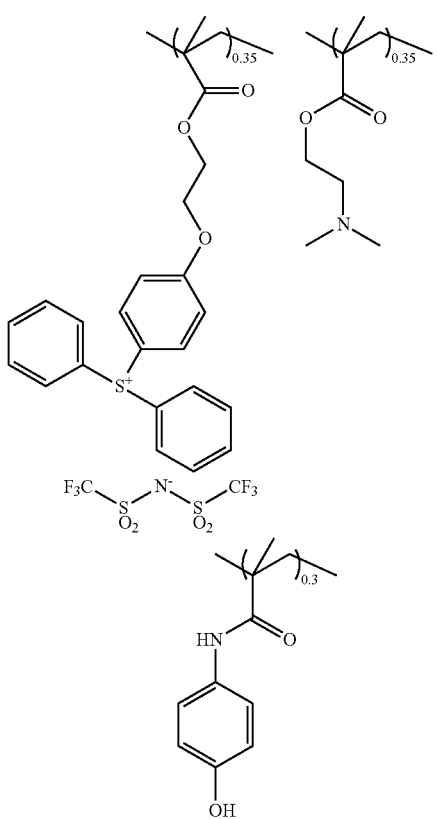

Polymer 3

Synthesis Example 4

A 2-L flask was charged with 13.4 g of PAG Monomer 4, 5.5 g of vinylimidazole, 4.1 g of 3,5-dimethyl-4-hydroxyphenyl methacrylate, 3.4 g of 2-oxooxolan-3-yl methacrylate, and 40 g of THF solvent. The reactor was cooled at −70° C. in nitrogen atmosphere, after which vacuum pumping and nitrogen blow were repeated three times. The reactor was warmed up to room temperature, whereupon 1.2 g of AIBN as polymerization initiator was added. The reactor was heated at 60° C., whereupon reaction ran for 15 hours. The reaction solution was poured into 1 L of isopropyl alcohol for precipitation. The precipitate was collected by filtration and dried in vacuum at 60° C., yielding a white polymer, designated Polymer 4. The polymer was analyzed by $^{13}$C- and $^1$H-NMR and GPC, with the results shown below.

Copolymer Composition Ratio (Molar Ratio)
PAG Monomer 4: vinylimidazole:3,5-dimethyl-4-hydroxyphenyl methacrylate:2-oxooxolan-3-yl methacrylate=0.3:0.3:0.2:0.2
Mw=7,600
Mw/Mn=1.63

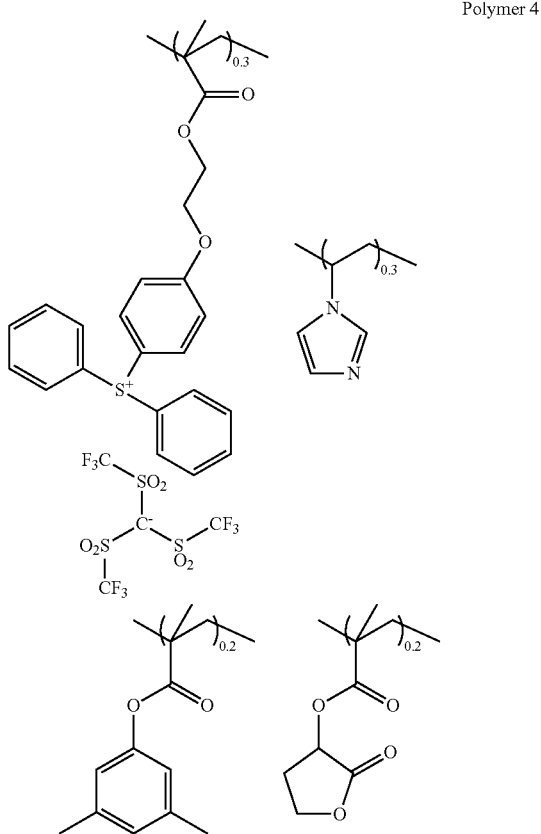

Polymer 4

Synthesis Example 5

A 2-L flask was charged with 14.2 g of PAG Monomer 5, 5.9 g of 2-piperidineethyl-1-yl methacrylate, 4.7 g of 3-tert-butyl-4-hydroxyphenyl methacrylate, 4.7 g of tetrahydro-2-oxofuran-3-yl methacrylate, and 40 g of THF solvent. The reactor was cooled at −70° C. in nitrogen atmosphere, after which vacuum pumping and nitrogen blow were repeated three times. The reactor was warmed up to room temperature, whereupon 1.2 g of AIBN as polymerization initiator was added. The reactor was heated at 60° C., whereupon reaction ran for 15 hours. The reaction solution was poured into 1 L of isopropyl alcohol for precipitation. The precipitate was collected by filtration and dried in vacuum at 60° C., yielding a white polymer, designated Polymer 5. The polymer was analyzed by $^{13}$C- and $^1$H-NMR and GPC, with the results shown below.

Copolymer Composition Ratio (Molar Ratio)
PAG Monomer 5: 2-piperidineethyl-1-yl methacrylate:3-tert-butyl-4-hydroxyphenyl methacrylate:tetrahydro-2-oxofuran-3-yl methacrylate=0.3:0.3:0.2:0.2
Mw=8,400
Mw/Mn=1.64

Polymer 5

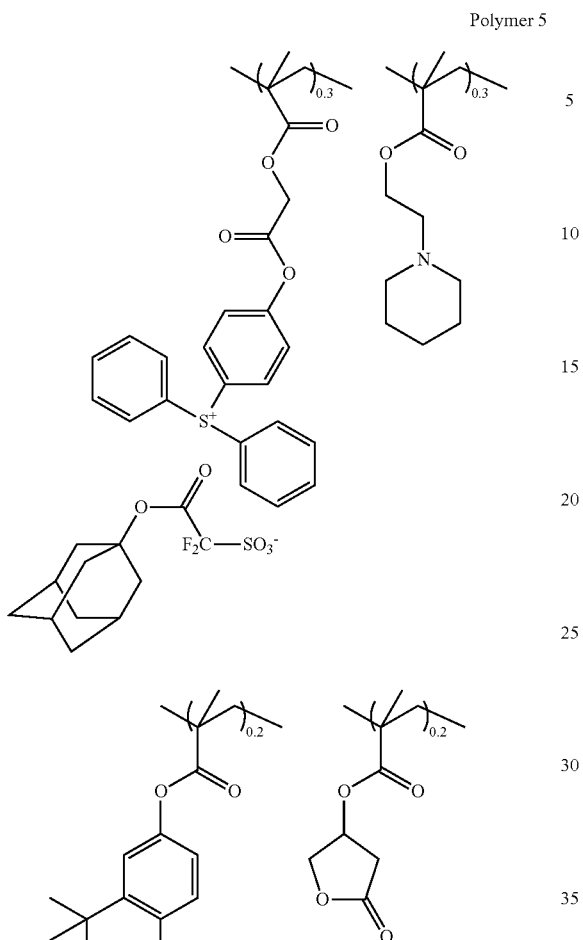

Synthesis Example 6

A 2-L flask was charged with 30.0 g of PAG Monomer 6, 6.3 g of 1,2,6-trimethyl-4-piperidyl methacrylate, 5.0 g of 3-tert-pentyl-4-hydroxyphenyl methacrylate, 4.5 g of 3-oxo-2,7-dioxatricyclo[4.2.1.0$^{4,8}$]nonan-9-yl methacrylate, and 40 g of THF solvent. The reactor was cooled at −70° C. in nitrogen atmosphere, after which vacuum pumping and nitrogen blow were repeated three times. The reactor was warmed up to room temperature, whereupon 1.2 g of AIBN as polymerization initiator was added. The reactor was heated at 60° C., whereupon reaction ran for 15 hours. The reaction solution was poured into 1 L of isopropyl alcohol for precipitation. The precipitate was collected by filtration and dried in vacuum at 60° C., yielding a white polymer, designated Polymer 6. The polymer was analyzed by $^{13}$C- and $^1$H-NMR and GPC, with the results shown below.

Copolymer Composition Ratio (Molar Ratio)

PAG Monomer 6: 1,2,6-trimethyl-4-piperidyl methacrylate:3-tert-pentyl-4-hydroxyphenyl methacrylate:3-oxo-2,7-dioxatricyclo[4.2.1.0$^{4,8}$]nonan-9-yl methacrylate=0.3:0.3:0.2:0.2

Mw=8,900

Mw/Mn=1.61

Polymer 6

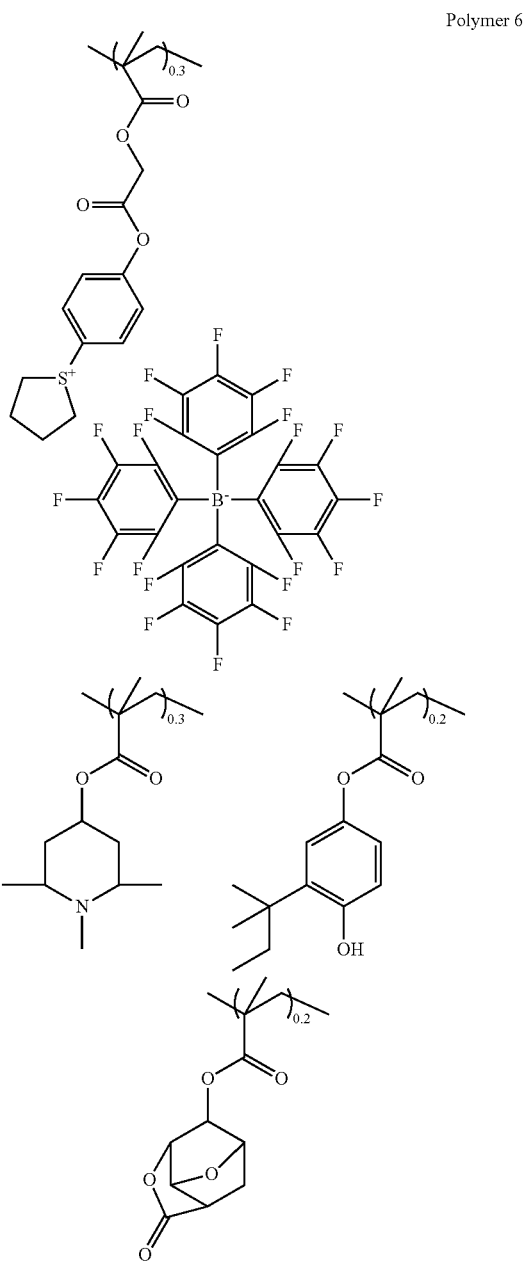

Synthesis Example 7

A 2-L flask was charged with 17.6 g of PAG Monomer 7, 6.8 g of 2,2,6,6-tetramethyl-4-piperidyl methacrylate, 4.7 g of 3-tert-butyl-4-hydroxyphenyl methacrylate, 4.0 g of β-methacryloxy-β,γ-dimethyl-γ-butyrolactone, and 40 g of THF solvent. The reactor was cooled at −70° C. in nitrogen atmosphere, after which vacuum pumping and nitrogen blow were repeated three times. The reactor was warmed up to room temperature, whereupon 1.2 g of AIBN as polymerization initiator was added. The reactor was heated at 60° C., whereupon reaction ran for 15 hours. The reaction solution was poured into 1 L of isopropyl alcohol for precipitation. The precipitate was collected by filtration and dried in vacuum at 60° C., yielding a white polymer, designated Polymer 7. The polymer was analyzed by $^{13}$C- and $^1$H-NMR and GPC, with the results shown below.

Copolymer Composition Ratio (Molar Ratio)
PAG Monomer 7: 2,2,6,6-tetramethyl-4-piperidyl methacrylate:3-tert-butyl-4-hydroxyphenyl methacrylate:β-methacryloxy-β,γ-dimethyl-γ-butyrolactone=0.3:0.3:0.2:0.2
Mw=8,400
Mw/Mn=1.64

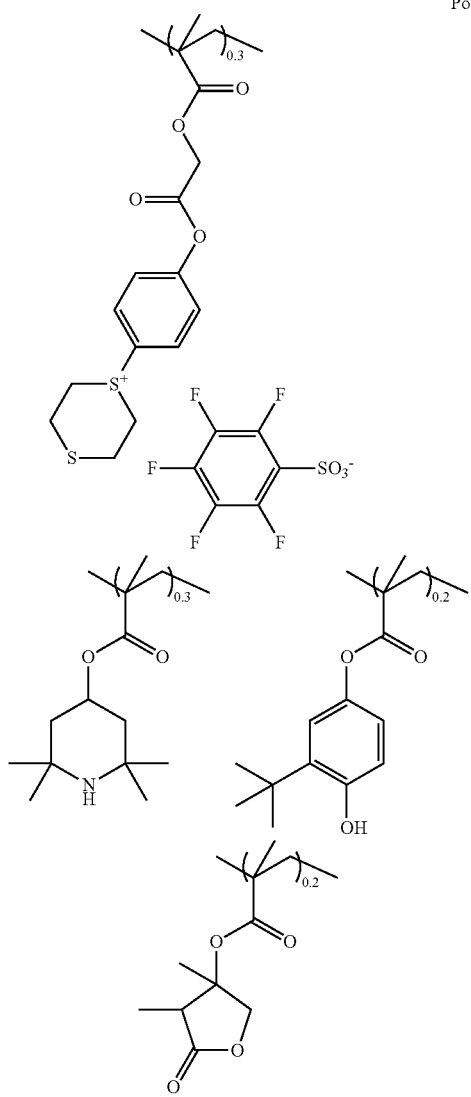

Polymer 7

Synthesis Example 8

A 2-L flask was charged with 16.0 g of PAG Monomer 8, 6.8 g of 2,2,6,6-tetramethyl-4-piperidyl methacrylate, 4.4 g of 4-acetyl-3-hydroxyphenyl methacrylate, 4.0 g of β-methacryloxy-β,γ-dimethyl-γ-butyrolactone, and 40 g of THF solvent. The reactor was cooled at −70° C. in nitrogen atmosphere, after which vacuum pumping and nitrogen blow were repeated three times. The reactor was warmed up to room temperature, whereupon 1.2 g of AIBN as polymerization initiator was added. The reactor was heated at 60° C., whereupon reaction ran for 15 hours. The reaction solution was poured into 1 L of isopropyl alcohol for precipitation. The precipitate was collected by filtration and dried in vacuum at 60° C., yielding a white polymer, designated Polymer 8. The polymer was analyzed by $^{13}$C- and $^{1}$H-NMR and GPC, with the results shown below.

Copolymer Composition Ratio (Molar Ratio)
PAG Monomer 8: 2,2,6,6-tetramethyl-4-piperidyl methacrylate:4-acetyl-3-hydroxyphenyl methacrylate:β-methacryloxy-β,γ-dimethyl-γ-butyrolactone=0.3:0.3:0.2:0.2
Mw=8,100
Mw/Mn=1.77

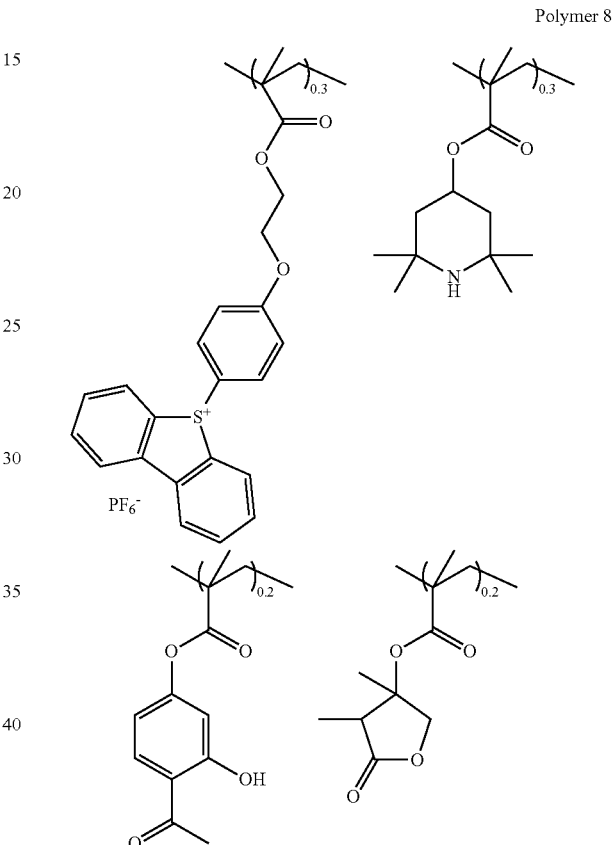

Polymer 8

Synthesis Example 9

A 2-L flask was charged with 27.6 g of PAG Monomer 9, 6.8 g of 2,2,6,6-tetramethyl-4-piperidyl methacrylate, 8.8 g of 5-acetyl-3-hydroxyphenyl methacrylate, and 40 g of THF solvent. The reactor was cooled at −70° C. in nitrogen atmosphere, after which vacuum pumping and nitrogen blow were repeated three times. The reactor was warmed up to room temperature, whereupon 1.2 g of AIBN as polymerization initiator was added. The reactor was heated at 60° C., whereupon reaction ran for 15 hours. The reaction solution was poured into 1 L of isopropyl alcohol for precipitation. The precipitate was collected by filtration and dried in vacuum at 60° C., yielding a white polymer, designated Polymer 9. The polymer was analyzed by $^{13}$C- and $^{1}$H-NMR and GPC, with the results shown below.

Copolymer Composition Ratio (Molar Ratio)
PAG Monomer 9: 2,2,6,6-tetramethyl-4-piperidyl methacrylate:5-acetyl-3-hydroxyphenyl methacrylate=0.3:0.3:0.4

Mw=8,900
Mw/Mn=1.82

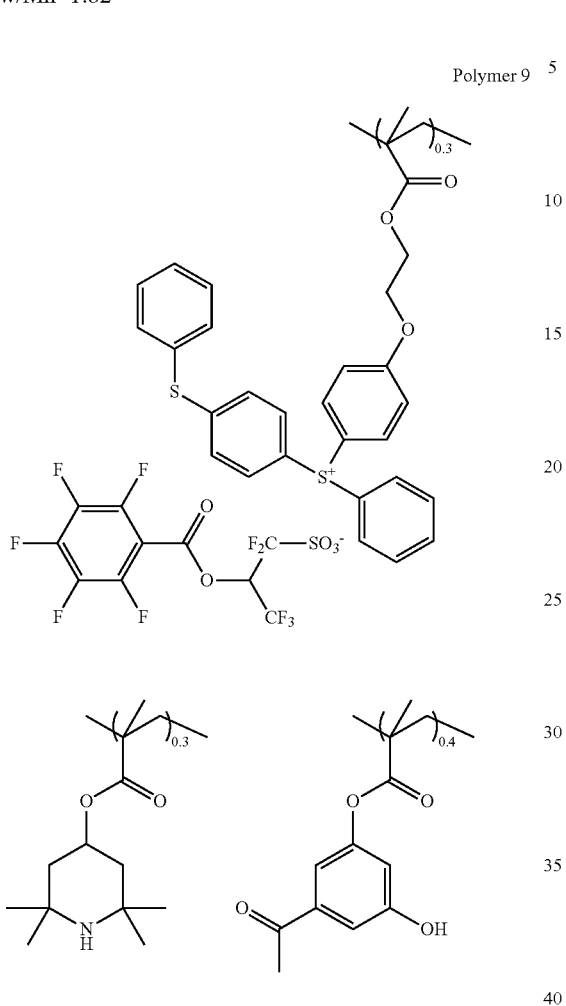

Polymer 9

Synthesis Example 10

A 2-L flask was charged with 14.9 g of PAG Monomer 10, 6.8 g of 2,2,6,6-tetramethyl-4-piperidyl methacrylate, 3.9 g of 3-fluoro-2-hydroxyphenyl methacrylate, 3.9 g of 5-hydroxynaphthalen-1-yl methacrylate, and 40 g of THF solvent. The reactor was cooled at −70° C. in nitrogen atmosphere, after which vacuum pumping and nitrogen blow were repeated three times. The reactor was warmed up to room temperature, whereupon 1.2 g of AIBN as polymerization initiator was added. The reactor was heated at 60° C., whereupon reaction ran for 15 hours. The reaction solution was poured into 1 L of isopropyl alcohol for precipitation. The precipitate was collected by filtration and dried in vacuum at 60° C., yielding a white polymer, designated Polymer 10. The polymer was analyzed by $^{13}$C- and $^1$H-NMR and GPC, with the results shown below.

Copolymer Composition Ratio (Molar Ratio)

PAG Monomer 10: 2,2,6,6-tetramethyl-4-piperidyl methacrylate:3-fluoro-2-hydroxyphenyl methacrylate:5-hydroxynaphthalen-1-yl methacrylate=0.3:0.3:0.2:0.2

Mw=7,900

Mw/Mn=1.65

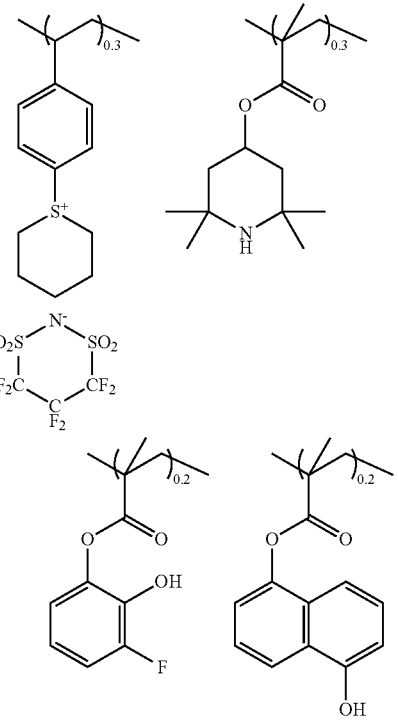

Polymer 10

Comparative Synthesis Example 1

Comparative Polymer 1 was synthesized by the same procedure as in Synthesis Example 1 aside from omitting 2-(dimethylamino)ethyl methacrylate. The polymer was analyzed by $^{13}$C- and $^1$H-NMR and GPC, with the results shown below.

Copolymer Composition Ratio (Molar Ratio)

PAG Monomer 1: 4-hydroxyphenyl methacrylate=0.3:0.7

Mw=9,100

Mw/Mn=1.70

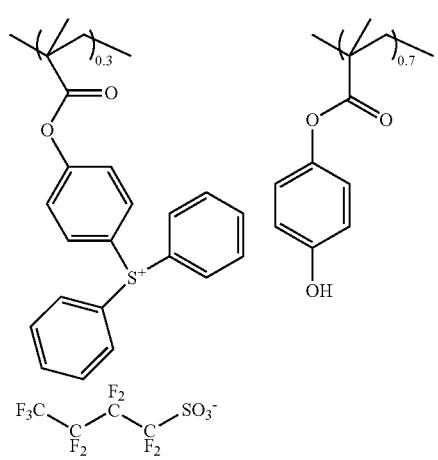

Comparative Polymer 1

Comparative Synthesis Example 2

Comparative Polymer 2 was synthesized by the same procedure as in Synthesis Example 1 aside from omitting PAG Monomer 1. The polymer was analyzed by $^{13}$C- and $^1$H-NMR and GPC, with the results shown below.
Copolymer Composition Ratio (Molar Ratio)
2-(dimethylamino)ethyl methacrylate:4-hydroxyphenyl methacrylate=0.3:0.7
Mw=10,100
Mw/Mn=1.3

Comparative Polymer 2

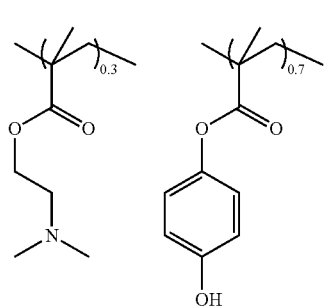

Comparative Synthesis Example 3

A 2-L flask was charged with 8.2 g of 3-ethyl-3-exotetracyclo[4.4.0.1$^{2,5}$.1$^{7,10}$]dodecanyl methacrylate, 3.1 g of 2-(dimethylamino)ethyl methacrylate, 3.6 g of 4-hydroxyphenyl methacrylate, 4.5 g of 3-oxo-2,7-dioxa-tricyclo[4.2.1.0$^{4,8}$]nonan-9-yl methacrylate, 6.4 g of PAG Monomer 1, and 40 g of THF solvent. The reactor was cooled at −70° C. in nitrogen atmosphere, after which vacuum pumping and nitrogen blow were repeated three times. The reactor was warmed up to room temperature, whereupon 1.2 g of AIBN as polymerization initiator was added. The reactor was heated at 60° C., whereupon reaction ran for 15 hours. The reaction solution was poured into 1 L of isopropyl alcohol for precipitation. The precipitate was collected by filtration and dried in vacuum at 60° C., yielding a white polymer, designated Comparative Polymer 3. The polymer was analyzed by $^{13}$C- and $^1$H-NMR and GPC, with the results shown below.
Copolymer Composition Ratio (Molar Ratio)
3-ethyl-3-exotetracyclo[4.4.0.1$^{2,5}$.1$^{7,10}$]dodecanyl methacrylate:2-(dimethylamino)ethyl methacrylate:4-hydroxyphenyl methacrylate:3-oxo-2,7-dioxatricyclo[4.2.1.0$^{4,8}$]nonan-9-yl methacrylate:PAG Monomer 1=0.3:0.2:0.2:0.2:0.1
Mw=7,300
Mw/Mn=1.88

Comparative Polymer 3

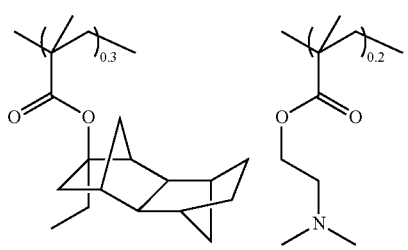

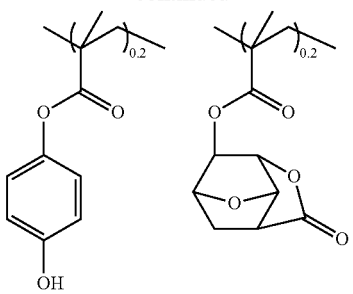

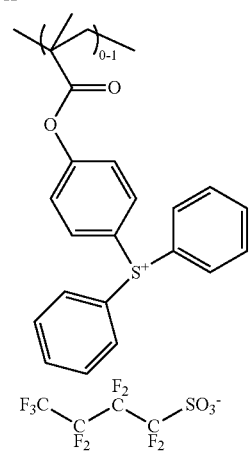

Comparative Synthesis Example 4

Comparative Polymer 4 was synthesized by the same procedure as in Synthesis Example 1 aside from using Comparative PAG Monomer 1 instead of PAG Monomer 1. The polymer was analyzed by $^{13}$C- and $^1$H-NMR and GPC, with the results shown below.
Copolymer Composition Ratio (Molar Ratio)
Comparative PAG Monomer 1: 2-(dimethylamino)ethyl methacrylate:4-hydroxyphenyl methacrylate=0.2:0.3:0.5
Mw=10,100
Mw/Mn=1.71

Comparative Polymer 4

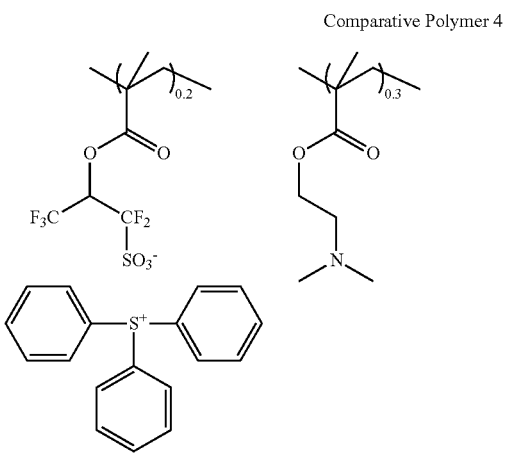

-continued

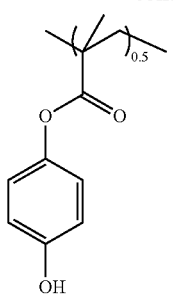

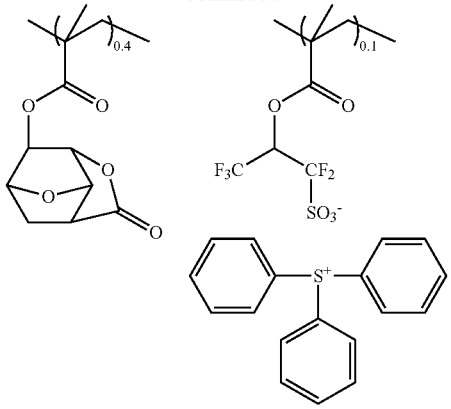

Comparative Synthesis Example 5

A flask was charged with 8.2 g of 3-ethyl-3-exotetracyclo[4.4.0.1$^{2,5}$.1$^{7,10}$]dodecanyl methacrylate, 3.6 g of 4-hydroxyphenyl methacrylate, 9.0 g of 3-oxo-2,7-dioxatricyclo[4.2.1.0$^{4,8}$]nonan-9-yl methacrylate, 5.6 g of Comparative PAG Monomer 1, and 40 g of THF solvent. The reactor was cooled at −70° C. in nitrogen atmosphere, after which vacuum pumping and nitrogen blow were repeated three times. The reactor was warmed up to room temperature, whereupon 1.2 g of AIBN as polymerization initiator was added. The reactor was heated at 60° C., whereupon reaction ran for 15 hours. The reaction solution was poured into 1 L of isopropyl alcohol for precipitation. The precipitate was collected by filtration and dried in vacuum at 60° C., yielding a white polymer, designated Comparative Polymer 5. The polymer was analyzed by $^{13}$C- and $^1$H-NMR and GPC, with the results shown below.

Copolymer Composition Ratio (Molar Ratio)

3-ethyl-3-exotetracyclo[4.4.0.1$^{2,5}$.1$^{7,10}$]dodecanyl methacrylate:4-hydroxyphenyl methacrylate:3-oxo-2,7-dioxatricyclo[4.2.1.0$^{4,8}$]nonan-9-yl methacrylate: Comparative PAG Monomer 1=0.3:0.2:0.4:0.1

Mw=7,300
Mw/Mn=1.88

Comparative Polymer 5

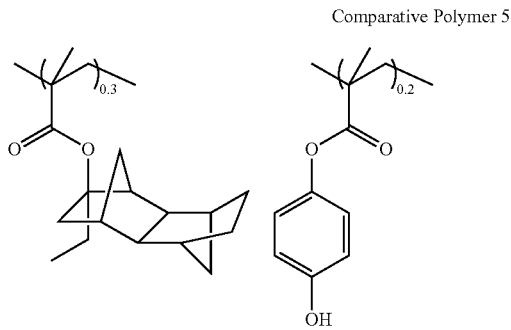

2. Preparation of Resist Composition

Examples 1 to 10 and Comparative Examples 1 to 6

Positive resist compositions were prepared by dissolving the polymer and components in a solvent in accordance with the recipe shown in Table 1, and filtering through a filter having a pore size of 0.2 μm. The solvent contained 100 ppm of surfactant FC-4430 (3M). The components in Table 1 are as identified below.

Polymers 1 to 10:
  as synthesized in Synthesis Examples 1 to 10
Comparative Polymers 1 to 5:
  as synthesized in Comparative Synthesis Examples 1 to 5
Organic Solvents:
  PGMEA (propylene glycol monomethyl ether acetate)
  PGME (propylene glycol monomethyl ether)
  CyH (cyclohexanone)
Basic Compound:
  Amine 1 of the following structural formula Amine 1

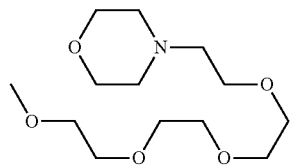

3. EB Lithography Patterning Test

Using a coater/developer system Clean Track Mark 5 (Tokyo Electron Ltd.), the positive resist composition was spin coated onto a silicon substrate of diameter 6 inches (which had been vapor primed with hexamethyldisilazane) and prebaked on a hot plate at 110° C. for 60 seconds to form a resist film of 80 nm thick. Using a system HL-800D (Hitachi Ltd.) at an accelerating voltage of 50 kV, the resist film was exposed imagewise to EB in a vacuum chamber.

Using Clean Track Mark 5, after the exposure, the resist film was baked (PEB) on a hot plate at the temperature shown in Table 1 for 60 seconds and puddle developed in the developer shown in Table 1 for 30 seconds to form a positive pattern.

Resolution is a minimum size at the exposure dose (sensitivity) that provides a 1:1 resolution of a 100-nm line-and-space pattern. The 100-nm L/S pattern was measured for roughness (LWR) under SEM. Table 1 shows the composition of resist and the sensitivity, resolution and LWR on EB lithography.

where the amino group forms a salt with acid is dissolved in the developer. In Comparative Example 4, such contradictory phenomena occurred simultaneously, leaving film resi-

TABLE 1

| | | Polymer (pbw) | Basic compound (pbw) | Organic solvent (pbw) | PEB temp. (° C.) | Developer | Sensitivity ($\mu C/cm^2$) | Resolution (nm) | LWR (nm) |
|---|---|---|---|---|---|---|---|---|---|
| Example | 1 | Polymer 1 (100) | — | PGMEA(1,500) CyH(200) | — | 2-heptanone | 80 | 70 | 3.2 |
| | 2 | Polymer 2 (1003 | — | PGMEA(1,500) CyH(200) | 70 | butyl acetate | 85 | 70 | 3.8 |
| | 3 | Polymer 3 (100) | — | PGMEA(1,500) CyH(200) | — | butyl acetate | 75 | 75 | 3.4 |
| | 4 | Polymer 4 (100) | — | PGMEA(1,500) CyH(200) | — | butyl acetate | 75 | 75 | 3.1 |
| | 5 | Polymer 5 (100) | — | PGMEA(500) CyH(1,450) PGME(50) | 70 | butyl acetate | 85 | 70 | 3.4 |
| | 6 | Polymer 6 (100) | — | PGMEA(500) CyH(1,450) PGME(50) | 80 | isopentyl acetate | 45 | 70 | 3.6 |
| | 7 | Polymer 7 (100) | — | PGMEA(500) CyH(1,450) PGME(50) | 60 | butyl acetate | 48 | 70 | 3.3 |
| | 8 | Polymer 8 (100) | — | PGMEA(500) CyH(1,450) PGME(50) | 80 | butyl acetate | 85 | 70 | 3.0 |
| | 9 | Polymer 9 (100) | — | PGMEA(500) CyH(1,450) PGME(50) | 80 | pentyl acetate | 90 | 70 | 3.7 |
| | 10 | Polymer 10 (100) | — | PGMEA(500) CyH(1,450) PGME(50) | 80 | butyl acetate | 50 | 70 | 3.5 |
| Comparative Example | 1 | Comparative Polymer 1 (100) | — | PGMEA(500) CyH(1,450) PGME(50) | — | butyl acetate | — | film remaining in both exposed and unexposed regions | — |
| | 2 | Comparative Polymer 2 (100) | — | PGMEA(1,500) | — | butyl acetate | — | no film remaining in exposed and unexposed regions | — |
| | 3 | Comparative Polymer 1 (50) Comparative Polymer 2 (50) | — | PGMEA(500) CyH(1,450) PGME(50) | — | butyl acetate | — | film remaining in both exposed and unexposed regions | — |
| | 4 | Comparative Polymer 3 (100) | — | PGMEA(500) CyH(1,450) PGME(50) | — | butyl acetate | — | film remaining in both exposed and unexposed regions | — |
| | 5 | Comparative Polymer 4 (100) | — | PGMEA(500) CyH(1,450) PGME(50) | — | butyl acetate | — | negative pattern, pattern collapse | — |
| | 6 | Comparative Polymer 5 (100) | Amine 1 (1.0) | PGMEA(500) CyH(1,450) PGME(50) | 90 | 2.38 wt % TMAH aqueous solution | 32 | 75 | 6.1 |

As is evident from Table 1, a non-chemically-amplified positive resist composition comprising a polymer comprising recurring units having a sulfonium salt bound to the backbone and recurring units containing an amino group exhibits a high resolution and a low edge roughness. In Comparative Example 1, the decomposition of the sulfonium salt upon light exposure occurred, but contributed to only a slight increase of solubility in the developer so that the exposed region of resist film is not fully dissolved, failing to form a positive pattern. In Comparative Example 2, since no polarity switch occurred upon light exposure, both the exposed and unexposed regions of resist film were dissolved in the developer. In Comparative Example 3, since Comparative Polymers 1 and 2 were not uniformly mixed within the film, dissolved areas were intermingled with undissolved areas and so residues were left after development. The region where the acid labile group is deprotected becomes insoluble in the developer, whereas the region dues. In Comparative Example 5, the backbone-bound sulfonic acid generated upon light exposure formed a salt with the backbone-bound amino group between molecules to provide intermolecular crosslinking so that the composition might work as negative resist, but no pattern could be formed due to swell. Comparative Example 6 was a conventional chemically amplified resist composition, which exhibited an increase of sensitivity, but a loss of resolution and edge roughness owing to acid diffusion.

Japanese Patent Application No. 2016-029682 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A positive resist composition adapted to form a positive pattern via organic solvent development, comprising a base resin containing a polymer comprising recurring units having the formula (1) and recurring units having the formula (2), but not recurring units adapted to increase a polarity by deprotection reaction with the aid of acid,

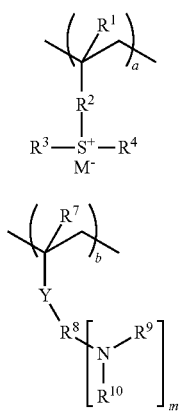

wherein $R^1$ and $R^7$ are each independently hydrogen or methyl, $R^2$ is a single bond, phenylene, —O—$R^5$— or —C(=O)—X—$R^5$—, X is —O— or —NH—, $R^5$ is a $C_1$-$C_6$ straight, branched or cyclic alkylene group, $C_2$-$C_6$ straight, branched or cyclic alkenylene group, phenylene group, or a combination thereof, which may contain a carbonyl, ester, ether or hydroxyl moiety, $R^3$ and $R^4$ are each independently a $C_1$-$C_{12}$ straight, branched or cyclic alkyl group, $C_6$-$C_{12}$ aryl group, $C_7$-$C_{20}$ aralkyl group or mercaptophenyl group, which may contain a carbonyl, ester or ether moiety, Y is a single bond, phenylene group or —C(=O)—O—, $R^8$ is a single bond, a $C_1$-$C_{10}$ straight, branched or cyclic alkylene group which may contain an ether moiety, ester moiety, —N= or —S—, or phenylene or naphthylene group, $R^9$ and $R^{10}$ are each independently hydrogen, $C_1$-$C_{10}$ straight or branched alkyl group, $C_2$-$C_{10}$ alkenyl group or $C_6$-$C_{10}$ aryl group, $R^9$ and $R^{10}$ may bond together to form a ring with the nitrogen atom to which they are attached, the ring may contain an ether moiety, sulfide moiety, disulfone moiety, nitrogen atom, double bond or aromatic moiety, either one of $R^9$ and $R^{10}$ may bond with $R^8$ to form a ring, $M^-$ is a non-nucleophilic counter ion containing at least one fluorine atom, a and b are numbers meeting $0.1 \leq a \leq 0.9$, $0.1 \leq b \leq 0.9$, and $0.1 \leq a/b \leq 1.5$, and m is 1, wherein the polymer further comprises recurring units containing a phenolic hydroxyl group having the formula (3):

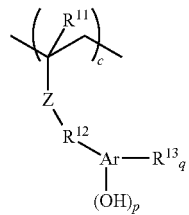

wherein Ar is a $C_6$-$C_{14}$ aromatic group which may contain a nitrogen atom, $R^{11}$ is hydrogen or methyl, $R^{12}$ is a single bond or a $C_1$-$C_{10}$ straight or branched alkylene group which may contain a hydroxyl, carboxyl, ester, ether moiety or lactone ring, $R^{13}$ is hydrogen, fluorine, trifluoromethyl, cyano, $C_1$-$C_{10}$ straight, branched or cyclic alkyl group, $C_1$-$C_{10}$ straight, branched or cyclic alkoxy group, $C_6$-$C_{14}$ aryl group, $C_2$-$C_{10}$ straight, branched or cyclic alkenyl group, $C_2$-$C_{10}$ straight, branched or cyclic alkynyl group, $C_2$-$C_{10}$ straight, branched or cyclic alkoxycarbonyl group, $C_2$-$C_{10}$ straight, branched or cyclic acyl group, or $C_2$-$C_{10}$ straight, branched or cyclic acyloxy group, p is an integer of 1 to 5, q is an integer of 0 to 4, Z is a single bond, —C(=O)—O— or —C(=O)—NH—.

2. The positive resist composition of claim 1, further comprising an organic solvent.

3. The positive resist composition of claim 1, further comprising a surfactant.

4. A pattern forming process comprising the steps of applying the positive resist composition of claim 1 onto a substrate, baking the composition to form a resist film, exposing the resist film to high-energy radiation, and developing the resist film in an organic solvent developer.

5. The pattern forming process of claim 4 wherein the high-energy radiation is EB or EUV of wavelength 3 to 15 nm.

6. The pattern forming process of claim 4 wherein the developer contains at least one organic solvent selected from the group consisting of 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

* * * * *